United States Patent
Sherman et al.

(10) Patent No.: US 11,530,204 B2
(45) Date of Patent: Dec. 20, 2022

(54) BIOCATALYTIC SYNTHESIS OF CRYPTOPHYCIN ANTICANCER AGENTS

(71) Applicant: THE REGENTS OF THE UNIVERSITY OF MICHIGAN, Ann Arbor, MI (US)

(72) Inventors: David H. Sherman, Ann Arbor, MI (US); Jennifer J. Schmidt, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 17/039,001

(22) Filed: Sep. 30, 2020

(65) Prior Publication Data

US 2021/0094942 A1 Apr. 1, 2021

Related U.S. Application Data

(60) Provisional application No. 62/908,103, filed on Sep. 30, 2019.

(51) Int. Cl.
  *C07D 413/06* (2006.01)
  *C07D 213/06* (2006.01)
  *A61K 31/44* (2006.01)

(52) U.S. Cl.
  CPC .................. *C07D 413/06* (2013.01)

(58) Field of Classification Search
  CPC .................................................. C07D 413/06
  See application file for complete search history.

(56) References Cited

U.S. PATENT DOCUMENTS

| | | | |
|---|---|---|---|
| 5,466,468 A | 11/1995 | Schneider et al. | |
| 6,013,626 A | 1/2000 | Moore et al. | |
| 6,680,311 B1 * | 1/2004 | Al-Awar | C07D 413/06 514/183 |
| 2002/0128185 A1 | 9/2002 | Shih | |

FOREIGN PATENT DOCUMENTS

| | | |
|---|---|---|
| WO | 1998/08505 A1 | 3/1998 |
| WO | 2005/116200 A2 | 12/2005 |
| WO | 2009/002993 | 12/2008 |
| WO | 2011/001052 A1 | 1/2011 |
| WO | 2016/146638 A1 | 9/2016 |
| WO | 2017/076998 A1 | 5/2017 |

OTHER PUBLICATIONS

Trauger et al., Cyclization of backbone-substituted peptides catalyzed by the thioesterase domain from the tyrocidine nonribosomal peptide synthetase, Biochemistry, 40(24):7092-7098 (2001).
Trauger et al., Peptide cyclization catalysed by the thioesterase domain of tyrocidine synthetase, Nature, 407(6801):215-218 (2000).
Tsai et al., Crystal structure of the macrocycle-forming thioesterase domain of the erythromycin polyketide synthase: Versatility from a unique substrate channel, P. Natl. Acad. Sci. U.S.A., 98(26):14808-14813 (2001).
Verma et al., The cryptophycins as potent payloads for antibody drug conjugates, Bioorg. Med. Chem. Lett., 25(4):864-868 (2015).
Wagner et al., In vitro pharmacology of cryptophycin 52 (LY355703) in human tumor cell lines, Cancer Chemotherapy and Pharmacology, 43(2):115-125 (1999).
Walsh et al., Insights into the chemical logic and enzymatic machinery of NRPS assembly lines, Nat. Prod. Rep., 33(2):127-35 (2016).
Weissman et al., Combinatorial biosynthesis of reduced polyketides, Nat. Rev. Microbiol., 3(12):925-36 (2005).
Weissman, Genetic engineering of modular PKSs: from combinatorial biosynthesis to synthetic biology, Nat. Prod. Rep.,33(2):203-30 (2016).
Yeh et al., Enhanced macrocyclizing activity of the thioesterase from tyrocidine synthetase in presence of nonionic detergent, Chem. Biol., 11(11):1573-1582 (2004).
International Application No. PCT/US20/53575, International Search Report and Written Opinion, dated Nov. 27, 2020.
Schmidt et al., A Versatile Chemoenzymatic Synthesis for the Discovery of Potent Cryptophycin Analogs, ACS Chem. Bio., 15(2):524-532 (2020).
Akey et al., Structural basis for macrolactonization by the pikromycin thioesterase, Nature Chemical Biology, 2(10):537-542 (2006).
ASHP Handbook on injectable drugs, Toissel, 4th ed., 622-630 (1986).
Banker et al., Pharmaceutics and Pharmacy Practice, J. B. Lippincott Company, Philadelphia, PA, pp. 238-250 (1982).
Beck et al., Chemoenzymatic synthesis of cryptophycin/arenastatin natural products, Biochemistry, 44:13457-13466 (2005).
Berge et al., Pharmaceutical salts, J. Pharmaceutical Sciences, 66(1):1-19 (1977).
Bolduc et al., Efficient, divergent synthesis of cryptophycin unit A analogues, Chem. Commun (Camb), (2012).
Bruner et al., Structural basis for the cyclization of the lipopeptide antibiotic surfactin by the thioesterase domain SrfTE, Structure, 10(3):301-310 (2002).
Buck et al., Total synthesis and anti-tubulin activity of epi-c3 analogues of cryptophycin-24, J. Med. Chem., 47:3697-9 (2004).
Clouthier et al., Expanding the organic toolbox: a guide to integrating biocatalysis in synthesis, Chem. Soc. Rev., 41(4):1585-1605 (2012).
D'Agostino et al., A multicenter phase II study of the cryptophycin analog LY355703 in patients with platinum-resistant ovarian cancer, Gynecological Cancer Society, 16(1):71-6 (2006).
Davis et al., Preparation and characterization of antibodies with specificity for the amino-terminal tetrapeptide sequence of the platelet-derived connective tissue activating peptide-III, Biochem. Intl., 10: 394-414 (1985).

(Continued)

*Primary Examiner* — Zinna Northington Davis
(74) *Attorney, Agent, or Firm* — Marshall, Gerstein & Borun LLP

(57) ABSTRACT

The disclosure provides cryptophycin intermediates, cryptophycin analogs, and cryptophycin chimeric molecules useful in treating cancer, as well as methods of producing these compounds and methods of treating cancer.

19 Claims, 12 Drawing Sheets

(56) References Cited

OTHER PUBLICATIONS

Ding et al., Chemoenzymatic synthesis of cryptophycin anticancer agents by an ester bondforming non-ribosomal peptide synthetase module, J. Am. Chem. Soc., 133(37):14492-5 (2011).

Driggers et al., The exploration of macrocycles for drug discovery—an underexploited structural class, Nature Reviews Drug Discovery, 7(7):608-624 (2008).

Edelman et al., Phase 2 study of cryptophycin 52 (L Y355703) in patients previously treated with platinum based chemotherapy for advanced non-small cell lung cancer, Lung Cancer, 39(2):197-9 (2003).

Eggen et al., The cryptophycins: their synthesis and anticancer activity, Medicinal Research Reviews, 22(2):85-101 (2002).

Erickson et al., Solid-phase peptide synthesis, The Proteins, 3rd ed., 2:257-527 (1976).

Finn et al., The synthesis of peptides by Solution methods and emphasis on peptide hormones, in The Proteins, 3rd ed., 2:105-253 (1976).

Gao et al., Direct Generation of Acyclic Polypropionate Stereopolyads via Double Diastereo- and Enantioselective Iridium-Catalyzed Crotylation of 1,3-Diols: Beyond Stepwise Carbonyl Addition in Polyketide Construction, Journal of the American Chemical Society, 133(32):12795-12800 (2011).

Ghosh et al., Asymmetric syntheses of potent antitumor macrolides cryptophycin B and arenastatin A, European Journal of Organic Chemistry, 10:2131-2141 (2004).

Ghosh et al., Enantioselective Synthesis of (+)-Cryptophycin 52 (LY355703), a Potent Antimitotic Antitumor Agent, J. Org. Chem., 68(25):9823-9826 (2003).

Giraldes et al., Structural and mechanistic insights into polyketide macrolactonization from polyketide-based affinity labels, Nature Chemical Biology, 2(10):531-536 (2006).

Golakoti et al., Structure determination, conformational analysis, chemical stability studies, and antitumor evaluation of the cryptophycins. Isolation of 18 new analogs from *Nostoc* sp strain GSV 224, J. Am. Chem. Soc., 118(13):3323-3323 (1996).

Hansen et al., Identification of a Thioesterase Bottleneck in the Pikromycin Pathway through Full-Module Processing of Unnatural Pentaketides, J. Am. Chem. Soc., 139(38):13450-13455 (2017).

Horsman et al., Polyketide synthase and non-ribosomal peptide synthetase thioesterase selectivity: logic gate or a victim of fate?, Nat. Prod. Rep., 33(2):183-202 (2016).

Koch et al., A Single Active Site Mutation in the Pikromycin Thioesterase Generates a More Effective Macrocyclization Catalyst, J. Am. Chem. Soc., 139(38):13456-13465 (2017).

Kohli et al., Enzymology of acyl chain macrocyclization in natural product biosynthesis, Chem. Commun (Camb), (3):297-307 (2003).

Kopp et al., Chemoenzymatic design of acidic lipopeptide hybrids: New insights into the structure-activity relationship of daptomycin and A54145, Biochemistry, 45(35):10474-10481 (2006).

Kotoku et al., Synthesis of 15,20-triamide analogue with polar substituent on the phenyl ring of arenastatin A, an extremely potent cytotoxic spongean depsipeptide, Bioorganic & Medicinal Chemistry, 14(22):7446-7457 (2006).

Krishnamurthy, Rapid reduction of alkyl tosylates with lithium triethylborohydride. A convenient and advantageous procedure for the deoxygenation of simple and hindered alcohols. Comparison of various hydride reagents, Journal of Organometallic Chemistry, 156(1):171-181 (1978).

Larsen et al., The Merrifield peptide synthesis studied by near-infrared Fourier-transform Raman spectroscopy, J. Am. Chem. Soc., 115(14):6247-6253 (1993).

Magarvey et al., Biosynthetic characterization and chemoenzymatic assembly of the cryptophycins. Potent anticancer agents from cyanobionts, ACS. Chemical Biology, 1(12):766-79 (2006).

Mast et al., Efficient and versatile stereoselective synthesis of cryptophycins, Chemistry, 11:4667-77 (2005).

McCubbin et al., Total synthesis of cryptophycin analogues via a scaffold approach, Org. Lett., 8(14):2993-2996 (2006).

Merrifield, Solid Phase Peptide Synthesis. I. The Synthesis of a Tetrapeptide, J. Am. Chem. Soc., 85(14):2149-2154 (1963).

Morrill et al., Synthesis of functionalized vinyl boronates via rutheniumcatalyzed olefin cross-metathesis and subsequent conversion to vinyl halides, Journal of Organic Chemistry, 68:6031-6034 (2003).

Mortison et al., Frontiers and opportunities in chemoenzymatic synthesis, J. Org. Chem., 75(21):7041-51 (2010).

Nahrwold et al., Conjugates of modified cryptophycins and RGD-peptides enter target cells by endocytosis, Journal of Medicinal Chemistry, 56(5):1853-64 (2013).

Nicolaou et al., A mild and selective method for the hydrolysis of esters with trimethyltin hydroxide, Angew. Chem. Int. Edit., 44(9):1378-1382 (2005).

O'Donnell et al., Solid-Phase Unnatural Peptide Synthesis (UPS), J. Am. Chem. Soc., 118(25):6070-6071 (1996).

Phukan et al., Facile Generation of Alkenes and Dienes from Tosylates, Synthesis, 9:1324-1328 (2003).

Pinto et al., 6-Deoxyerythronolide B Synthase Thioesterase-Catalyzed Macrocyclization Is Highly Stereoselective, Org. Lett., 14(9):2278-2281 (2012).

Remington's pharmaceutical sciences, 18th Ed. Mack Publishing Co., Easton, PA, 1435-1712 (1990).

Samel et al., The thioesterase domain of the fengycin biosynthesis cluster: A structural base for the macrocyclization of a nonribosomal lipopeptide, J. Mol. Biol., 359(4):876-889 (2006).

Schwartz et al., Pharmaceuticals from Cultured Algae, J. Ind. Microbiol., 5(2-3):113-123 (1990).

Sessa et al., Phase I and pharmacological studies of the cryptophycin analogue L Y355703 administered on a single intermittent or weekly schedule, European Journal of Cancer, 38(18):2388-2396 (2002).

Shankaraiah et al., Stereoselective Synthesis of (−)-Pinidinone, Helvetica Chimica Acta., 96(5):990-996 (2013).

Smith et al., Cryptophycin—a New Antimicrotubule Agent Active against Drug-Resistant Cells, Cancer Res., 54(14):3779-3784 (1994).

Smith et al., Solid-phase peptide synthesis and biological activity of bovine thymopoietin II (bTP-II), Int. J. Peptide Protein Res., 44(2):183-191 (1994).

Stevenson et al., Phase I trial of the cryptophycin analogue LY 355703 administered as an intravenous infusion on a day 1 and 8 schedule every 21 days, Clinical Cancer Research, 8(8):2524-9 (2002).

Su et al., Modulating Antibody-Drug Conjugate Payload Metabolism by Conjugation Site and Linker Modification, Bioconjugate Chem., 29(4):1155-1167 (2018).

Kumar et al., Design and synthesis of a new class of cryptophycins based tubulin inhibitors, Euro. J. Med. Chem., 93:55-63 (2015).

Schmidt et al., Poster Abstract: University of Michigan, Aug. 21-25, 252nd ACS National Meeting and Exposition, Philadelphia, PA, USA, Exploiting biocatalysis for the production of novel cryptophycin anticancer agents (2016).

\* cited by examiner

A)

B)

BIOCATALYTIC SYNTHESIS OF CRYPTOPHYCIN ANTICANCER AGENTS

STATEMENT OF GOVERNMENT INTEREST

This invention was made with government support under GM076477 and GM118101 awarded by the National Institutes of Health. The government has certain rights in the invention.

FIELD

The disclosure generally relates to analogs of naturally occurring compounds and uses thereof, such as in methods of treating, reducing the risk of, or ameliorating a symptom of, cancer such as colorectal cancer.

BACKGROUND

Polyketide synthases (PKSs), non-ribosomal peptide synthetases (NRPSs), and their hybrids (PKS/NRPS) are modular proteins that generate a vast array of complex natural products. These proteins select a group of relatively simple chemical building blocks (malonate, malonate derivatives, and/or amino acids) and construct diverse scaffolds with a wide range of biological activities.[1-2] A large class of these natural products, macrocycles[3] contain a constrained ring structure that both locks them into their biologically active conformation and that can protect peptide bonds from degradation.[4] The biosynthesis of these important molecules is typically terminated by a thioesterase (TE) domain, an α,β-hydrolase that utilizes a serine, histidine, aspartic acid catalytic triad to effect regio- and stereospecific cyclization.[4-6] The molecular mechanism by which these enzymes govern selectivity as well as organize the linear substrates for productive macrocyclization over hydrolysis has been poorly understood, which has limited our ability to predict and ultimately tune these enzymes for use as broad scope biocatalysts. Taking advantage of these discrete enzymes would be an unparalleled asset in the continued pursuit of methodologies to expand the existing synthetic toolbox for medicinal chemistry exploration.[6-8]

Pioneering work on PKS and NRPS TEs, comprised of both structural studies and in vitro biochemical analyses, have yielded important insights into the complex catalytic mechanisms that mediate cyclization. In the NRPS-derived tyrocidine and daptomycin TE systems, solid-phase peptide synthesis was utilized to formulate a suite of unnatural chain elongation intermediates that furnished novel macrocyclic analogs with varying biological activities.[9-11] This substrate tolerance has been attributed to a hydrogen bond network that enables substrate pre-organization. Thus, the TE was hypothesized to exert minimal influence except on the amino acid being employed as the intramolecular nucleophile, which appears to be critical for productive catalysis.[12] This is further supported by structural studies on NRPS TEs from the surfactin and fengycin biosynthetic pathways. Each possesses a large, bowl-shaped active site comprised predominantly of nonpolar and aromatic amino acids, with specific interactions occurring primarily at the hydroxyl-containing C-terminus of the linear NRPS substrate.[13-14]

Studies on the PKS TEs in the erythromycin (DEBS) and pikromycin (Pik) pathways have also benefited from structural and biochemical examination. This work has shown that a complex interplay of both specific functional group interactions and hydrophobic packing seen in the more channel-shaped active site are necessary for productive cyclization.[15-17] Despite some necessary constraints in both DEBS and Pik TEs, some amount of flexibility has been observed for non-essential elements, as has been demonstrated through a combination of docking and synthetic substrates that were able to formulate new macrocyclic products.[16, 18-19] Taking advantage of rational engineering, a single active-site mutation was generated that changed the underlying catalytic mechanism of PikTE, facilitating productive macrocyclization of previously inaccessible 12-membered macrolactones.[20] These compelling studies continue to shed light on the complexity of macrocyclization in various systems. Further investigations into PKS, NRPS, and PKS/NRPS hybrid TEs are necessary to expand our understanding of the factors that govern macrocyclization on a broad scale. Utilizing this knowledge has already facilitated protein engineering efforts that have expanded TE substrate flexibility, and continued efforts along these lines are expected to facilitate the generation of more active, and pharmacologically relevant, small molecule libraries.

The cryptophycins are a class of depsipeptides natural products generated by a mixed PKS/NRPS biosynthetic system.[21-22] They were first identified in Nostoc sp. ATCC 53789 as potent antifungals,[23] and were subsequently rediscovered in Nostoc sp. GSV 224 as one of the most potent anti-proliferative, microtubule binding agents.[24] An initial medicinal chemistry screening effort indicated that the β-epoxide functionality was necessary for maximal activity and that most modifications were detrimental to potency. A synthetic analog, cryptophycin 52 (FIG. 1) that contained a geminal-dimethyl functionality in unit C, entered clinical trials for treatment of platinum-resistant ovarian cancer.[25-27] Despite showing significant disease stabilization and an overall positive result, the trials were discontinued due to dose-limiting peripheral neuropathy and a lack of broad in vivo efficacy.[25, 28] Although the cryptophycin 52 clinical trials were terminated, this class of metabolites continues to represent a compelling scaffold for further lead optimization as it is particularly effective in difficult-to-treat, drug-resistant cancers.[29] Recently, the cryptophycins have been investigated extensively as potential payloads for antibody drug conjugates (as well as other direct targeting agents including conjugation with RGD peptides[30] and folic acid[31]), as this could circumvent the systemic toxicity observed with these compounds.[32-36] Although there is still significant interest in cryptophycins as anticancer agents, challenges in lead optimization as well as costly synthetic efforts for their production have stymied exploration. Based on earlier indications of the robust function of CrpTE[21], we were motivated to expand our chemoenzymatic approach for continued analog generation and biological evaluation, particularly at underexplored regions of the cryptophycin scaffold.

The final step in cryptophycin biosynthesis is macrocyclization of the chain elongation intermediate via CrpTE.[21] We demonstrated that excised CrpTE was able to catalyze facile cyclization, to varying degrees, of native and modified substrates to formulate cryptophycin 3, 51 (FIG. 1) and an unnatural cryptophycin containing a terminal olefin in unit A, originally synthesized as LY404291 at Eli Lilly.[37] Moreover, the CrpTE has also demonstrated utility by further operating in trans with the upstream NRPS module, CrpD-M2, in the production of cryptophycin 24 and 51.[22] These studies demonstrated the unique, inherent flexibility of CrpTE and its potential as a versatile biocatalyst for the production of novel cryptophycin analogs of medicinal importance. Toward that end, we embarked on an effort to generate a series of novel cryptophycin chain elongation intermediates designed to probe CrpTE substrate tolerance, and produce analogs that may address the limitations identified in clinical trials (dose limiting peripheral neuropathy and broad in vivo efficacy).[25, 28]

In view of the foregoing observations, it is apparent that a need continues to exist in the art for methods and substrates useful in synthesizing and using compound analogs such as cryptophycin analogs in the treatment, reduction of risk of developing, or amelioration of symptoms associated with, cancer such as colorectal cancer.

SUMMARY

The disclosure provides compounds of Formula I:

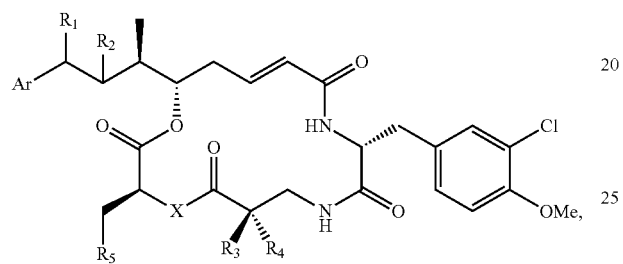

(I)

wherein Ar is a 5- to 7-membered heterocyclic aryl group having 1 to 3 ring heteroatoms selected from N, O, and S, and is optionally substituted with 1-3 substituents independently selected from $C_{1-5}$ alkyl and L-$R_6$; $R_1$ is chlorine, bromine, or iodine; $R_2$ is OH or $OC(O)CH_2NHR$; or $R_1$ and $R_2$ together (1) indicate a double bond between the carbons to which they are attached or (2) form a β-epoxide ring with the carbons to which they are attached; each of $R_3$ and $R_4$ is independently H, $C_{1-6}$alkylene-OH or $C_{0-6}$alkylene-NH(R); or $R_3$ and $R_4$ together with the carbon atom to which they are attached form a spiro $C_{3-5}$ cycloalkyl or a spiro 3- to 5-membered heterocycloalkyl having one nitrogen ring atom; $R_5$ is $C_{1-6}$alkyl, $C_{0-6}$alkylene-OH or $C_{0-6}$alkylene-NH(R); and R is H, $C_{1-6}$alkyl, or L-$R_6$; L is a linker; $R_6$ is a reactive chemical group; and X is O, NH or NMe, with the proviso that the compound or salt comprises 0 or 1 L-$R_6$.

In some embodiments, Ar comprises pyridyl, pyrazinyl, imidazolyl, or oxazolyl, optionally substituted with 1-3 substituents selected from methyl and isopropyl.

In various embodiments, (1) Ar is

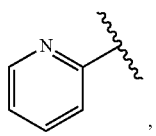

$R_3$ is $CH_3$, and $R_4$ is H; (2) Ar is

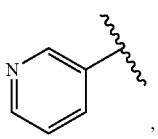

$R_3$ is $CH_3$, and $R_4$ is H or $CH_3$; (3) Ar is

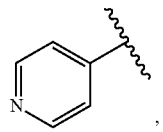

$R_3$ is $CH_3$, and $R_4$ is H or $CH_3$; (4) Ar is

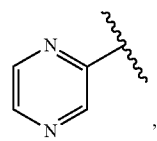

$R_3$ is $CH_3$, and $R_4$ is H; (5) Ar is

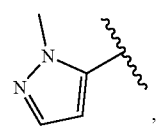

$R_3$ is $CH_3$, and $R_4$ is H; (6d) Ar is

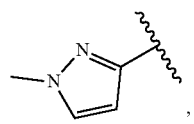 [SMILES: *c1ccn(C)n1]

$R_3$ is $CH_3$, and $R_4$ is H; (7) Ar is

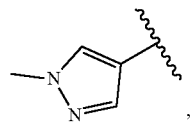 [SMILES: *c1cnn(C)c1]

$R_3$ is $CH_3$, and $R_4$ is H or $CH_3$; (8) Ar is

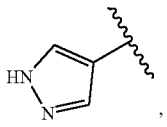

$R_3$ is $CH_3$, and $R_4$ is H or $CH_3$; (9) Ar is

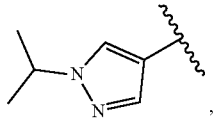 [SMILES: *c1cnn(C(C)C)c1]

, $R_3$ is $CH_3$, and $R_4$ is H; or (10) wherein Ar is

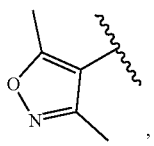 [SMILES: *c1c(C)noc1C]

$R_3$ is $CH_3$, and $R_4$ is H.

Further provided herein are methods of producing the compounds and salts described herein, comprising contacting a seco cryptophycin intermediate with a cryptophycin thioesterase under conditions suitable for macrocyclization to form the compound or salt.

Also provided herein are conjugates comprising the compounds or salts described herein and a peptide, a protein, or an antibody. In some cases, the antibody and the compound or salt are covalently attached via the reactive chemical group of the compound or salt and a complementary reactive group on the antibody.

Other aspects of the disclosure include pharmaceutical compositions comprising a compound as disclosed herein, a compound as disclosed herein for use in the preparation of a medicament for treating or preventing cancer in a subject, and the use of a compound as disclosed herein in a method of treating cancer in a subject.

Other features and advantages of the disclosure will become apparent from the following detailed description, including the drawing. It should be understood, however, that the detailed description and the specific examples, while indicating embodiments, are provided for illustration only, because various changes and modifications within the spirit and scope of the disclosure will become apparent to those skilled in the art from the detailed description.

DETAILED DESCRIPTION

Figure 1:
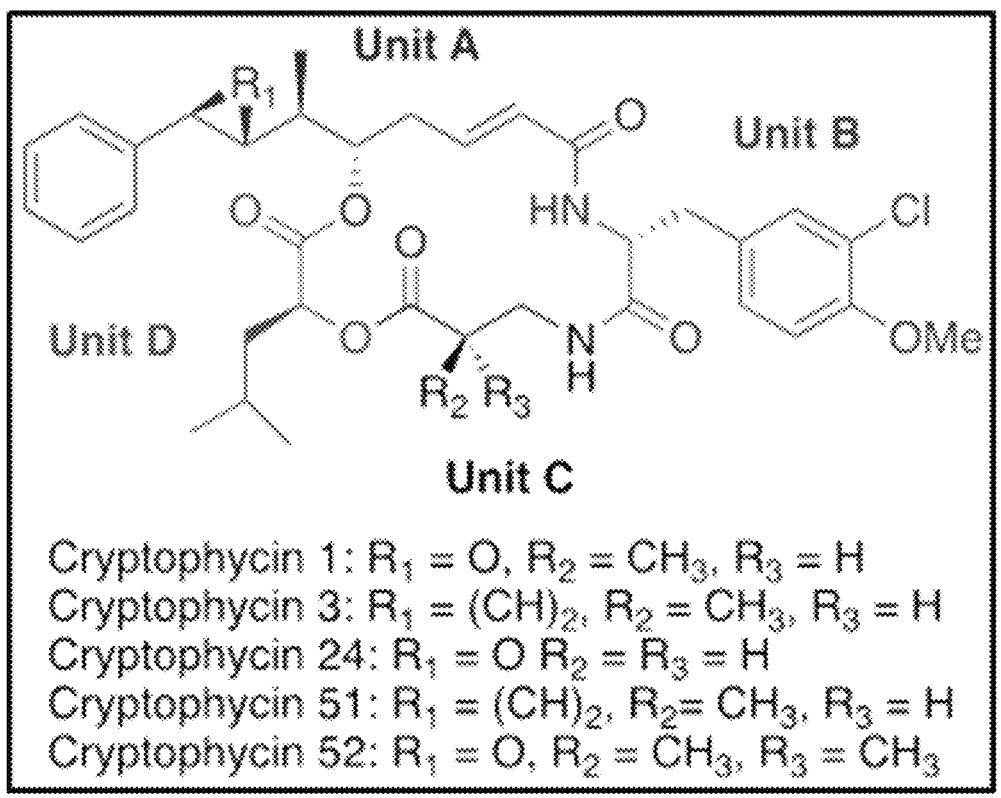
FIG. 1. The structures of select Cryptophycin analogs are presented.

The cryptophycins are a family of macrocyclic depsipeptides that display exceptionally potent antiproliferative activity against difficult-to-treat, drug-resistant cancers. Recently, these molecules have continued to attract attention as potential payloads in antibody drug conjugates, highlighting the continued need for alternative synthetic strategies as well as analogs to facilitate linking of these tubulin binders to appropriate biomolecules. Unique challenges facing the synthesis and derivatization of this complex group of molecules led us to investigate a chemoenzymatic synthesis designed to access more promising analogs.

The cryptophycin thioesterase (CrpTE) is a versatile enzyme that catalyzes macrocyclization of over twenty natural cryptophycin metabolites, allowing us to envision a drug development strategy involving its use as a stand-alone biocatalyst for the production of unnatural derivatives. To this end, we developed a scalable synthesis of 12 new unit A-B-C-D linear chain elongation intermediates containing heterocyclic aromatic groups as alternatives to the native unit A benzyl group. N-acetyl cysteamine activated forms of each intermediate were assessed for turnover to macrocyclic products using wild-type, excised CrpTE, which demonstrated the exceptional flexibility of this enzyme. Semi-preparative scale reactions were conducted for isolation, structural characterization, and further biological evaluation that revealed a des β-epoxy analog with low picomolar potency.

The work disclosed herein enabled the identification and biological evaluation of one of the most potent cryptophycin analogs produced to date, which contains a styrene functionality and obviates the need for an epoxide group to achieve low pM potency. The valuable insights regarding selectivity and specificity of CrpTE toward unnatural substrates from this study establish CrpTE as a robust and broader scope catalyst that can be employed both in a stand-alone setting and as a part of larger, enzymatic cascade for the production of biologically active molecules on a broader scale.

More specifically, the selectivity of CrpTE towards unnatural substrates was explored, based on the state of the art.[37] The cyclization-to-hydrolysis ratios observed between the native chain elongation intermediate and a substrate containing a terminal olefin indicated that the aryl ring was necessary for optimal cyclization. It remained unclear, however, if aryl rings of varying sizes and functional group substitutions would be well-tolerated.[37] This site was chosen for manipulation as it represents an under-explored area in cryptophycin structure-activity relationship studies (SAR) and is an excellent position for the use of a tactical bioisostere that could increase water solubility, leading to better in vivo efficacy as well as potentially decreased toxicity.[26, 28] Utilizing CrpTE to formulate these novel cryptophycins would thus enable generation of important new analogs, and also provide unique insights into the flexibility of the enzyme for incorporation of non-native starter units. A better understanding of the recognition factors employed in the selectivity of these enzymes would further expand our ability to design TEs with tunable substrate tolerance for use in biocatalytic platforms that aid the drug discovery process.

Disclosed herein are compounds, and uses of these compounds in treating cancer. One aspect of the present disclosure is generally related to the use of the compounds described herein or pharmaceutically acceptable salts, or pharmaceutically acceptable compositions comprising such a compound or a pharmaceutically acceptable salt thereof, for treating a cancer, such as colon, breast, leukemia, prostate, ovarian, central nervous system, or non-small cell lung cancer, in a patient.

Compounds of the Disclosure

The present disclosure provides compounds of Formula (I), or a pharmaceutically acceptable salt thereof:

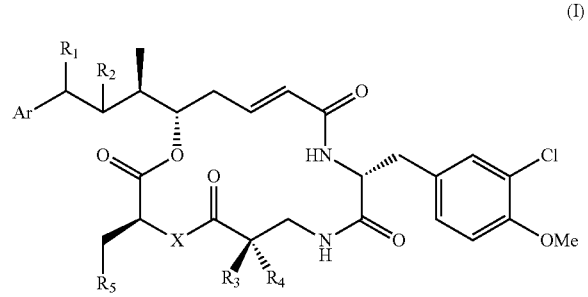

(I)

wherein

Ar is a 5-to 7-membered heterocyclic aryl group having 1 to 3 ring heteroatoms selected from N, O, and S, and is optionally substituted with 1-3 substituents independently selected from $C_{1-5}$ alkyl and L-$R_6$;

$R_1$ is chlorine, bromine, or iodine;

$R_2$ is OH or OC(O)CH$_2$NHR; or $R_1$ and $R_2$ together (1) indicate a double bond between the carbons to which they are attached or (2) form a β-epoxide ring with the carbons to which they are attached;

each of $R_3$ and $R_4$ is independently H, $C_{1-6}$alkyl, $C_{0-6}$alkylene-OH or $C_{0-6}$alkylene-NH(R); or $R_3$ and $R_4$ together with the carbon atom to which they are attached form a spiro $C_{3-5}$ cycloalkyl or a spiro 3- to 5-membered heterocycloalkyl having one nitrogen ring atom;

$R_5$ is $C_{1-6}$alkyl, $C_{0-6}$alkylene-OH or $C_{0-6}$alkylene-NH(R); and

R is H, $C_{1-6}$alkyl, or L-$R_6$;

L is a linker;

$R_6$ is a reactive chemical group; and

X is O, NH or NMe, with the proviso that the compound or salt comprises 0 or 1 L-$R_6$.

Ar is a 5-to 7-membered heterocyclic aryl group having 1 to 3 ring heteroatoms selected from N, O, and S, and is optionally substituted with 1-3 substituents independently selected from $C_{1-5}$ alkyl and L-$R_6$. As used herein, the term "heterocyclic aryl" refers to a monocyclic aromatic ring having 5 to 7 total ring atoms, and containing one to three heteroatoms selected from nitrogen, oxygen, and sulfur atom in the aromatic ring. Unless otherwise indicated, a heterocyclic aryl group can be unsubstituted or substituted with one or more, and in particular one to three, substituents. In some cases, the heterocyclic aryl group is substituted with $C_{1-5}$ salkyl or an L-$R_6$ moiety as discussed herein. Examples of heterocyclic aryl groups include, but are not limited to, thienyl, furyl, pyridyl, pyrrolyl, oxazolyl, triazinyl, triazolyl, isothiazolyl, isoxazolyl, imidazolyl, pyrazinyl, pyrimidinyl, thiazolyl, and thiadiazolyl. In some cases, the heterocyclic aryl (Ar) comprises pyridyl, pyrazinyl, imidazolyl, or oxazolyl, optionally substituted with 1-3 substituents selected from methyl and isopropyl. In some cases, Ar is substituted with L-$R_6$.

As used herein, the term "alkyl" refers to straight chained and branched saturated hydrocarbon groups containing one to thirty carbon atoms, for example, one to twenty carbon atoms, or one to ten carbon atoms. The term $C_n$ means the alkyl group has "n" carbon atoms. For example, $C_4$ alkyl refers to an alkyl group that has 4 carbon atoms. $C_1$-$C_6$ alkyl refers to an alkyl group having a number of carbon atoms encompassing the entire range (e.g., 1 to 6 carbon atoms), as well as all subgroups (e.g., 1-6, 2-5, 1-5, 3-6, 1, 2, 3, 4, 5, and 6 carbon atoms). Nonlimiting examples of alkyl groups include, methyl, ethyl, n-propyl, isopropyl, n-butyl, sec-butyl (2-methylpropyl), t-butyl (1,1-dimethylethyl), 3,3-dimethylpentyl, and 2-ethylhexyl. Unless otherwise indicated, an alkyl group can be an unsubstituted alkyl group or a substituted alkyl group.

The term "alkylene" used herein refers to an alkyl group having a substituent. For example, the term "alkylene-OH" refers to an alkyl group substituted with a hydroxy group. For example, an alkylene group can be —CH$_2$CH$_2$— or —CH$_2$—. The term $C_n$ means the alkylene group has "n" carbon atoms. For example, $C_{1-6}$ alkylene refers to an alkylene group having a number of carbon atoms encompassing the entire range, as well as all subgroups. The term $C_0$ indicates a direct bond—$C_0$alkylene-OH indicates a OH substituent. Unless otherwise indicated, an alkylene group can be an unsubstituted alkylene group or a substituted alkylene group.

As used herein, the term "cycloalkyl" refers to an aliphatic cyclic hydrocarbon group containing three to twelve carbon atoms (e.g., 3, 4, 5, 6, 7, 8, 9, 10, 11, or 12 carbon atoms). The term $C_n$ means the cycloalkyl group has "n" carbon atoms. For example, $C_5$ cycloalkyl refers to a cycloalkyl group that has 5 carbon atoms in the ring. $C_3$-$C_6$ cycloalkyl refers to cycloalkyl groups having a number of carbon atoms encompassing the entire range (e.g., 3 to 5 carbon atoms), as well as all subgroups (e.g., 3-4 4-5, 2, 4, and 5 carbon atoms). Nonlimiting examples of cycloalkyl groups include cyclopropyl, cyclobutyl, cyclopentyl, cyclohexyl, cycloheptyl, and cyclooctyl. Unless otherwise indicated, a cycloalkyl group can be an unsubstituted cycloalkyl group or a substituted cycloalkyl group. The cycloalkyl groups described herein can be isolated, a spiro ring, or fused to another cycloalkyl group, a heterocycloalkyl group, an aryl group and/or a heteroaryl group. When a cycloalkyl group is fused to another cycloalkyl group, then each of the cycloalkyl groups can contain three to twelve carbon atoms unless specified otherwise. Unless otherwise indicated, a cycloalkyl group can be unsubstituted or substituted.

As used herein, the term "heterocycloalkyl" is defined similarly as cycloalkyl, except the ring contains one to three heteroatoms independently selected from oxygen, nitrogen, and sulfur. In particular, the term "heterocycloalkyl" refers to a ring containing a total of three to ten atoms (e.g., three to five, or five to ten), of which 1, 2, 3 or three of those atoms are heteroatoms independently selected from the group consisting of oxygen, nitrogen, and sulfur, and the remaining atoms in the ring are carbon atoms. In some cases, the heterocycloalkyl is a spiro 3 to 5 membered ring having one nitrogen ring atom. Nonlimiting examples of heterocycloalkyl groups include azetidine, aziridine, pyrrolidine, piperdine, pyrazolidine, tetrahydrofuran, tetrahydropyran, dihydrofuran, morpholine, and the like. In some cases, the heterocycloalkyl comprises azetidine, aziridine, or pyrrolidine. The heterocycloalkyl can be substituted or unsubstituted.

As used herein, the term "substituted," when used to modify a chemical functional group, refers to the replacement of at least one hydrogen radical on the functional group with a substituent. Substituents can include, but are not limited to, alkyl, cycloalkyl, alkenyl, cycloalkenyl, alkynyl, heterocycloalkyl, aryl, heteroaryl, hydroxyl, oxy, alkoxy, heteroalkoxy, ester, thioester, carboxy, cyano, nitro, amino, amido, acetamide, and halo (e.g., fluoro, chloro, bromo, or iodo). When a chemical functional group includes more than one substituent, the substituents can be bound to the same carbon atom or to two or more different carbon atoms.

As used herein, the term "linker" refers to a moiety that links two portions of a molecule (e.g., compounds described herein and salts thereof). Non-limiting examples of linkers include peptides having 1 to 10 amino acids, polyethylene glycols having 1 to 15 ethylene glycol monomers, and a β-glucuronic acids. In some cases, L comprises a peptide having 1 to 10 amino acids. In some cases, the amino acids are selected from the group consisting of alanine (Ala), Citrulline (Cit), Glutamine (Gln), glycine (Gly), lysine (Lys), acetyl-lysine (AcLys), proline (Pro), phenylalanine (Phe), and Valine (Val). In some cases, L comprises a polyethylene glycol having 1 to 15 (e.g., 5 to 15, 3 to 10, 3 to 15, 5 to 10) ethylene glycol monomers. In some cases, L comprises a p-glucuronic acid. In some cases, the p-glucuronic acid comprises a furanose. In some cases, the p-glucuronic acid comprises a pyranose.

In some cases, L has a structure $R_6$ comprises a N-hydroxysuccinimide ester. In some cases, $R_6$ comprises an O-alkyl hydroxylamine.

In some cases, (1) Ar is

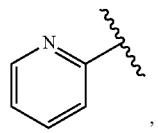

$R_3$ is $CH_3$, and $R_4$ is H; (2) Ar is

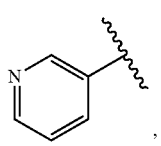

$R_3$ is $CH_3$, and $R_4$ is H or $CH_3$; (3) Ar is

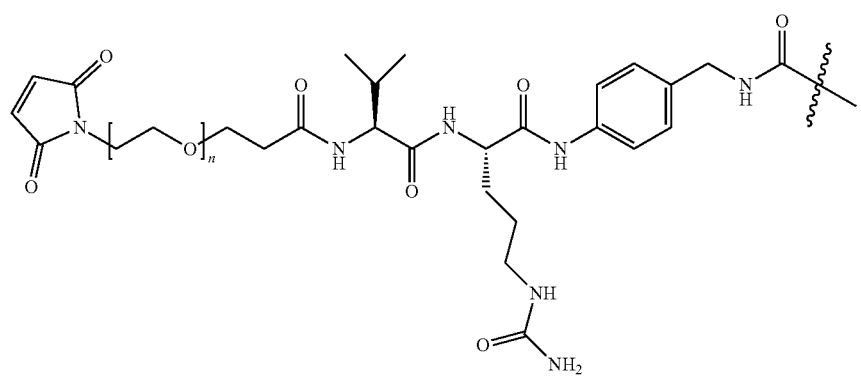

In some cases, L is attached to the compound of formula (I) via a single (i.e., direct covalent) bond, an ester bond, an amide bond, a sulfide bond, a disulfide bond, a para-amino benzyl (PAB) group, or via a para-amino benzyloxycarbonyl (PABC) group. In some cases, L is attached via a single bond. In some cases, L is attached via an ester bond. In some cases, L is attached via an amide bond. In some cases, L is attached via a para-amino benzyl (PAB) group.

As used herein, the term "reactive chemical group" refers to a chemical functional group that can react with another, complementary, functional group to form a covalent bond. The reactive group can be an amine such that in the presence of a complementary functional group (e.g., carboxylic acid, acyl chloride, or the like), an amide functional group can form. Some specific, non-limiting, examples of reactive chemical groups are maleimido groups, maleimidocaproyl groups, maleimido PEG groups, bromoacetamide groups, N-hydroxysuccinimide esters, and O-alkyl hydroxylamines. In some cases, $R_6$ comprises a maleimido group. In some cases, $R_6$ comprises a maleimidocaproyl group. In some cases, $R_6$ comprises a maleimido PEG group. In some cases, $R_3$ is $CH_3$, and $R_4$ is H or $CH_3$; (3) Ar is

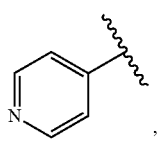

$R_3$ is $CH_3$, and $R_4$ is H or $CH_3$; (4) Ar is

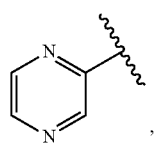

R₃ is CH₃, and R₄ is H; (5) Ar is

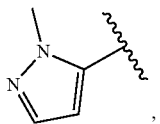
,

R₃ is CH₃, and R₄ is H; (6) Ar is

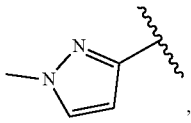
,

R₃ is CH₃, and R₄ is H; (7) Ar is

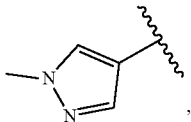
,

R₃ is CH₃, and R₄ is H or CH₃; (8) Ar is

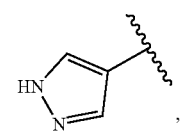
,

R₃ is CH₃, and R₄ is H or CH₃; (9) Ar is

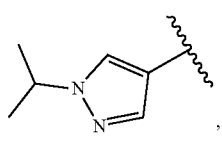
,

R₃ is CH₃, and R₄ is H; or (10) Ar is

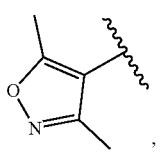 [SMILES: *c1c(C)noc1C]
,

R₃ is CH₃, and R₄ is H. In some cases, Ar is

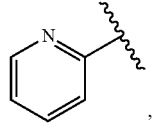 [SMILES: *c1ccccn1]
,

R₃ is CH₃, and R₄ is H. In some cases, Ar is

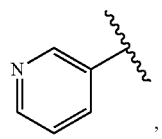
,

R₃ is CH₃, and R₄ is H or CH₃. In some cases, Ar is

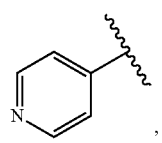
,

R₃ is CH₃, and R₄ is H or CH₃. In some cases, Ar is

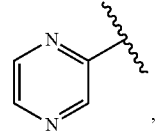
,

R₃ is CH₃, and R₄ is H. In some cases, Ar is

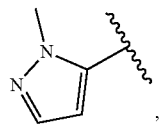
,

R₃ is CH₃, and R₄ is H. In some cases, Ar is

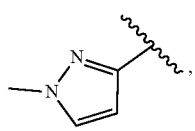 [SMILES: *c1ccn(C)n1]
,

R₃ is CH₃, and R₄ is H. In some cases, Ar is

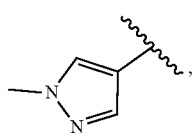 [SMILES: *c1cnn(C)c1]
,

R₃ is CH₃, and R₄ is H or CH₃. In some cases, Ar is

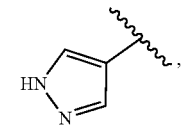
, $R_3$ is $CH_3$, and $R_4$ is H or $CH_3$. In some cases, Ar is

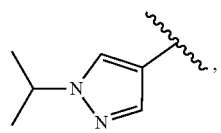 [SMILES: *c1cnn(C(C)C)c1]

$R_3$ is $CH_3$, and $R_4$ is H. In some cases, Ar is

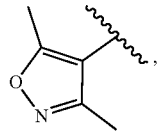

$R_3$ is $CH_3$, and $R_4$ is H.

In some cases, $R_1$ and $R_2$ together indicate a double bond between the carbons to which they are attached. In some cases, $R_1$ and $R_2$ together form a β-epoxide ring with the carbons to which they are attached. In some cases, $R_1$ is Cl and $R_2$ is OH. In some cases, $R_1$ is Cl and $R_2$ is OC(O)CH$_2$NH$_2$.

In some cases, (1) Ar is

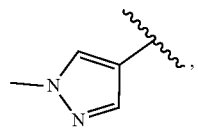 [SMILES: *c1cnn(C)c1]

$R_3$ is $CH_3$, $R_4$ is H or $CH_3$, and $R_5$ is $CH(CH_3)_2$; (2) Ar is

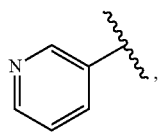 [SMILES: *c1cccnc1]

$R_3$ is $CH_3$, $R_4$ is H or $CH_3$, and $R_5$ is $CH(CH_3)_2$; or (3) Ar is

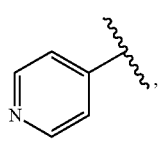 [SMILES: *c1ccncc1]

$R_3$ is $CH_3$, $R_4$ is H or $CH_3$, and $R_5$ is $CH(CH_3)_2$. In some cases, Ar is

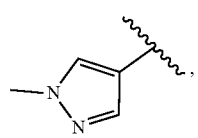

$R_3$ is $CH_3$, $R_4$ is H or $CH_3$, and $R_5$ is $CH(CH_3)_2$. In some cases, Ar is

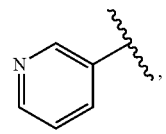

$R_3$ is $CH_3$, $R_4$ is H or $CH_3$, and $R_5$ is $CH(CH_3)_2$. In some cases, Ar is

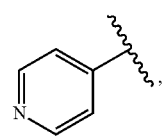

$R_3$ is $CH_3$, $R_4$ is H or $CH_3$, and $R_5$ is $CH(CH_3)_2$.

In some cases, $R_3$ is $NH_2$, NHMe, $CH_2$—$NH_2$, or $CH_2$—NHMe. In some cases, $R_3$ is $NH_2$. In some cases, $R_3$ is NHMe. In some cases, $R_3$ is $CH_2$—$NH_2$. In some cases, $R_3$ is $CH_2$—NHMe. In some cases, $R_3$ is OH or $CH_2$-OH. In some cases, $R_3$ is OH. In some cases, $R_3$ is $CH_2$—OH.

In some cases, $R_5$ is $NH_2$, NHMe, (CH)CH$_3$NH$_2$, or (CH)CH$_3$NHMe. In some cases, $R_5$ is $NH_2$. In some cases, $R_5$ is NHMe. In some cases, $R_5$ is (CH)CH$_3$NH$_2$. In some cases, $R_5$ is (CH)CH$_3$NHMe.

In some cases, X is O. In some cases, X is NH or NMe. In some cases, X is NH. In some cases, X is NMe.

In some cases, the compound is selected from the group consisting of

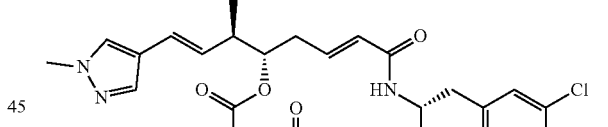

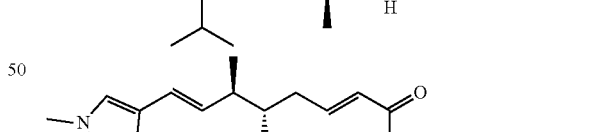

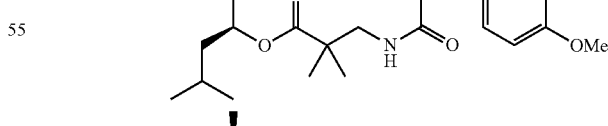

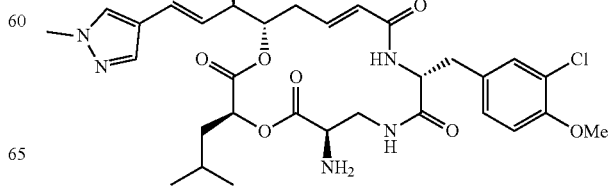

15
-continued
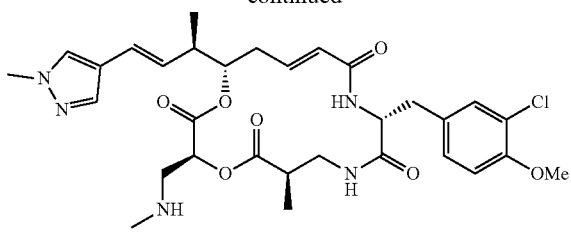
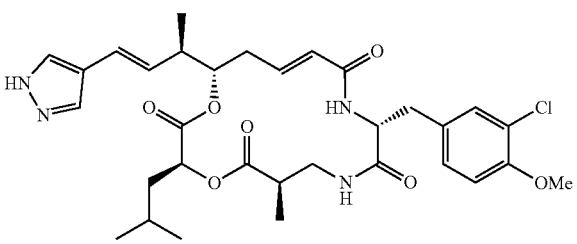
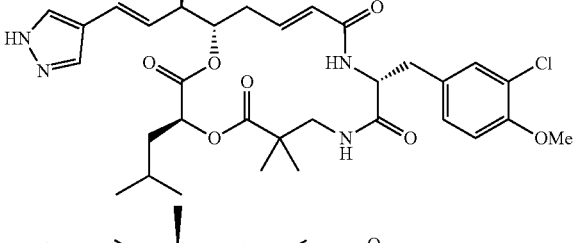
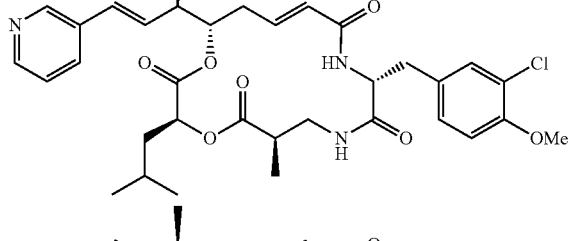
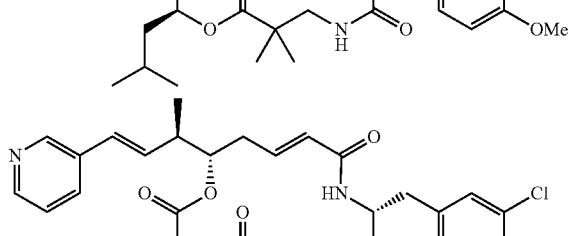
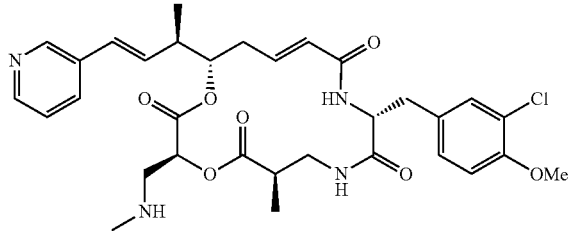
16
-continued
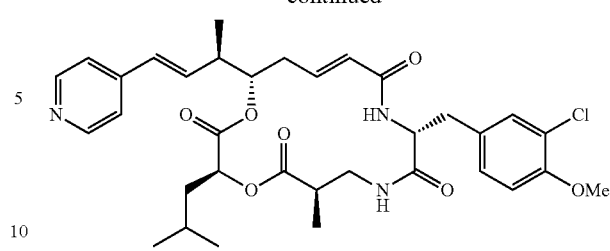
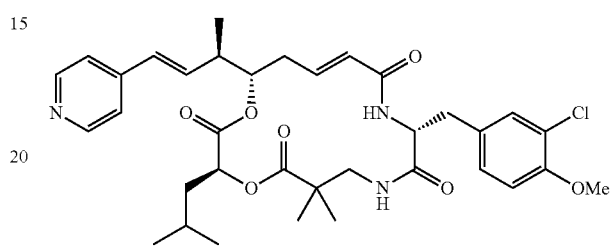
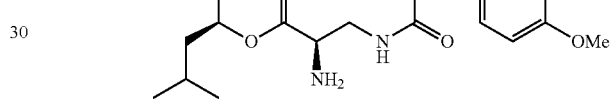
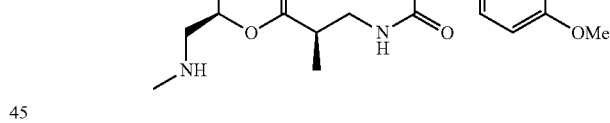
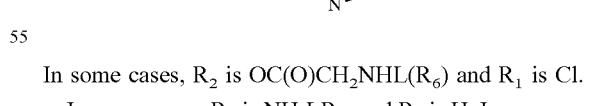
In some cases, Ar is
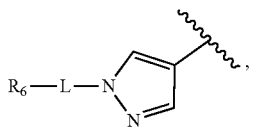
In some cases, $R_2$ is $OC(O)CH_2NHL(R_6)$ and $R_1$ is Cl.
In some cases, $R_3$ is $NH-LR_6$, and $R_4$ is H. In some cases, (1) Ar is
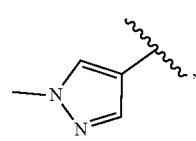 [SMILES: *c1cnn(C)c1]

$R_1$ and $R_2$ together indicate a double bond or a β-epoxide, and $R_5$ is $CH(CH_3)_2$; (2) Ar is

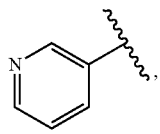 [SMILES: *c1cccnc1]

$R_1$ and $R_2$ together indicate a double bond or a β-epoxide, and $R_5$ is $CH(CH_3)_2$; or (3) Ar is

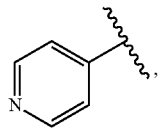 [SMILES: *c1ccncc1]

$R_1$ and $R_2$ together indicate a double bond or a β-epoxide, and $R_5$ is $CH(CH_3)_2$, $CH(CH_3)_2$. In some cases, Ar is

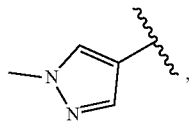 [SMILES: *c1cnn(C)c1]

$R_1$ and $R_2$ together indicate a double bond or a β-epoxide, and $R_5$ is $CH(CH_3)_2$. In some cases, Ar is

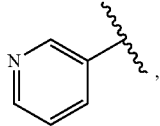 [SMILES: *c1cccnc1]

$R_1$ and $R_2$ together indicate a double bond or a β-epoxide, and $R_5$ is $CH(CH_3)_2$. In some cases, Ar is

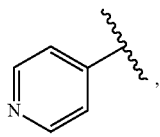

$R_1$ and $R_2$ together indicate a double bond or a β-epoxide, and $R_5$ is $CH(CH_3)_2$, $CH(CH_3)_2$.

In some cases, $R_5$ is $NH-LR_6$. In some cases, (1) Ar is

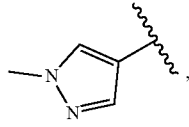 [SMILES: *c1cnn(C)c1]

$R_1$ and $R_2$ together indicate a double bond or a β-epoxide, $R_3$ is $CH_3$, and $R_4$ is H or $CH_3$; (2) Ar is

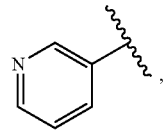

$R_1$ and $R_2$ together indicate a double bond or a β-epoxide, $R_3$ is $CH_3$, and $R_4$ is H or $CH_3$; or (3) Ar is

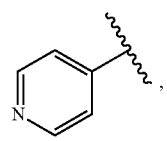

$R_1$ and $R_2$ together indicate a double bond or a β-epoxide, $R_3$ is $CH_3$, and $R_4$ is H or $CH_3$. In some cases, Ar is

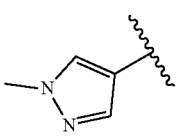

$R_1$ and $R_2$ together indicate a double bond or a β-epoxide, $R_3$ is $CH_3$, and $R_4$ is H or $CH_3$. In some cases, Ar is

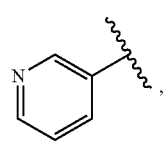

$R_1$ and $R_2$ together indicate a double bond or a β-epoxide, $R_3$ is $CH_3$, and $R_4$ is H or $CH_3$. In some cases, Ar is

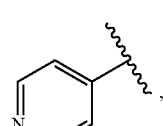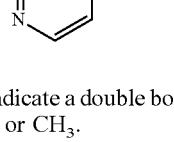

$R_1$ and $R_2$ together indicate a double bond or a β-epoxide, $R_3$ is $CH_3$, and $R_4$ is H or $CH_3$.

The compounds disclosed herein can be in the form of a pharmaceutically acceptable salt. As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al. describe pharmaceutically acceptable salts in detail in *J. Pharmaceutical Sciences*, 1977, 66, 1-19, which is incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, trifluoroacetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, glutamate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts of compounds containing a carboxylic acid or other acidic functional group can be prepared by reacting with a suitable base. Such salts include, but are not limited to, alkali metal, alkaline earth metal, aluminum salts, ammonium, $N^+(C_{1-4}alkyl)_4$ salts, and salts of organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, dehydroabietylamine, N,N'-bis-dehydroabietylamine, glucamine, N-methylglucamine, collidine, quinine, quinoline, and basic amino acids such as lysine and arginine. This invention also envisions the quaternization of any basic nitrogen-containing groups of the compounds disclosed herein. Water or oil-soluble or dispersible products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

Also provided herein are conjugates comprising a compound or salt described herein and a peptide, a protein, or an antibody. In some cases, the conjugates comprise a compound or salt described herein and an antibody. In some cases, the antibody and the compound or salt are covalently attached via the reactive chemical group of the compound or salt and a complementary reactive group on the antibody. In some cases, the complementary reactive group on the antibody comprises an amine. In some cases, the amine is an &amine of a lysine on the antibody.

In some cases, the antibody is a monocolonal antibody or a nanobody. In some cases, the antibody is a monoclonal antibody. In some cases, the antibody is a nanobody. In some cases, the monocolonal antibody is brentuximab, cetuximab, gemtuzumab, panitumumab, ofatumumab, rituximab, or trastuzumab. In some cases, the nanobody is a single domain antibody or a camelid antibody.

Synthesis of Compounds of the Disclosure

The compounds disclosed herein can be prepared in a variety of ways using commercially available starting materials, compounds known in the literature, or from readily prepared intermediates, by employing standard synthetic methods and procedures either known to those skilled in the art, or in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., March's Advanced Organic Chemistry: Reactions, Mechanisms, and Structure, 5$^{th}$ edition, John Wiley & Sons: New York, 2001; and Greene, T. W., Wuts, P. G. M., Protective Groups in Organic Synthesis, 3$^{rd}$ edition, John Wiley & Sons: New York, 1999, are useful and recognized reference textbooks of organic synthesis known to those in the art. For example, the compounds disclosed herein can be synthesized by solid phase synthesis techniques including those described in Merrifield, J. Am. Chem. Soc. 1963; 85:2149; Davis et al., Biochem. Intl. 1985; 10:394-414; Larsen et al., J. Am. Chem. Soc. 1993; 115:6247; Smith et al., J. Peptide Protein Res. 1994; 44: 183; O'Donnell et al., J. Am. Chem. Soc. 1996; 118:6070; Stewart and Young, Solid Phase Peptide Synthesis—Freeman (1969); Finn et al., The Proteins, 3rd ed., vol. 2, pp. 105-253 (1976); and Erickson et al., The Proteins, 3rd ed., vol. 2, pp. 257-527 (1976). The following descriptions of synthetic methods are designed to illustrate, but not to limit, general procedures for the preparation of compounds of the present disclosure.

The synthetic processes disclosed herein can tolerate a wide variety of functional groups; therefore, various substituted starting materials can be used. The processes generally provide the desired final compound at or near the end of the overall process, although it may be desirable in certain instances to further convert the compound to a pharmaceutically acceptable salt, ester or prodrug thereof.

Also provided are methods of producing the compound or salt described herein comprising contacting a seco cryptophycin intermediate with a cryptophycin thioesterase under conditions suitable for macrocyclization to form the compound or salt. In some cases, wherein the macrocyclization is macrolactonization.

In some cases, the cryptophycin thioesterase is derived from a polyketide synthase protein complex, a non-ribosomal protein synthetase protein complex, or a hybrid polyketide synthase/non-ribosomal peptide synthetase protein complex. In some cases, the cryptophycin thioesterase is derived from a hybrid polyketide synthase/non-ribosomal peptide synthetase protein complex.

In some cases, the method further comprises contacting the seco cryptophycin with a cryptophycin P450 to form a β epoxide ring between $R_1$, $R_2$, and the carbons to which they are attached. In some cases, the cryptophycin P450 is cryptophycin epoxidase.

Pharmaceutical Compositions, Dosing, and Routes of Administration

Further provided are pharmaceutical compositions (sometimes referred to as formulations, interchangeably, herein) comprising a compound as described herein (e.g., compounds of Formula I or pharmaceutically acceptable salts of the compounds) and a pharmaceutically acceptable excipient. As used herein, the term "pharmaceutically acceptable" means that the referenced substance, such as a compound of the present disclosure, or a composition containing the compound, or a particular excipient, are safe and suitable for administration to a patient or subject. The term "pharmaceutically acceptable excipient" refers to a medium that does not interfere with the effectiveness of the biological activity of the active ingredient(s) and is not toxic to the host to which it is administered. An excipient can be any pharmaceutically acceptable additive, carrier, diluent, adjuvant, or other ingredient, other than the active pharmaceutical ingredient (API).

The compounds described herein can be administered to a subject in a therapeutically effective amount (e.g., in an amount sufficient to prevent or relieve the symptoms of cancer). The compounds can be administered alone or as part of a pharmaceutically acceptable composition or formulation. In addition, the compounds can be administered all at once, multiple times, or delivered substantially uniformly over a period of time. It is also noted that the dose of the compound can be varied over time.

A particular administration regimen for a particular subject will depend, in part, upon the compound, the amount of compound administered, the route of administration, and the cause and extent of any side effects. The amount of compound administered to a subject (e.g., a mammal, such as a human) in accordance with the disclosure should be sufficient to effect the desired response over a reasonable time frame. A "therapeutically effective amount" means an amount of a compound or combination of therapeutically active compounds (e.g., compounds and salts thereof described herein) that ameliorates, attenuates or eliminates one or more symptoms of a particular disease or condition (e.g., cancer), or prevents or delays the onset of one of more symptoms of a particular disease or condition. Dosage typically depends upon the route, timing, and frequency of administration. Accordingly, the clinician titers the dosage and modifies the route of administration to obtain the optimal therapeutic effect, and conventional range-finding techniques are known to those of ordinary skill in the art.

Purely by way of illustration, the method comprises administering, e.g., from about 0.1 mg/kg up to about 100 mg/kg of compound or more, depending on the factors mentioned above. In other embodiments, the dosage ranges from 1 mg/kg up to about 100 mg/kg; or 5 mg/kg up to about 100 mg/kg; or 10 mg/kg up to about 100 mg/kg. Some conditions require prolonged treatment, which may or may not entail administering lower doses of compound over multiple administrations. If desired, a dose of the compound is administered as two, three, four, five, six or more subdoses administered separately at appropriate intervals throughout the day, optionally, in unit dosage forms. The treatment period will depend on the particular condition of the patient and type of disease, and may last one day to several months.

Suitable methods of administering a physiologically-acceptable composition, such as a pharmaceutical composition comprising the compounds disclosed herein (e.g., compounds of Formula I), are well known in the art. Although more than one route can be used to administer a compound, a particular route can provide a more immediate and more effective reaction than another route. Depending on the circumstances, a pharmaceutical composition comprising the compound is applied or instilled into body cavities, absorbed through the skin or mucous membranes, ingested, inhaled, and/or introduced into circulation. For example, in certain circumstances, it will be desirable to deliver a pharmaceutical composition comprising the agent orally, through injection by intravenous, intraperitoneal, intracerebral (intra-parenchymal), intracerebroventricular, intramuscular, intra-ocular, intraarterial, intraportal, intralesional, intramedullary, intrathecal, intraventricular, transdermal, subcutaneous, intraperitoneal, intranasal, enteral, topical, sublingual, urethral, vaginal, or rectal means, by sustained release systems, or by implantation devices. If desired, the compound is administered regionally via intrathecal administration, intracerebral (intra-parenchymal) administration, intracerebroventricular administration, or intraarterial or intravenous administration feeding the region of interest. Alternatively, the composition is administered locally via implantation of a membrane, sponge, or another appropriate material onto which the desired compound has been absorbed or encapsulated. Where an implantation device is used, the device is, in one aspect, implanted into any suitable tissue or organ, and delivery of the desired compound is, for example, via diffusion, timed-release bolus, or continuous administration.

To facilitate administration, the compound is, in various aspects, formulated into a physiologically-acceptable composition comprising a carrier (e.g., vehicle, adjuvant, or diluent). The particular carrier employed is limited only by chemico-physical considerations, such as solubility and lack of reactivity with the compound, and by the route of administration. Physiologically-acceptable carriers are well known in the art. Illustrative pharmaceutical forms suitable for injectable use include sterile aqueous solutions or dispersions and sterile powders for the extemporaneous preparation of sterile injectable solutions or dispersions (for example, see U.S. Pat. No. 5,466,468). Injectable formulations are further described in, e.g., Pharmaceutics and Pharmacy Practice, J. B. Lippincott Co., Philadelphia. Pa., Banker and Chalmers, eds., pages 238-250 (1982), and ASHP Handbook on Injectable Drugs, Toissel, 4th ed., pages 622-630 (1986)). A pharmaceutical composition comprising the compound is, in one aspect, placed within containers, along with packaging material that provides instructions regarding the use of such pharmaceutical compositions. Generally, such instructions include a tangible expression describing the reagent concentration, as well as, in certain embodiments, relative amounts of excipient ingredients or diluents (e.g., water, saline or PBS) that may be necessary to reconstitute the pharmaceutical composition.

Compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Microorganism contamination can be prevented by adding various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents delaying absorption, for example, aluminum monostearate and gelatin.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, and silicic acid; (b) binders, as for example, carboxymethylcellulose, alginates, gelatin, polyvinylpyrrolidone, sucrose, and acacia;

(c) humectants, as for example, glycerol; (d) disintegrating agents, as for example, agar-agar, calcium carbonate, potato or tapioca starch, alginic acid, certain complex silicates, and sodium carbonate; (a) solution retarders, as for example, paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, and tablets, the dosage forms may also comprise buffering agents. Solid compositions of a similar type may also be used as fillers in soft and hard filled gelatin capsules using such excipients as lactose or milk sugar, as well as high molecular weight polyethylene glycols, and the like.

Solid dosage forms such as tablets, dragees, capsules, pills, and granules can be prepared with coatings and shells, such as enteric coatings and others well known in the art. The solid dosage forms may also contain opacifying agents. Further, the solid dosage forms may be embedding compositions, such that they release the active compound or compounds in a certain part of the intestinal tract in a delayed manner. Examples of embedding compositions that can be used are polymeric substances and waxes. The active compound can also be in micro-encapsulated form, optionally with one or more excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and sesame seed oil, glycerol, tetrahydrofurfuryl alcohol, polyethylene glycols and fatty acid esters of sorbitan, or mixtures of these substances, and the like.

Besides such inert diluents, the composition can also include adjuvants, such as wetting agents, emulsifying and suspending agents, sweetening, flavoring, and perfuming agents. Suspensions, in addition to the active compound, may contain suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal administration are preferably suppositories, which can be prepared by mixing the compounds of the disclosure with suitable non-irritating excipients or carriers such as cocoa butter, polyethylene glycol or a suppository wax, which are solid at ordinary room temperature, but liquid at body temperature, and therefore, melt in the rectum or vaginal cavity and release the active component.

The compositions used in the methods of the invention may be formulated in micelles or liposomes. Such formulations include sterically stabilized micelles or liposomes and sterically stabilized mixed micelles or liposomes. Such formulations can facilitate intracellular delivery, since lipid bilayers of liposomes and micelles are known to fuse with the plasma membrane of cells and deliver entrapped contents into the intracellular compartment.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration.

The frequency of dosing will depend on the pharmacokinetic parameters of the agents and the routes of administration. The optimal pharmaceutical formulation will be determined by one of skill in the art depending on the route of administration and the desired dosage. See, for example, Remington's Pharmaceutical Sciences, 18th Ed. (1990) Mack Publishing Co., Easton, Pa., pages 1435-1712, incorporated herein by reference. Such formulations may influence the physical state, stability, rate of in vivo release and rate of in vivo clearance of the administered agents. Depending on the route of administration, a suitable dose may be calculated according to body weight, body surface areas or organ size. Further refinement of the calculations necessary to determine the appropriate treatment dose is routinely made by those of ordinary skill in the art without undue experimentation, especially in light of the dosage information and assays disclosed herein, as well as the pharmacokinetic data observed in animals or human clinical trials.

The precise dosage to be employed depends upon several factors including the host, whether in veterinary medicine or human medicine, the nature and severity of the condition, e.g., disease or disorder, being treated, the mode of administration and the particular active substance employed. The compounds may be administered by any conventional route, in particular enterally, and, in one aspect, orally in the form of tablets or capsules. Administered compounds can be in the free form or pharmaceutically acceptable salt form as appropriate, for use as a pharmaceutical, particularly for use in the prophylactic or curative treatment of a disease of interest. These measures will slow the rate of progress of the disease state and assist the body in reversing the process direction in a natural manner.

It will be appreciated that the pharmaceutical compositions and treatment methods of the invention are useful in fields of human medicine and veterinary medicine. Thus the subject to be treated is in one aspect a mammal. In another aspect, the mammal is a human.

In jurisdictions that forbid the patenting of methods that are practiced on the human body, the meaning of "administering" of a composition to a human subject shall be restricted to prescribing a controlled substance that a human subject will self-administer by any technique (e.g., orally, inhalation, topical application, injection, insertion, etc.). The broadest reasonable interpretation that is consistent with laws or regulations defining patentable subject matter is intended. In jurisdictions that do not forbid the patenting of methods that are practiced on the human body, the "administering" of compositions includes both methods practiced on the human body and also the foregoing activities.

Methods of Use

The compounds described herein (e.g., the compounds of Formula I and their conjugates) can be used in the treatment of cancer. As used herein the terms "treating", "treat" or "treatment" and the like include preventative (e.g., prophylactic) and palliative treatment. The compounds disclosed herein are particularly advantageous for the treatment of difficult-to-treat or drug-resistant cancers. Non-limiting examples of cancers which the compounds described herein are useful for treating include colon, breast, leukemia, prostate, ovarian, central nervous system, or non-small cell lung cancer.

In some cases, the cancer is colon cancer. In some cases, the cancer is breast cancer. In some cases, the cancer is leukemia. In some cases, the cancer is prostate cancer. In some cases, the cancer is ovarian cancer. In some cases, the cancer is central nervous system cancer. In some cases, the cancer is brain cancer. In some cases, the cancer is lung cancer. In some cases, the cancer is non-small cell lung cancer.

The compounds described herein can be used to decrease or prevent cancer in human subjects with e.g., ovarian cancer. In a particular example, a compound or mixture is administered orally, such as by mixing with distilled water. In another example, a test compound or mixture is administered intravenously, such as in saline or distilled water. In some examples, treatment with test compound may be a single dose or repeated doses. The test compound may be administered about every 6 hours, about every 12 hours, about every 24 hours (daily), about every 48 hours, about every 72 hours, or about weekly. Treatment with repeated doses may continue for a period of time, for example for about 1 week to 12 months, such as about 1 week to about 6 months, or about 2 weeks to about 3 months, or about 1 to 2 months. Administration of a compound may also continue indefinitely. Doses of test compound are from about 0.1 mg/kg to about 400 mg/kg, such as about 1 mg/kg to about 300 mg/kg, about 2 mg/kg to about 200 mg/kg, about 10 mg/kg to about 100 mg/kg, about 20 mg/kg to about 75 mg/kg, or about 25 mg/kg to about 50 mg/kg.

The methods for assessing the effectiveness of test compounds for treating such diseases in cells, appropriate animal models, or affected subjects are known to one of skill in the art. As used herein, the terms "patient" and "subject" may be used interchangeably and mean animals, such as dogs, cats, cows, horses, and sheep (e.g., non-human animals) and humans. Particular patients or subjects are mammals (e.g., humans). The terms patient and subject include males and females.

Uses of the compounds disclosed herein in the preparation of a medicament for treating cancer also are provided herein.

EXAMPLES

The disclosure herein will be understood more readily by reference to the examples, below.

Example 1

Materials and Methods

Unless otherwise noted, chemical reagents and solvents were purchased from EMD Millipore, Sigma-Aldrich, Oakwood, Combi blocks, Chem impex, and Thermo-Fisher Scientific. Kanamycin sulfate and isopropyl-β-D-thiogalactopyranoside (IPTG) were obtained from Gold Biotechnology. Lysozyme was purchased from RPI. Imidazole was purchased from AK Scientific. Amicon Ultra centrifugal filters used for protein concentration were purchased from GE Healthcare.

Deionized water was obtained from a Milli-Q system (EMD Milipore) using Q-Gard 2/Quantum Ex Ultrapure organex cartridges. Media components for *E. coli* growth were purchased from EMD Milipore, Sigma-Aldrich, and Thermo-Fisher Scientific. Glycerol was purchased from BDH via VWR. LB broth and LB agar (Miller) were purchased in pre-made granulated form from EMD Milipore. TB broth was made from individually purchased components and consisted of 4% v/v glycerol. Media and solutions were autoclaved or sterile-filtered before use. For all solutions, pH was monitored using a VWR symphony SB 70 P pH meter calibrated according to the manufacturer's specifications.

Chemically competent *E. coli* B121 (DE3) were used for over-expression of protein. These cells were prepared according to the instructions provided with the MixandGo buffer kit purchased from Zymo Research. Optical density ($OD_{600}$) was measured using an Eppendorf BioPhotometer.

Unless otherwise noted, all reactions were performed in flame-dried glassware under an atmosphere of dry nitrogen. Reactions run at elevated temperatures were controlled by IKA RET control visc (model RS 232 C), reactions run at room temperature (rt), which was about 21-23° C., reactions run cooler than room temperature were performed in an ice bath (0° C.), dry ice/acetone (−78° C.), or isopropanol/ThermoNESLAB (model CC100) for extended times and/or at other temperatures. Commercially available starting materials and reagents were used as received unless otherwise noted. Dichloromethane was purchased as HPLC grade from Fisher and used directly. Tetrahydrofuran, N,N Dimethylformamide, and pyridine were purchased in anhydrous and unstabilized form (EMD Millipore DriSolv). Acetone was dried over $Na_2SO_4$ prior to use in reactions. Diisopropylamine and trimethylamine were distilled from calcium hydride directly prior to use.

$^1$H NMR spectra were recorded on either a Varian 600 NMR System (600 MHz) or Varian 400-MR (400 MHz) spectrometer. Chemical shifts have been reported in parts per million (ppm) using the solvent resonance as an internal standard ($CDCl_3$ 7.26 and $CD_3OD$ 3.31 ppm). Data are reported as follows: chemical shift, multiplicity (s=singlet, d=doublet, t=triplet, q=quartet, p=pentet, h=hextet), coupling constant (Hz), and integration. Proton decoupled $^{13}$C NMR spectra were recorded on a Varian 600 NMR System (150 MHz) or Varian 400-MR (100 MHz) spectrometer. Chemical shifts have been reported in ppm using relative to residual solvent peaks ($CDCl_3$, 77.0 ppm or $CD_3OD$ 49.0). High resolution mass spectra were obtained on an Agilent Technologies 6500 or 6545 Q-TOF LC/MS. Analytical reactions were assessed by an Agilent 1290 infinity II HPLC module (monitoring at 254 nM) coupled to a 6230 TOF LC/MS.

Analytical Thin layer chromatography was performed on EMD Millipore 0.25 mm silica gel $F_{254}$ plates. Visualization was accomplished by a combination of 254 nm UV lamp and either potassium permanganate ($KMNO_4$), ceric ammonium molybdate (CAM), or p-anisaldehyde. Purifications were performed by forced-air flash chromatography using EMD Millipore Silica Gel 60 (40-63 um) or a Biotage Isolera one-flash purification system. Columns used with Biotage Isolera one purification system include Biotage SNAP Ultra, SiliaSep, SiliaSepHP, and SiliaSep amine cartridges.

Example 2

Chemical Syntheses
1. Unit A Synthesis

Figure 3:
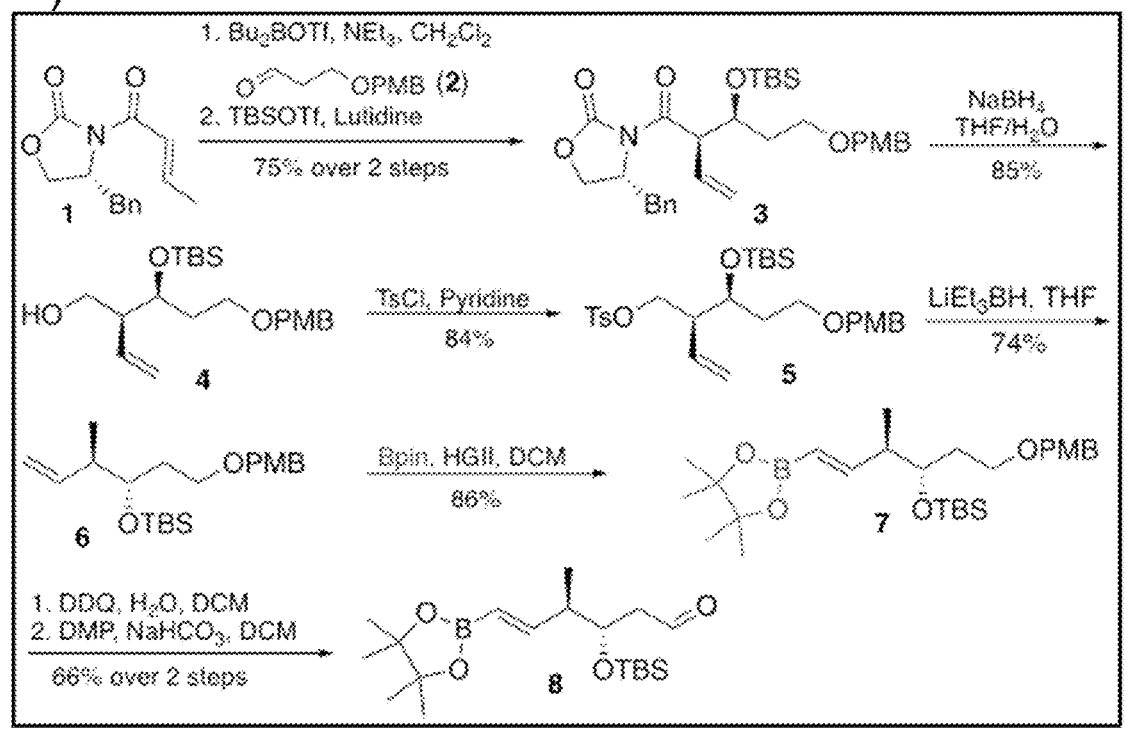
FIG. 3. A) A schematic illustration of the synthesis of a unit A fragment. B) Unit A two-step synthesis reaction is schematically shown.
Figure 3:
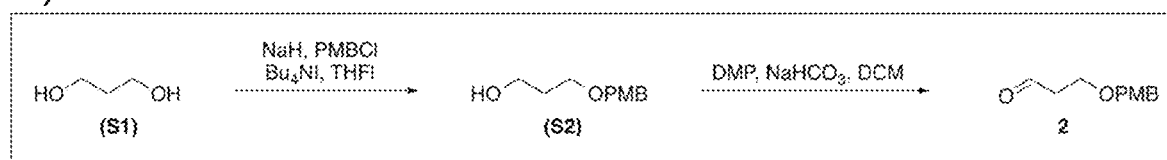

Compound 2 was synthesized over two steps from commercially available S1, as shown in FIG. 3B. All spectra were in accordance with previous literature reports.[1,2]

(R)-4-benzyl-3-((2R, 3S)-3-hydroxy-5-((4-methoxybenzyl)oxy)-2vinylpentanoyl)oxazolidin-2-one (S3).

To a three neck flask with an internal temperature probe was added a solution of 1 (7.502 g, 30.58 mmol, 1 eq) in CH$_2$Cl$_2$ (305 mL, 0.1 M) and cooled to −78° C. This was treated with dibutylboron trifluoromethanesulfonate (1 M in DCM, 33.64 mL, 33.64 mmol, 1.1 eq), and Et$_3$N (6.02 mL, 42.8 mmol, 1.4 eq). After 1 hour at −78° C., the reaction was warmed to 0° C. and stirred for 30 minutes. The solution was re-cooled to −78° C. and treated with a solution of the aldehyde 2 (8.31 g, 42.81 mmol, 1.4 eq) in CH$_2$Cl$_2$ (25 mL) and stirred for 1 hour, warmed to 0° C. After 1 hour at 0° C., sodium phosphate buffer (pH 7, 500 mM, 30 mL) followed by methanol (30 mL), was added. After 20 minutes, 30% H$_2$O$_2$ (30 mL) was added, keeping the temperature less than 10° C. and the mixture was stirred at 0° C. for 1 hour. Organics were removed under reduced pressure and the remaining aqueous layer was extracted with ethyl acetate (EtOAc) (3×100 mL). The combined organics were washed with 1 N HCl, 5% aq NaHCO$_3$, brine, dried over Na$_2$SO$_4$, filtered, and concentrated. The residue was purified by flash chromatography (33% EtOAc/Hexanes) to give 3 (11.98 g, 89% yield) as a clear and colorless oil: R$_f$=0.2 (33% EtOAc/Hexanes); $^1$H NMR (600 MHz, CDCl$_3$) δ 7.31 (ddd, J=7.4, 6.4, 1.3 Hz, 2H), 7.28-7.25 (m, 2H), 7.24-7.21 (m, 2H), 7.20-7.15 (m, 2H), 6.04 (dddd, J=17.6, 10.0, 9.0, 1.1 Hz, 1H), 5.39-5.36 (m, 1H), 5.36-5.34 (m, 1H), 4.68 (ddt, J=11.4, 6.3, 3.0 Hz, 1H), 4.58-4.51 (m, 1H), 4.42 (s, 2H), 4.25-4.19 (m, 1H), 4.18-4.11 (m, 2H), 3.78 (d, J=1.1 Hz, 3H), 3.69-3.64 (m, 1H), 3.64-3.56 (m, 1H), 3.28-3.17 (m, 1H), 2.74 (dd, J=13.4, 9.5 Hz, 1H), 1.93-1.78 (m, 1H), 1.74 (dt, J=14.5, 7.0 Hz, 1H), 1.55 (s, 2H); $^{13}$C NMR (150 MHz, CDCl$_3$) δ 173.46, 159.19, 152.90, 135.04, 131.67, 130.14, 129.42, 129.30, 128.91, 127.35, 121.00, 113.78, 72.87, 70.54, 67.74, 65.95, 55.25, 55.17, 52.53, 37.58, 33.87; HRMS (ES) cicd for C$_{25}$H$_{29}$NO$_6$ [M+Na] 462.1887, found 462.1885

(R)-4-benzyl-3-((2R,3S)-3-((tert-butyldimethylsilyl)oxy)-5-((4-methoxybenzyl)oxy)-2-vinylpentanoyl)oxazolidin-2-one (3).

To a solution of S3 (17.56 g, 39.95 mmol, 1 eq) and 2,6-lutidine (46.28 mL, 79.91 mmol, 2 eq) in CH$_2$Cl$_2$ (135 mL, 0.3 M) was added tert-butylsilyltrifluoromethane sulfonate (11.6 mL, 59.9 mmol, 1.5 eq) and stirred. After 18 hours at room temperature, H$_2$O (100 mL) was added, stirred for 30 minutes, the organic layer was separated, and the aqueous layer was extracted with CH$_2$Cl$_2$ (2×100 mL). The combined organics were washed with 1 N HCl, sat. aq NaHCO$_3$, brine, dried over Na$_2$SO$_4$, filtered and concentrated. The residue was purified by flash chromatography (20% EtOAC/Hexanes) to give 3 (18.08 g, 84% yield) as a pale yellow oil: R$_f$=0.6 (33% EtOAc/Hexanes); $^1$H NMR (400 MHz, CDCl$_3$) δ 7.33-7.26 (m, 3H), 7.25 (d, J=8.8 Hz, 2H), 7.18 (d, J=6.9 Hz, 2H), 6.85 (d, J=8.6 Hz, 2H), 6.00 (ddd, J=9, 9.3, 18.2 Hz, 1H), 5.27 (d, J=10.2 Hz, 1H), 5.26 (d, J=18.1 Hz, 1H), 4.58 (dd, J=6.6 Hz, 8.8 Hz, 1H), 4.56-4.52 (m, 1H), 4.41 (d, J=11.4 Hz, 1H), 4.36 (d, J=11.5 Hz, 1H), 4.21 (td, J=5.2 Hz, 6.4 Hz, 1H), 4.05 (dd, J=2 Hz, 9.2 Hz, 1H), 3.86 (t, J=8.2 Hz, 1H), 3.78 (s, 3H), 3.59 (td, J=6.5, 9.2 Hz, 1H), 3.48 (dt, J=6.2, 9.4 Hz, 1H), 3.23 (dd, J=3.0, 13.4 Hz, 1H), 2.70 (dd, J=9.7, 13.4 Hz, 1H), 1.95-1.85 (m, 2H), 0.86 (s, 9H), 0.02 (s, 3H), 0.01 (s, 3H); $^{13}$C NMR (100 MHz, CDCl$_3$) δ 172.62, 159.24, 153.02, 135.58, 134.24, 130.86, 129.68, 129.49, 129.10, 127.48, 119.70, 113.86, 72.77, 71.29, 66.03, 65.94, 55.66, 55.48, 53.39, 37.73, 35.47, 26.02, 18.22, −4.23, −4.38; HRMS (ES) calculated for C$_{31}$H$_{43}$NO$_6$Si [M+Na] 576.2752, found 576.2767.

(2S,3S)-3-((tert-butyldimethylsilyl)oxy)-5-((4-methoxybenzyl)oxy)-2-vinylpentan-1-ol (4).

To a solution of 3 (17.22 g, 31.14 mmol, 1 eq) in tetrahydrofuran (THF) (625 mL, 0.05 M) cooled to 0° C. was added a solution of NaBH$_4$ (5.891 g, 155.7 mmol, 5 eq) in H$_2$O (240 mL). After 10 minutes at 0° C., the solution was warmed to room temperature, and stirred for 5 hours. The reaction was quenched by the addition of sat. aq NH$_4$Cl solution (200 mL) and the mixture stirred at room temperature for 1 hour. The THF was removed under reduced pressure and the aqueous layer was extracted with EtOAc (3×75 mL), organics combined, washed with brine, dried over Na$_2$SO$_4$, filtered and concentrated. The residue was purified by flash chromatography (18% EtOAc/Hexanes) to afford 4 (10.04 g, 85% yield) as a colorless oil; R$_f$=0.25 (20% EtOAc/Hexanes); $^1$H NMR (400 MHz, CDCl$_3$) δ 7.25 (d, J=8.8 Hz, 2H), 6.88 (d, J=8.6 Hz, 2H), 5.71 (ddd, J=17.3, 10.4, 8.6 Hz, 1H), 5.17 (d, J=10.4 Hz, 1H), 5.10 (d, J=17.4 Hz, 1H), 4.43 (d, J=11.5 Hz, 1H), 4.38 (d, J=11.5 Hz, 1H), 4.04 -3.94 (m, 1H), 3.80 (s, 3H), 3.75 (dt, J=10.8, 6.6 Hz, 1H), 3.61 (ddd, J=11.0, 7.0, 5.0 Hz, 1H), 3.46 (t, J=6.3 Hz, 2H), 2.43 (qd, J=7.6, 2.7 Hz, 1H), 2.15 (t, J=5.7 Hz, 1H), 1.88 -1.68 (m, 2H), 0.88 (s, 9H), 0.09 (s, 3H), 0.06 (s, 3H).$^{13}$C NMR (100 MHz, CDCl$_3$) δ 159.28, 135.60, 130.61, 129.41, 118.67, 113.89, 72.72, 71.06, 66.63, 63.67, 55.43, 51.34, 34.11, 25.98, 18.14, −4.41, −4.42; HRMS (ES) calculated for C$_{21}$H$_{36}$O$_4$Si [M+Na] 403.2275, found 403.2271.

(5S,6S)-5-(2-((4-methoxybenzyl)oxy)ethyl)-2,2,3,3,9,9,10,10-octamethyl-6-vinyl-4,8-dioxa-3,9-disilaundecane (5).[3, 4]

To a stirred solution of 4 (9.81 g, 25.8 mmol, 1 eq) in dry pyridine (250 mL, 0.1 M) cooled to 0° C. was added p-toluenesulfonyl chloride (7.372 g, 38.66 mmol, 1.5 eq). The mixture was stirred for 30 minutes and warmed to room temperature. After 4 hours, the mixture was re-cooled to 0° C. and 0.5 N HCl (300 mL) was slowly added. The aqueous layer was extracted with diethyl ether (3×200 mL), organics combined, washed with 1 M HCl, brine, dried over Na$_2$SO$_4$, filtered, and concentrated. The residue was purified using a chromatographic plug (18% EtOAc/Hexanes) to afford 5 (11.67 g, 84% yield) as a colorless oil: R$_f$=0.4 (20% EtOAc/Hexanes); $^1$H NMR (400 MHz, CDCl$_3$) δ 7.75 (d, J=8.4 Hz, 2H), 7.30 (d, J=8.4 Hz, 2H), 7.21 (d, J=8.4 Hz, 2H), 6.86 (d, J=8.4 Hz, 2H), 5.58 (ddd, J=8.7, 10.3, 17.3 Hz, 1H), 5.12 (dd, J=1.2, 9.2 Hz, 1H), 5.04 (d, J=17.2 Hz, 1H), 4.39 (d, J=11.6 Hz, 1H), 4.33 (d, J=11.6 Hz, 1H), 4.08 (dd, J=6.6, 9.4 Hz, 1H), 3.94 (dd, J=7.4, 9.4 Hz, 1H), 3.93-3.89 (m, 1H), 3.79 (s, 3H), 3.35 (t, J=6.4 Hz, 2H), 2.46-2.42 (m, 1H), 2.42 (s, 3H), 1.74-1.57 (m, 2H), 0.78 (s, 9H), -0.01 (s, 3H), -0.05 (s, 3H); $^{13}$C NMR (100 MHz, CDCl$_3$) δ 159.30, 144.80, 133.44, 133.15, 130.53, 129.91, 129.39, 128.14, 119.79, 113.92, 72.73, 70.54, 68.83, 66.36, 55.43, 48.61, 34.64, 25.91, 21.77, 18.11, −4.25, −4.69; HRMS (ES) calculated for C$_{28}$H$_{42}$O$_6$SSi [M+Na] 557.2364, found 557.2370.

tert-butyl(((3S,4R)-1-((4-methoxybenzyl)oxy)-4-methylhex-5-en-3-yl)oxy)dimethylsilane (6).[5]

To a solution of 5 (3.72 g, 6.96 mmol, 1 eq) in dry THF (70 mL, 0.1 M) cooled to 0° C. was added lithium triethylborohydride (1 M in THF, 17.39 mL, 17.39 mmol, 2.5 eq) over 10 minutes. The reaction was stirred at 0° C., warmed to room temperature and stirred for an additional 2 hours. The reaction was cooled to 0° C., quenched with the slow addition of water (15 mL), 3 N NaOH (15 mL), 30% $H_2O_2$ (15 mL), and stirred for 30 minutes. The organics were removed under reduced pressure and the aqueous layer was extracted with EtOAc (3×50 mL). The combined organics were washed with brine, dried over $Na_2SO_4$, filtered, and concentrated. The residue was purified by flash chromatography (10% EtOAc/Hexanes) to yield 6 (1.87 g, 74% yield) as a clear and colorless oil: $R_f$=0.5 (10% EtOAc/Hexanes); $^1$H NMR (600 MHz, $CDCl_3$) δ 7.25 (d, J=8.3 Hz, 2H), 6.87 (d, J=8.2 Hz, 2H), 5.76 (ddd, J=17.4, 10.1, 7.3 Hz, 1H), 4.99 (d, J=9.8 Hz, 1H), 4.98 (d, J=18.1 Hz, 1H), 4.43 (d, J=11.5 Hz, 1H), 4.38 (d, J=11.5 Hz, 1H), 3.80 (s, 3H), 3.76 (dt, J=8.0, 4.2 Hz, 1H), 3.52-3.42 (m, 2H), 2.29 (td, J=7.1, 3.9 Hz, 1H), 1.74-1.60 (m, 2H), 0.99 (d, J=6.9 Hz, 3H), 0.88 (s, 9H), 0.05 (s, 3H), 0.03 (s, 3H). $^{13}$C NMR (100 MHz, $CDCl_3$) δ 159.23, 140.84, 130.85, 129.39, 114.67, 113.87, 72.68, 72.65, 67.24, 55.43, 43.58, 33.36, 26.05, 18.27, 14.68, −4.26, −4.39; HRMS (ES) calculated for $C_{21}H_{36}O_3Si$ [M+H] 364.2434, found 364.2439.

(tert-butyl(((3S,4R, E)-1-((4-methoxybenzyl)oxy)-4-methyl-6-(4,4,5,5-tetramethyl-1,3,2-dioxaborolan-2-yl)hex-5-en-3-yl)oxy)dimethylsilane (7).[6]

A solution of Hoveyda Grubbs II (0.10 g, 0.16 mmol, 0.05 eq) in dry $CH_2Cl_2$ (15 mL, 0.2 M)) was added to a two-neck flask fitted with a reflux condenser under $N_2$. To this was added olefin 6 (1.15 g, 3.15 mmol, 1 eq), followed by vinylboronic acid pinacol ester (1.07 mL, 6.31 mmol, 3 eq, passed through a plug of $SiO_2$ using 10% EtOAc/Hex as the eluent to remove stabilizer immediately prior to use), and the reaction was heated at reflux for 18 hours. The reaction was cooled, concentrated, and purified directly by flash chromatography (5% EtOAc/Hexanes) to yield 7 (1.10 g, 74% yield) as a pale yellow oil: $R_f$=0.35 (5% EtOAc/Hexanes); $^1$H NMR (400 MHz, $CDCl_3$) δ 7.25 (d, J=8.1 Hz, 2H), 6.87 (d, J=8.0 Hz, 2H), 6.56 (dd, J=18.1, 6.6 Hz, 1H), 5.43 (d, J=18.1 Hz, 1H), 4.41 (d, J=18.0 Hz, 1H), 4.38 (d, J=17.9 Hz, 1H), 3.87-3.75 (m, 1H), 3.80 (d, J=0.8 Hz, 3H), 3.55-3.38 (m, 2H), 2.40 (q, J=6.2 Hz, 1H), 1.66 (q, J=6.7 Hz, 2H), 1.26 (s, 12H), 1.00 (d, J=6.9 Hz, 3H), 0.87 (d, J=0.8 Hz, 9H), 0.03 (s, 3H), 0.02 (s, 3H); $^{13}$C NMR (100 MHz, $CDCl_3$) δ 159.31, 156.21, 130.88, 129.52, 113.96, 83.26, 72.77, 72.45, 67.42, 55.50, 45.53, 32.93, 26.12, 25.06, 24.96, 18.32, 13.32, −4.20, −4.42; HRMS (ES) calculated for $C_{27}H_{47}BO_5Si$ [M+H] 491.3359, found 491.3350.

(3S,4R,E)-3-((tert-butyldimethylsilyl)oxy)-4-methyl-6-(4,4,5,5-tetramethyl-1,3,2-dioxaborolan-2-yl)hex-5-en-1-ol (S4).

To a solution of 7 (1.90 g, 3.87 mmol, 1 eq) in $CH_2Cl_2$ (25 mL, 0.15 M) and water (1.49 mL) at room temperature was added DDQ (1.32 g, 5.81 mmol, 1.5 eq) and the mixture was stirred for 1 hour. The reaction was quenched with sat. $NaHCO_3$, stirred for 10 minutes, and diluted with water. The organic layer was separated and the aqueous layer was extracted with $CH_2Cl_2$ (2×50 mL), the organics were combined, dried over $Na_2SO_4$, filtered, and concentrated. The residue was purified by flash chromatography (12% EtOAc/Hexanes) to yield S4 (1.21 g, 83% yield) as a colorless oil: $R_f$=0.15 (10% EtOAc/Hexanes); $^1$H NMR (600 MHz, $CDCl_3$) δ 6.54 (dd, J=18.1, 6.6 Hz, 1H), 5.46 (dd, J=18.1, 1.5 Hz, 1H), 3.87 (ddd, J=7.9, 5.0, 3.8 Hz, 1H), 3.77-3.67 (m, 2H), 2.49 (pdd, J=6.8, 5.0, 1.5 Hz, 1H), 2.03 (t, J=5.4 Hz, 1H), 1.71-1.63 (m, 2H), 1.26 (d, J=1.7 Hz, 12H), 1.01 (d, J=6.8 Hz, 3H), 0.89 (s, 9H), 0.08 (s, 3H), 0.07 (s, 3H); $^{13}$C NMR (150 MHz, $CDCl_3$) δ 155.72, 83.07, 74.24, 60.63, 44.92, 34.15, 25.84, 24.80, 24.71, 17.98, 12.81, −4.41, −4.69; HRMS (ES) calculated for $C_{19}H_{39}BO_4Si$ [M+H] 371.2783, found 371.2778.

(3S,4R,E)-3-((tert-butyldimethylsilyl)oxy)-4-methyl-6-(4,4,5,5-tetramethyl-1,3,2-dioxaborolan-2-yl)hex-5-enal (8).

To an open round bottom flask was added alcohol S4 (1.00 g, 4.09 mmol, 1 eq) in $CH_2Cl_2$ (41 mL, 0.1 M) and treated with $NaHCO_3$ (1.72 g, 20.45 mmol, 5 eq) and desmartin periodinane (2.08 g, 4.91 mmol, 1.2 eq). The reaction was stirred at rt for 1 hour, quenched with 10% $Na_2S_2O_3$ solution (50 mL), and stirred until both layers were clear. The organics were separated and the aqueous layer extracted with $CH_2Cl_2$ (2×50 mL). The combined organics were washed with brine, dried over sodium sulfate, filtered, and concentrated. The residue was purified by flash chromatography (10% EtOAc/Hexanes) to afford 8 (0.768 g, 77% yield) as a colorless oil: $R_f$=0.5 (10% EtOAc/Hexanes); $^1$H NMR (400 MHz, $CDCl_3$) δ9.75 (dd, J=2.1, 1.1 Hz, 1H), 6.50 (dd, J=18.1, 6.6 Hz, 1H), 5.46 (d, J=18.0 Hz, 1H), 4.22 (dt, J=8.1, 4.2 Hz, 1H), 2.54-2.42 (m, 2H), 2.41-2.33 (m, 1H), 1.25 (s, 12H), 1.01 (dd, J=6.9, 0.9 Hz, 3H), 0.85 (d, J=0.8 Hz, 9H), 0.05 (s, 3H), 0.02 (s, 3H); $^{13}$C NMR (100 MHz, $CDCl_3$) δ 202.47, 154.68, 83.36, 70.89, 47.17, 45.54, 29.86, 25.92, 24.98, 24.88, 18.16, 13.03, −4.33, −4.56; HRMS (ES) calculated for $C_{19}H_{37}BO_4Si$ [M+H] 368.2554, found 368.2550.

2. Unit B Synthesis

Figure 4:
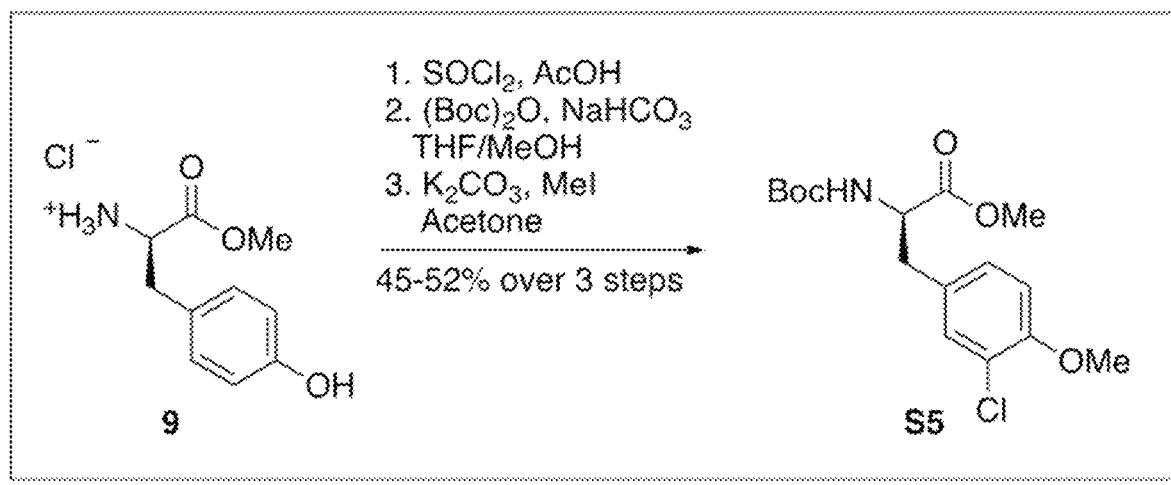
FIG. 4. A schematic illustration of the synthesis of a unit B fragment.

S5 was synthesized in three steps from commercially available 9 as shown in FIG. 4 and as previously reported.[7]

methyl(R)-3-(3-chloro-4-methoxyphenyl)-2-(2-(diethoxyphosphoryl) acetamido)propanoate (12).

To an open flask was added S5 (1.10 g, 3.20 mmol, 1 eq) and 4 M HCl/Dioxane (20 mL). The mixture was vigorously stirred for 30 minutes and concentrated under reduced pressure. The resulting white solid 10 was used directly.

Compound 10 was suspended in DMF (32 mL, 0.1 M) and treated with 2-(diethoxyphosphoryl)acetic acid 11 (0.692 g, 3.52 mmol, 1.1 eq), EDC.HCl (0.731 g, 3.84 mmol, 1.2 eq), HOBt hydrate (0.591 g, 3.84 mmol, 1.2 eq), and DI PEA (1.03 g, 1.40 mL, 8.00 mmol, 2.5 eq) and stirred at room temperature for 18 hours. The reaction was quenched with half sat. aq $NH_4Cl$ (30 mL), the aqueous layer extracted (3×30 mL) with DCM, organics combined, dried over sodium sulfate, filtered, and concentrated. The residue was purified with a flash chromatography system (1-7% methanol/DCM) to yield 12 (0.90 mg, 67% yield) as a clear and colorless oil: $R_f$=0.2 (2.5% methanol/DCM); $^1$H NMR (600 MHz, $CDCl_3$) δ 7.16 (d, J=2.2 Hz, 1H), 7.09 (bd, J=7.5 Hz, 1H), 7.04 (dd, J=8.4, 2.2 Hz, 1H), 6.84 (d, J=8.4 Hz, 1H), 4.78 (td, J=7.1, 5.4 Hz, 1H), 4.13 (dt, J=14.9, 7.2 Hz, 1H), 4.06 (dq, J=8.2, 7.1 Hz, 2H), 3.85 (s, 3H), 3.70 (s, 3H), 3.08 (dd, J=14.2, 5.4 Hz, 1H), 2.97 (dd, J=14.2, 6.8 Hz, 1H), 2.85 (d, J=10.7 Hz, 1H), 2.81 (d, J=10.5 Hz, 1H), 1.31 (t, J=7.1 Hz, 3H), 1.27 (t, J=7.1 Hz, 3H); $^{13}$C NMR (150 MHz, $CDCl_3$) δ 171.45, 163.95, 163.93, 154.24, 131.09, 129.15, 128.72, 122.48, 112.22, 77.37, 77.16, 76.95, 62.95 (d, J=15.3 Hz), 62.91 (d, J=15.3), 56.25, 53.94, 52.52, 36.88, 35.70, 34.83, 16.48, 16.43, 16.39; HRMS (ES) calculated for $C_{17}H_{25}ClNO_7P$ [M+H] 421.1057, found 421.1053.

3. Unit A/B Analog Synthesis and Characterization methyl (R)-2-((2E,5S,6R,7E)-5-((tert-butyldimethyl-silyl)oxy)-6-methyl-8-(4,4,5,5-tetramethyl-1,3,2-dioxaborolan-2-yl)octa-2,7-dienamido)-3-(3-chloro-4-methoxyphenyl)propanoate (13).

A suspension of 12 (0.63 g, 1.49 mmol, 1 eq) in dry THF (15 mL, 0.1 M) was cooled to 0° C. and treated with NaH (60% suspension in oil, 0.055 g, 1.64 mmol, 1.1 eq). The reaction was stirred for 30 min prior to the dropwise addition of aldehyde 8 (0.55g, 1.49 mmol, 1 eq) in THF (5 mL). The reaction was allowed to stir at 0° C. for 1 h and quenched with half sat. $NH_4Cl$ (10 mL). The organics was removed under reduced pressure, the remaining aqueous layer was extracted with DCM (3×50 mL), organics combined, washed with brine, dried over sodium sulfate, filtered, and concentrated. The crude product was purified by flash chromatography system (6-45% EtOAc/Hexanes) to afford 13 (0.545 g, 57.4% yield) as a clear and colorless oil: $R_f$=0.25 (25% EtOAc/Hexanes); $^1$H NMR : (400 MHz, $CD_3OD$) δ 7.21 (d, J=2.2 Hz, 1H), 7.10 (dd, J=8.5, 2.2 Hz, 1H), 6.97 (d, J=8.4 Hz, 1H), 6.75 (dt, J=15.2, 7.5 Hz, 1H), 6.57 (dd, J=18.0, 7.7 Hz, 1H), 5.96 (d, J=15.3 Hz, 1H), 5.38 (d, J=18.3 Hz, 1H), 4.68 (dd, J=8.9, 5.5 Hz, 1H), 3.84 (s, 3H), 3.73 (q, J=5.4 Hz, 1H), 3.70 (s, 3H), 3.11 (dd, J=14.0, 5.6 Hz, 1H), 2.90 (dd, J=14.0, 9.0 Hz, 1H), 2.41-2.25 (m, 3H), 1.26 (s, 12H), 1.01 (d, J=6.8 Hz, 3H), 0.89 (s, 9H), 0.06 (s, 3H), 0.03 (s, 3H); $^{13}$C NMR: (100 MHz, $CD_3OD$) δ 173.28, 167.98, 157.33, 155.42, 143.28, 131.82, 131.33, 129.70, 126.29, 123.20, 113.34, 84.41, 76.09, 56.55, 55.19, 52.72, 46.48, 38.38, 37.30, 26.47, 25.14, 25.10, 19.00, 15.81, −3.99, −4.30; HRMS (ESI) calculated for $C_{32}H_{51}BClNO_7Si$ [M+H] 635.3216, found 635.3215.

4. General Suzuki Coupling Procedure

To a long tube was added 13 (1 eq), $K_3PO_4$ (2.5 eq), aryl iodide (2 eq), and $Pd_2(dba)_3$ (0.05 eq), suspended in a mixture 1,2 dichloroethane and water (4:1, 0.1 M) and stirred vigorously until completion, as assessed by TLC (2-12 hours). The reaction was diluted with 0.5 M HCl and EtOAc, and the aqueous layer was extracted with EtOAc (3×20 mL). The organics were combined, dried over $Na_2SO_4$, filtered, and purified by flash chromatography system as indicated herein.

methyl (R)-2-((2E,5S,6R,7E)-5-((tert-butyldimethyl-silyl)oxy)-6-methyl-8-phenylocta-2,7-dienamido)-3-(3-chloro-4-methoxyphenyl)propanoate (14a).

Reaction was run according to the general Suzuki procedure, and purified using a flash chromatography system (SiO2, 20-50% EtOAc/Hexanes) to afford 14a (0.086 g, 93% yield) as a pale yellow oil: $R_f$=0.35 (25% EtOAc/Hexanes); $^1$H NMR (400 MHz, $CD_3OD$) δ 7.33 (d, J=7.5 Hz, 2H), 7.27 (t, J=7.6 Hz, 2H), 7.21 (d, J=2.2 Hz, 1H), 7.18 (t, J=7.2 Hz, 1H), 7.10 (dd, J=8.4, 2.2 Hz, 1H), 6.96 (d, J=8.4 Hz, 1H), 6.78 (dt, J=15.2, 7.5 Hz, 1H), 6.38 (d, J=16.0 Hz, 1H), 6.19 (dd, J=16.0, 8.2 Hz, 1H), 5.96 (d, J=15.4 Hz, 1H), 4.69 (dd, J=8.9, 5.6 Hz, 1H), 3.83 (s, 3H), 3.80 (q, 1H), 3.70 (s, 3H), 3.11 (dd, J=14.0, 5.6 Hz, 1H), 2.90 (dd, J=14.0, 9.0 Hz, 1H), 2.44 (q, J=6.5 Hz, 1H), 2.37 (t, J=6.9 Hz, 2H), 1.11 (d, J=6.9 Hz, 3H), 0.90 (s, 9H), 0.06 (s, 3H), 0.05 (s, 3H); $^{13}$C NMR (100 MHz, $CD_3OD$) 173.28, 168.03, 155.41, 143.50, 139.03, 133.10, 131.82, 131.73, 131.33, 129.67, 129.50, 128.04, 127.06, 126.17, 123.18, 113.33, 76.54, 56.53, 55.15, 52.72, 44.11, 38.62, 37.27, 26.44, 18.98, 16.80, −4.01, −4.32.; HRMS (ES) calculated for $C_{32}H_{44}ClNO_5Si$ [M+H] 586.2750, found 586.2754.

methyl (R)-2-((2E,5S,6R,7E)-5-((tert-butyldimethyl-silyl)oxy)-6-methyl-8-(pyridin-2-yl)octa-2,7-dienamido)-3-(3-chloro-4-methoxyphenyl)propanoate (14b).

Reaction was run according to the general Suzuki procedure, and purified by flash chromatography (Si—$NH_2$, 20-50% EtOAc/Hexanes) to afford 14b (0.078 g, 45% yield) as a pale yellow oil: $R_f$=0.15 (50% EtOAc/Hexanes); $^1$H NMR (400 MHz, $CD_3OD$) δ 8.44 (d, J=4.0 Hz, 1H), 7.76 (td, J=7.8, 1.8 Hz, 1H), 7.46 (d, J=8.0 Hz, 1H), 7.24 (dd, J=7.8, 5.2 Hz, 1H), 7.21 (d, J=2.1 Hz, 1H), 7.10 (dd, J=8.5, 2.2 Hz, 1H), 6.96 (d, J=8.3 Hz, 1H), 6.77 (dt, J=15.3, 7.4 Hz, 1H), 6.64 (dd, J=16.0, 8.2 Hz, 1H), 6.49 (d, J=16.0 Hz, 1H), 5.98 (d, J=15.4 Hz, 1H), 4.70 (dd, J=9.0, 5.5 Hz, 1H), 3.87-3.84 (m, 1H), 3.83 (m, 3H), 3.70 (s, 3H), 3.11 (dd, J=14.0, 5.5 Hz, 1H), 2.90 (dd, J=14.0, 9.0 Hz, 1H), 2.51 (h, J=6.8 Hz, 1H), 2.38 (t, J=6.8 Hz, 2H), 1.14 (d, J=6.8 Hz, 3H), 0.90 (s, 9H), 0.06 (s, 3H), 0.05 (s, 3H). $^{13}$C NMR (100 MHz, $CD_3OD$) δ 173.27, 167.95, 157.17, 155.41, 149.74, 143.24, 139.05, 138.66, 131.83, 131.34, 131.12, 129.70, 126.38, 123.38, 123.17, 122.34, 113.34, 76.26, 56.53, 55.15, 52.73, 44.06, 38.62, 37.31, 26.43, 18.97, 16.47, −4.04, −4.34. HRMS (ES) calculated for $C_{31}H_{43}ClN_2O_5Si$ [M+H] 587.2703, found 587.2705.

methyl (R)-2-((2E,5S,6R,7E)-5-((tert-butyldimethyl-silyl)oxy)-6-methyl-8-(pyridin-3-yl)octa-2,7-dienamido)-3-(3-chloro-4-methoxyphenyl)propanoate (14c).

Reaction was run according to the general Suzuki procedure, and purified by flash chromatography system (Si—$NH_2$, 16-60% EtOAc/Hexanes) to afford 14c (0.049 g, 72% yield) as a pale yellow oil: $R_f$=0.15 (50% EtOAc/Hexanes); $^1$H NMR (600 MHz, $CD_3OD$) δ 8.49 (d, J=2.1 Hz, 1H), 8.35 (dd, J=4.9, 1.5 Hz, 1H), 7.85 (d, J=8.0 Hz, 1H), 7.37 (dd, J=8.0, 4.8 Hz, 1H), 7.21 (d, J=2.1 Hz, 1H), 7.10 (dd, J=8.4, 2.2 Hz, 1H), 6.96 (d, J=8.5 Hz, 1H), 6.78 (dt, J=15.2, 7.5 Hz, 1H), 6.43 (d, J=16.1 Hz, 1H), 6.36 (dd, J=16.1, 7.9 Hz, 1H), 5.97 (dt, J=15.3, 1.4 Hz, 1H), 4.70 (dd, J=8.9, 5.6 Hz, 1H), 3.85-3.79 (m, 1H), 3.83 (s, 3H), 3.70 (s, 3H), 3.11 (dd, J=14.0, 5.6 Hz, 1H), 2.91 (dd, J=14.0, 9.0 Hz, 1H), 2.49 (td, J=7.2, 4.7 Hz, 1H), 2.38 (ddd, J=7.4, 5.8, 1.4 Hz, 2H), 1.13 (d, J=6.9 Hz, 3H), 0.90 (s, 9H), 0.06 (s, 3H), 0.05 (s, 3H); $^{13}$C NMR (150 MHz, $CD_3OD$) δ173.27, 167.97, 155.43, 148.28, 148.13, 143.21, 136.88, 135.48, 134.71, 131.82, 131.35, 129.68, 127.66, 126.31, 125.28, 123.20, 113.39, 76.32, 56.56, 55.15, 52.72, 44.24, 38.69, 37.29, 26.42, 18.96, 16.65, −4.00, −4.34; HRMS (ES) calculated for $C_{31}H_{43}ClN_2O_5Si$ [M+H] 587.2703, found 587.2702.

methyl (R)-2-((2E,5S,6R,7E)-5-((tert-butyldimethyl-silyl)oxy)-6-methyl-8-(pyridin-4-yl)octa-2,7-dienamido)-3-(3-chloro-4-methoxyphenyl)propanoate (14d).

Reaction was run according to the general Suzuki procedure, and purified by flash chromatography system (Si—$NH_2$, 15-55% EtOAc/Hexanes) to afford 14 d (0.062 g, 71% yield) as a pale yellow oil: $R_f$=0.25 (50% EtOAc/Hexanes); $^1$H NMR (600 MHz, $CD_3OD$) δ δ8.42 (d, J=5.9 Hz, 2H), 7.37 (d, J=6.3 Hz, 2H), 7.21 (d, J=2.1 Hz, 1H), 7.10 (dd, J=8.5, 2.1 Hz, 1H), 6.97 (d, J=8.4 Hz, 1H), 6.78 (dt, J=15.2, 7.5 Hz, 1H), 6.56 (dd, J=16.0, 8.2 Hz, 1H), 6.41 (d, J=16.0 Hz, 1H), 5.97 (d, J=15.3 Hz, 1H), 4.69 (dd, J=9.0, 5.5 Hz, 1H), 3.86-3.81 (m, 1H), 3.83 (s, 3H), 3.70 (s, 3H), 3.11 (dd, J=14.1, 5.6 Hz, 1H), 2.91 (dd, J=14.1, 9.0 Hz, 1H), 2.51 (td, J=13.3, 6.5 Hz, 1H), 2.38 (t, J=6.9 Hz, 2H), 1.13 (d, J=6.8 Hz, 3H), 0.90 (s, 9H), 0.06 (s, 3H), 0.06 (s, 3H). $^{13}$C NMR (150 MHz, CD$_3$OD) $^{13}$C NMR (150 MHz, CD$_3$OD) δ 173.28, 167.96, 155.44, 150.23, 147.68, 143.05, 139.96, 131.83, 131.36, 129.67, 129.19, 126.37, 123.20, 122.32, 113.40, 76.19, 56.56, 55.14, 52.73, 44.24, 38.75, 37.28, 26.41, 18.96, 16.56, −4.02, −4.36; HRMS (ES) calculated for C$_{31}$H$_{43}$ClN$_2$O$_5$Si [M+H] 587.2703, found 587.2699.

methyl (R)-2-((2E,5S,6R,7E)-5-((tert-butyldimethylsilyl)oxy)-6-methyl-8-(pyrazin-2-yl)octa-2,7-dienamido)-3-(3-chloro-4-methoxyphenyl)propanoate (14e).

Reaction was run according to the general Suzuki procedure, and purified by flash chromatography system (Si—NH$_2$, 20-55% EtOAc/Hexanes) to afford 14e (0.115 g, 65% yield) as a pale yellow oil: R$_f$=0.2 (50% EtOAc/Hexanes); $^1$H NMR (600 MHz, CD$_3$OD) δ 8.57 (d, J=1.5 Hz, 1H), 8.51 (s, 1H), 8.39 (d, J=2.6 Hz, 1H), 7.21 (d, J=2.2 Hz, 1H), 7.10 (dd, J=8.4, 2.2 Hz, 1H), 6.96 (d, J=8.5 Hz, 1H), 6.90 (dd, J=15.9, 8.3 Hz, 1H), 6.78 (dt, J=15.2, 7.5 Hz, 1H), 6.54 (d, J=16.0 Hz, 1H), 5.98 (d, J=15.4 Hz, 1H), 4.70 (dd, J=8.9, 5.5 Hz, 1H), 3.86-3.84 (m, 1H), 3.83 (s, 3H), 3.70 (s, 3H), 3.11 (dd, J=14.0, 5.6 Hz, 1H), 2.91 (dd, J=14.0, 9.0 Hz, 1H), 2.55 (q, J=6.9 Hz, 1H), 2.41-2.33 (m, 2H), 1.15 (d, J=6.8 Hz, 3H), 0.89 (s, 9H), 0.06 (s, 3H), 0.05 (s, 3H); $^{13}$C NMR (150 MHz, CD$_3$OD) δ 173.27, 167.93, 155.42, 152.99, 145.49, 143.89, 143.49, 143.07, 141.77, 131.82, 131.34, 129.69, 127.88, 126.41, 123.19, 113.38, 76.20, 56.56, 55.15, 52.73, 44.13, 38.74, 37.30, 26.42, 18.97, 16.46, −4.01, −4.36; HRMS (ES) calculated for C$_{30}$H$_{42}$ClN$_3$O$_5$Si [M+H] 588.2655, found 588.2659.

Methyl (R)-2-((2E,5S,6R,7E)-5-((tert-butyldimethylsilyl)oxy)-6-methyl-8-(1-methyl-1H-pyrazol-5-yl)octa-2,7-dienamido)-3-(3-chloro-4-methoxyphenyl)propanoate (14f).

Reaction was run according to the general Suzuki procedure, and purified by flash chromatography system (Si—NH$_2$, 20-70% EtOAc/Hexanes) to afford 14f (0.044 g, 63% yield) as a pale yellow oil: R$_f$=0.1 (50% EtOAc/Hexanes); $^1$H NMR (600 MHz, CD$_3$OD) δ 7.34 (d, J=2.0 Hz, 1H), 7.20 (d, J=2.2 Hz, 1H), 7.10 (dd, J=8.4, 2.2 Hz, 1H), 6.96 (d, J=8.4 Hz, 1H), 6.78 (dt, J=15.2, 7.5 Hz, 1H), 6.38 (d, J=15.9 Hz, 1H), 6.33 (d, J=2.1 Hz, 1H), 6.21 (dd, J=15.9, 8.3 Hz, 1H), 5.97 (dt, J=15.4, 1.3 Hz, 1H), 4.69 (dd, J=8.9, 5.6 Hz, 1H), 3.82 (s, 3H), 3.81-3.79 (m, 1H), 3.80 (s, 3H), 3.70 (s, 3H), 3.11 (dd, J=14.0, 5.6 Hz, 1H), 2.91 (dd, J=14.0, 8.9 Hz, 1H), 2.48 (h, J=6.9 Hz, 1H), 2.38 (t, J=6.5 Hz, 2H), 1.12 (d, J=6.9 Hz, 3H), 0.89 (s, 9H), 0.06 (s, 3H), 0.05 (s, 3H). $^{13}$C NMR (150 MHz, CD$_3$OD) δ 173.28, 167.98, 155.44, 143.09, 142.83, 139.14, 138.52, 131.81, 131.36, 129.67, 126.33, 123.21, 118.11, 113.41, 103.42, 76.23, 56.57, 55.17, 52.72, 44.20, 38.79, 37.28, 36.45, 26.42, 18.97, 16.77, −3.99, −4.36; HRMS (ES) calculated for C$_{30}$H$_{44}$ClN$_3$O$_5$Si [M+H] 590.2812, found 590.2811.

methyl (R)-2-((2E,5S,6R,7E)-5-((tert-butyldimethylsilyl)oxy)-6-methyl-8-(1-methyl-1H-pyrazol-3-yl)octa-2,7-dienamido)-3-(3-chloro-4-methoxyphenyl)propanoate (14q).

Reaction was run according to the general Suzuki procedure, and purified by flash chromatography (Si—NH$_2$, 16-55% EtOAc/Hexanes) to afford 14g (0.065 g, 71% yield) as a pale yellow oil: R$_f$=0.25 (50% EtOAc/Hexanes); $^1$H NMR (600 MHz, CD$_3$OD) δ 7.46 (d, J=2.3 Hz, 1H), 7.21 (d, J=2.2 Hz, 1H), 7.10 (dd, J=8.5, 2.2 Hz, 1H), 6.96 (d, J=8.4 Hz, 1H), 6.75 (dt, J=15.2, 7.5 Hz, 1H), 6.30 (d, J=2.3 Hz, 1H), 6.17 (dd, J=16.2, 8.1 Hz, 1H), 5.96 (d, J=15.4 Hz, 1H), 4.69 (dd, J=9.0, 5.6 Hz, 1H), 3.84 (s, 3H), 3.83 (s, 3H), 3.78 (q, J=5.6 Hz, 1H), 3.70 (s, 3H), 3.11 (dd, J=14.1, 5.6 Hz, 1H), 2.91 (dd, J=14.0, 9.0 Hz, 1H), 2.42 (p, J=6.7 Hz, 1H), 2.38-2.30 (m, 2H), 1.09 (d, J=6.8 Hz, 3H), 0.90 (s, 9H), 0.06 (s, 3H), 0.04 (s, 3H); $^{13}$C NMR (150 MHz, CD$_3$OD) δ173.29, 167.99, 155.43, 152.12, 143.43, 134.95, 133.03, 131.82, 131.37, 129.71, 126.28, 123.29, 123.22, 113.38, 103.22, 76.44, 56.55, 55.16, 52.71, 43.95, 38.60, 38.52, 37.33, 26.44, 18.98, 16.48, −4.04, −4.32; HRMS (ES) calculated for C$_{30}$H$_{44}$ClN$_3$O$_5$Si [M+H] 590.2812, found 590.2809.

methyl (R)-2-((2E,5S,6R,7E)-5-((tert-butyldimethylsilyl)oxy)-6-methyl-8-(1-methyl-1 H-pyrazol-4-yl)octa-2,7-dienamido)-3-(3-chloro-4-methoxyphenyl)propanoate (14h).

Reaction was run according to the general Suzuki procedure, and purified by flash chromatography system (Si—NH$_2$, 16-60% EtOAc/Hexanes) to afford 14 h (0.085 g, 92% yield) as a pale yellow oil: R$_f$=0.2 (50% EtOAc/Hexanes); $^1$H NMR (400 MHz, CD$_3$OD) δ 7.53 (s, 1H), 7.47 (s, 1H), 7.21 (d, J=2.2 Hz, 1H), 7.10 (dd, J=8.4, 2.2 Hz, 1H), 6.96 (d, J=8.4 Hz, 1H), 6.77 (dt, J=15.2, 7.5 Hz, 1H), 6.18 (d, J=16.0 Hz, 1H), 5.95 (d, J=15.4 Hz, 1H), 5.89 (dd, J=16.1, 8.2 Hz, 1H), 4.69 (dd, J=8.9, 5.6 Hz, 1H), 3.84 (s, 3H), 3.83 (s, 3H), 3.75 (q, J=5.5 Hz, 1H), 3.70 (s, 3H), 3.11 (dd, J=14.0, 5.6 Hz, 1H), 2.90 (dd, J=14.0, 9.0 Hz, 1H), 2.41-2.27 (m, 3H), 1.06 (d, J=6.8 Hz, 3H), 0.89 (s, 9H), 0.05 (s, 3H), 0.03 (s, 3H). $^{13}$C NMR (150 MHz, CD$_3$OD) δ 173.29, 168.03, 155.42, 143.67, 137.61, 131.83, 131.58, 131.35, 129.68, 129.33, 126.10, 123.18, 122.45, 121.24, 113.36, 76.60, 56.55, 55.15, 52.72, 44.16, 38.72, 38.32, 37.28, 26.44, 18.98, 16.45, −4.05, −4.31; HRMS (ES) calculated for C$_{30}$H$_{44}$ClN$_3$O$_5$Si [M+H] 590.2812, found 590.2813.

methyl (R)-2-((2E,5S,6R,7E)-5-((tert-butyldimethylsilyl)oxy)-8-(1-isopropyl-1H-pyrazol-4-yl)-6-methylocta-2,7-dienamido)-3-(3-chloro-4-methoxyphenyl)propanoate (14i).

Reaction was run according to the general Suzuki procedure, and purified by flash chromatography (Amine column, 20-50% EtOAc/Hexanes) to afford 14i (0.056 g, 83% yield) as a pale yellow oil: R$_f$=0.35 (50% EtOAc/Hexanes); $^1$H NMR (600 MHz, CD$_3$OD) δ $^1$H NMR (400 MHz, Methanol-d$_4$) δ 7.61 (s, 1H), 7.48 (s, 1H), 7.21 (d, J=2.2 Hz, 1H), 7.10 (dd, J=8.4, 2.2 Hz, 1H), 6.96 (d, J=8.4 Hz, 1H), 6.77 (dt, J=15.2, 7.5 Hz, 1H), 6.20 (d, J=16.1 Hz, 1H), 5.95 (d, J=15.3 Hz, 1H), 5.90 (dd, J=16.1, 8.1 Hz, 1H), 4.69 (dd, J=8.9, 5.6 Hz, 1H), 4.46 (hept, J=7.0 Hz, 1H), 3.83 (s, 3H), 3.75 (q, J=5.4 Hz, 1H), 3.70 (s, 3H), 3.11 (dd, J=14.0, 5.6 Hz, 1H), 2.91 (dd, J=14.0, 8.9 Hz, 1H), 2.46-2.29 (m, 3H), 1.46 (d, J=6.7 Hz, 6H), 1.07 (d, J=6.9 Hz, 3H), 0.90 (s, 9H), 0.06 (s, 3H), 0.03 (s, 3H). $^{13}$C NMR (150 MHz, CD$_3$OD) δ $^{13}$C NMR (101 MHz, cd$_3$od) δ 173.29, 168.04, 155.42, 143.72, 137.18, 131.83, 131.35, 129.68, 126.09, 123.19, 121.88, 121.43, 113.36, 76.65, 56.55, 55.16, 54.99, 52.72, 44.16, 38.27, 37.28, 26.44, 23.07, 18.99, 16.38, −4.04, −4.32; HRMS (ES) calculated for C$_{32}$H$_{48}$ClN$_3$O$_5$Si [M+H] 618.3125, found 618.3129.

methyl (R)-2-((2E,5S,6R,7E)-5-((tert-butyldimethyl-silyl)oxy)-8-(3,5-dimethylisoxazol-4-yl)-6-methyl-octa-2,7-dienamido)-3-(3-chloro-4-methoxyphenyl)propanoate (14j).

Reaction was run according to the general Suzuki procedure, and purified by flash chromatography (Amine column, 10-50% EtOAc/Hexanes) to afford 14j (0.057 g, 85% yield) as a pale yellow oil: $R_f$=0.35 (33% EtOAc/Hexanes); $^1$H NMR: (400 MHz, CD$_3$OD) δ7.20 (d, J=2.2 Hz, 1H), 7.10 (dd, J=8.3, 2.2 Hz, 1H), 6.96 (d, J=8.4 Hz, 1H), 6.76 (dt, J=15.2, 7.6 Hz, 1H), 6.11 (d, J=16.3 Hz, 1H), 5.96 (d, J=15.4 Hz, 1H), 5.90 (dd, J=16.4, 8.5 Hz, 1H), 4.68 (dd, J=9.0, 5.5 Hz, 1H), 3.84 (s, 3H), 3.83-3.77 (m, 1H), 3.70 (s, 3H), 3.12 (dd, J=14.0, 5.5 Hz, 1H), 2.90 (dd, J=14.0, 9.0 Hz, 1H), 2.46-2.33 (m, 3H), 2.38 (s, 3H) 2.26 (s, 3H), 1.11 (d, J=6.9 Hz, 3H), 0.90 (s, 9H), 0.07 (s, 3H), 0.06 (s, 3H). $^{13}$C NMR: (100 MHz, CD$_3$OD) δ 173.27, 167.98, 166.46, 159.59, 155.42, 143.21, 135.80, 131.81, 131.33, 129.67, 126.21, 123.17, 119.01, 114.23, 113.36, 76.35, 56.54, 55.17, 52.73, 44.65, 39.15, 37.26, 26.42, 18.97, 17.68, 11.50, 11.40, −3.95, −4.38; HRMS (ES) calculated for $C_{31}H_{35}ClN_2O_6Si$ [M+H] 605.2808, found 605.2801.

5. Unit C/D Characterization

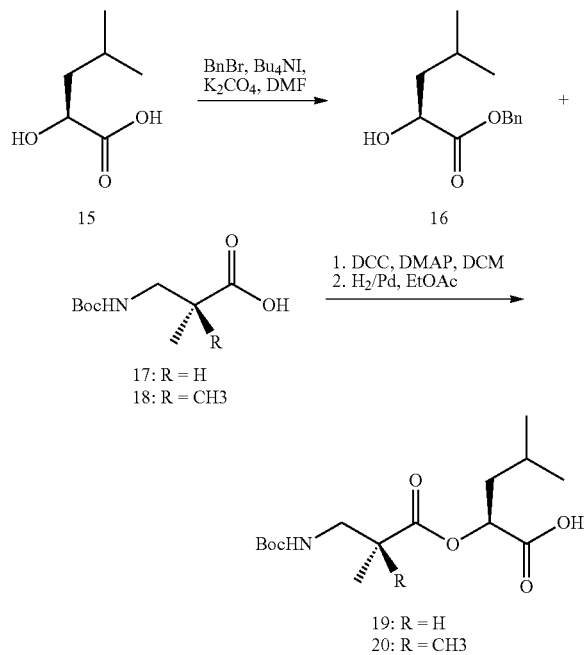

19 and 20 were synthesized from commercially available 15, as shown in FIG. 6B. All spectra were in accordance with published literature.[8-11]

(S)-1-((2-acetamidoethyl)thio)-4-methyl-1-oxopentan-2-yl (R)-3-((tert-butoxycarbonyl)amino)-2-methylpropanoate (21).

To a solution of 19 in DMF (0.1M) was added EDC HCl (1.5 eq), and HOBt (1.2 eq), and the reaction was stirred for 30 minutes. NAc was added and stirred for 10 minutes prior to the addition of catalytic DMAP (0.05 eq). The reaction was stirred for 12 hours, diluted with water and EtOAc and the aqueous layer was extracted (2×40 mL), organics combined, washed with sat. NH$_4$Cl (2×100 mL), and dried over sodium sulfate. The organics were removed under reduced pressure and the remaining residue was purified with a flash chromatography system (1-10% Methanol/DCM) to afford 21 as a white solid. Spectra was in accord with published literature.[12]

(S)-1-((2-acetamidoethyl)thio)-4-methyl-1-oxopentan-2-yl 3-((tert-butoxycarbonyl)amino)-2,2-dimethylpropanoate (22).

To a solution of 20 in DMF (0.1M) was added EDC HCl (1.5 eq) and HOBt (1.2 eq) and the reaction was stirred for 30 minutes. NAc was added and stirred for 10 minutes prior to the addition of catalytic DMAP (0.05 eq). The reaction was stirred for 12 hours, diluted with water and EtOAc and the aqueous layer was extracted (2×40 mL), organics combined, washed with sat. NH$_4$Cl (2×100 mL), and dried over sodium sulfate. The organics were removed under reduced pressure and the remaining residue was purified with the flash chromatography system disclosed herein (1-10% Methanol/DCM) to afford 22 as a white solid. Spectra was in accord with published literature.[12]

6. Seco Cryptophycin Synthesis and Analog Characterization

General Peptide Coupling Procedure.

14a-m (1 eq) was suspended in 1,2 dichloroethane (0.2 M), treated with trimethyltin hydroxide (4 eq), and heat to 80° C. for 4 hours. The reaction was cooled, diluted with DCM and washed with 1 N HCl (2×). The crude acid was used directly.

Simultaneously 21 or 22 (1.1 eq) was suspended in 4 M HCl/Dioxane (5 mL) and stirred for 1 hour at room temperature, concentrated, and used directly.

14a-m acid was suspended in DCM, cooled to 0° C., and treated with HATU (1.1 eq). 21 or 22 amine salt was suspended in DCM and treated with DI PEA (2.5 eq), cooled to 0° C., and added to the mixture. The reaction was allowed to stir overnight, warming to room temperature. The mixture was diluted with half-saturated sodium bicarbonate, the aqueous layer extracted with DCM (3×10 mL), organics combined, washed with brine, dried over Na$_2$SO$_4$, filtered, concentrated, and purified as specified herein. When utilized for analytical analysis, further HPLC purification was performed prior to deprotection on a HydroRP C18 (250×10.0 mm, 4 micron) using a 20-80% water/acetonitrile gradient with a flow rate of 3 mL/min in order to remove any diastereomer produced during the coupling procedure. Semi-preparative reactions were preformed using intermediates directly after purification with the flash chromatography system disclosed herein.

General Deprotection Procedure.

The crude coupling product was suspended in acetonitrile (0.1 M) in an open polypropylene vial. This was treated with 33% aq. HF (2 eq) and allowed to stir until the reaction was complete, as monitored by TLC. The reaction was diluted with DCM, and quenched by the slow addition of sat. NaHCO$_3$ until the aqueous layer was basic. The aqueous layer was then extracted with DCM (3×10 mL), organics combined, washed with brine, dried over Na$_2$SO$_4$, filtered, concentrated, and purified as specified herein. Diastereomeric ratios (dr) are reported as seen by NMR.

(S)-1-((2-acetamidoethyl)thio)-4-methyl-1-oxopentan-2-yl (R)-3-((R)-3-(3-chloro-4-methoxyphenyl)-2-((2E,5S,6R,7E)-5-hydroxy-6-methyl-8-phenylocta-2,7-dienamido)propanamido)-2-methylpropanoate (23a).

Reaction was run as per general coupling procedure and purified with the flash chromatography system (1-10%

Methanol/DCM) R$_f$=0.5 (5% Methanol/DCM). This was then deprotected as per general deprotection procedure and purified by the flash chromatography system (2-14% Methanol/DCM) to afford 23a (0.051 g, 42% yield over 3 steps, 10:1 dr) as a clear and colorless oil: R$_f$=0.35 (10% Methanol/DCM). $^1$H NMR: (600 MHz, CD$_3$OD) δ 7.37 (d, J=7.0 Hz, 2H), 7.27 (t, J=7.9 Hz, 2H), 7.25 (d, J=2.2 Hz, 1H), 7.18 (t, J=7.3 Hz, 1H), 7.14 (dd, J=8.4, 2.2 Hz, 1H), 6.97 (d, J=8.4 Hz, 1H), 6.81 (dt, J=15.1, 7.3 Hz, 1H), 6.41 (d, J=15.9 Hz, 1H), 6.23 (dd, J=15.9, 8.5 Hz, 1H), 6.01 (d, J=15.4 Hz, 1H), 5.21 (dd, J=9.6, 4.0 Hz, 1H), 4.58 (dd, J=8.1, 7.0 Hz, 1H), 3.83 (s, 3H), 3.65 (dt, J=8.7, 4.6 Hz, 1H), 3.48 (dd, J=13.5, 6.6 Hz, 1H), 3.34-3.27 (m, 2H), 3.19 (dd, J=13.5, 7.0 Hz, 1H), 3.06-2.97 (m, 3H), 2.85 (dd, J=13.7, 8.1 Hz, 1H), 2.70 (h, J=7.0 Hz, 1H), 2.44-2.35 (m, 2H), 2.35-2.28 (m, 1H), 1.91 (s, 3H), 1.80-1.74 (m, 1H), 1.74-1.69 (m, 1H), 1.66-1.59 (m, 1H), 1.15 (d, J=6.9 Hz, 3H), 1.10 (d, J=7.1 Hz, 3H), 0.94 (d, J=6.5 Hz, 3H), 0.91 (d, J=6.5 Hz, 3H). $^{13}$C NMR: (150 MHz, CD$_3$OD) 200.34, 175.06, 173.49, 173.42, 168.07, 155.40, 143.51, 139.05, 132.50, 132.09, 131.91, 131.50, 129.84, 129.48, 128.05, 127.14, 126.08, 123.20, 113.35, 78.63, 75.34, 56.57, 56.24, 44.21, 42.73, 41.95, 40.57, 39.85, 38.82, 38.07, 28.58, 25.74, 23.48, 22.54, 21.97, 17.53, 14.87; HRMS (ES) calculated for C$_{39}$H$_{52}$ClN$_3$O$_8$S [M+H] 758.3236, found 758.3238.

(S)-1-((2-acetamidoethyl)thio)-4-methyl-1-oxopentan-2-yl (R)-3-((R)-3-(3-chloro-4-methoxyphenyl)-2-((2E,5S,6R,7E)-5-hydroxy-6-methyl-8-(pyridin-2-yl)octa-2,7-dienamido)propanamido)-2-methylpropanoate (23b).

Reaction was run as per general coupling procedure, and purified by the flash chromatography system (1-10% Methanol/DCM) R$_f$=0.65 (10% Methanol/DCM). This was then deprotected as per general deprotection procedure and purified by the flash chromatography system (2-15% Methanol/DCM) to afford 23b (0.025 g, 38% yield over 3 steps, 7:1 dr) as a clear and colorless oil: R$_f$=0.25 (10% Methanol/DCM); $^1$H NMR: (600 MHz, CD$_3$OD) δ8.44 (d, J=4.1 Hz, 1H), 7.76 (td, J=7.7, 1.9 Hz, 1H), 7.51 (d, J=8.1 Hz, 1H), 7.26 (d, J=2.3 Hz, 1H), 7.25-7.22 (m, 1H), 7.14 (dd, J=8.4, 2.2 Hz, 1H), 6.97 (d, J=8.4 Hz, 1H), 6.81 (dt, J=15.0, 7.3 Hz, 1H), 6.67 (dd, J=16.0, 8.4 Hz, 1H), 6.52 (d, J=16.0 Hz, 1H), 6.02 (d, J=15.4 Hz, 1H), 5.21 (dd, J=9.5, 4.0 Hz, 1H), 4.58 (dd, J=8.1, 6.9 Hz, 1H), 3.84 (s, 3H), 3.68 (dt, J=8.7, 4.7 Hz, 1H), 3.48 (dd, J=13.5, 6.6 Hz, 1H), 3.33-3.30 (s, 2H), 3.21 (dd, J=13.5, 7.0 Hz, 1H), 3.05-2.99 (m, 3H), 2.85 (dd, J=13.8, 8.1 Hz, 1H), 2.71 (h, J=7.0 Hz, 1H), 2.51-2.44 (m, 1H), 2.44-2.37 (m, 1H), 2.37-2.29 (m, 1H), 1.91 (s, 3H), 1.81-1.69 (m, 2H), 1.67-1.59 (m, 1H), 1.18 (d, J=6.9 Hz, 3H), 1.11 (d, J=7.2 Hz, 3H), 0.95 (d, J=6.5 Hz, 3H), 0.92 (d, J=6.5 Hz, 3H). $^{13}$C NMR (150 MHz, CD$_3$OD) δ 200.34, 175.09, 173.49, 173.42, 168.05, 157.30, 155.43, 149.71, 143.29, 138.74, 138.61, 131.92, 131.56, 131.35, 129.85, 126.27, 123.36, 122.32, 113.42, 111.43, 78.67, 75.12, 56.61, 56.25, 44.08, 42.75, 41.97, 40.60, 39.87, 38.75, 38.09, 28.61, 25.76, 23.46, 22.54, 21.99, 17.10, 14.86; HRMS (ES) calculated for C$_{38}$H$_{51}$ClN$_4$O$_8$S [M+H] 759.3189, found 759.3184.

(S)-1-((2-acetamidoethyl)thio)-4-methyl-1-oxopentan-2-yl (R)-3-((R)-3-(3-chloro-4-methoxyphenyl)-2-((2E,5S,6R,7E)-5-hydroxy-6-methyl-8-(pyridin-3-yl)octa-2,7-dienamido)propanamido)-2-methylpropanoate (23c).

Reaction was run as per general coupling procedure, and purified by the flash chromatography system (1-10% Methanol/DCM) R$_f$=0.65 (10% Methanol/DCM). This was then deprotected as per general deprotection procedure and purified by the flash chromatography system (2-15% Methanol/DCM, 7:1) to afford the final product 23c (0.037 g, 51% yield over 3 steps, 7:1 dr) as a clear and colorless oil: R$_f$=0.25 (10% Methanol/DCM); $^1$H NMR (600 MHz, CD$_3$OD) δ8.52 (d, J=2.2 Hz, 1H), 8.36 (dd, J=4.9, 1.6 Hz, 1H), 7.89 (dt, J=8.1, 1.9 Hz, 1H), 7.37 (ddd, J=8.0, 4.9, 0.9 Hz, 1H), 7.26 (d, J=2.2 Hz, 1H), 7.14 (dd, J=8.4, 2.3 Hz, 1H), 6.97 (d, J=8.5 Hz, 1H), 6.81 (dt, J=15.2, 7.3 Hz, 1H), 6.46 (d, J=16.1 Hz, 1H), 6.41 (dd, J=16.0, 7.9 Hz, 1H), 6.02 (d, J=15.4 Hz, 1H), 5.21 (dd, J=9.5, 4.0 Hz, 1H), 4.59 (dd, J=8.0, 6.8 Hz, 1H), 3.84 (s, 3H), 3.67 (dt, J=8.0, 4.6 Hz, 1H), 3.48 (dd, J=13.5, 6.6 Hz, 1H), 3.33-3.30 (m, 2H) 3.20 (dd, J=13.5, 6.9 Hz, 1H), 3.04-3.00 (m, 3H) 2.85 (dd, J=13.7, 8.1 Hz, 1H) 2.70 (h, J=7.0 Hz, 1H), 2.51-2.36 (m, 2H), 2.36-2.28 (m, 1H), 1.91 (s, 3H), 1.83-1.68 (m, 2H), 1.65-1.61 (m, 1H), 1.17 (d, J=6.9 Hz, 3H), 1.10 (d, J=7.1 Hz, 3H), 0.95 (d, J=6.5 Hz, 3H), 0.92 (d, J=6.5 Hz, 3H); $^{13}$C NMR(150 MHz, CD$_3$OD) δ 200.34, 175.08, 173.48, 173.42, 168.04, 155.42, 148.27, 148.22, 143.30, 136.34, 135.52, 134.79, 131.91, 131.53, 129.85, 127.95, 126.19, 125.24, 123.23, 113.41, 78.66, 75.16, 56.60, 56.24, 44.33, 42.75, 41.97, 40.59, 39.86, 38.87, 38.08, 28.60, 25.76, 23.47, 22.54, 21.99, 17.34, 14.86; HRMS (ES) calculated for C$_{38}$H$_{51}$ClN$_4$O$_8$S [M+H] 759.3189, found 759.3192.

(S)-1-((2-acetamidoethyl)thio)-4-methyl-1-oxopentan-2-yl (R)-3-((R)-3-(3-chloro-4-methoxyphenyl)-2-((2E,5S,6R,7E)-5-hydroxy-6-methyl-8-(pyridin-4-yl)octa-2,7-dienamido)propanamido)-2-methylpropanoate (23e).

Reaction was run as per general coupling procedure, and purified by the flash chromatography system (1-10% Methanol/DCM) R$_f$=0.65 (10% Methanol/DCM). This was then deprotected as per general deprotection procedure and purified by the flash chromatography system (2-15% Methanol/DCM) to afford the final product 23e (0.048 g, 49% yield over 3 steps, 11:1 dr) as a clear and colorless oil: R$_f$=0.25 (10% Methanol/DCM); $^1$H NMR (600 MHz, CD$_3$OD) δ8.42 (d, J=6.3 Hz, 1H), 7.40 (d, J=6.3 Hz, 1H), 7.25 (d, J=2.2 Hz, 1H), 7.14 (dd, J=8.5, 2.2 Hz, 1H), 6.97 (d, J=8.4 Hz, 1H), 6.80 (dt, J=15.0, 7.3 Hz, 1H), 6.61 (dd, J=16.0, 8.5 Hz, 1H), 6.44 (d, J=15.9 Hz, 1H), 6.01 (d, J=15.4 Hz, 1H), 5.21 (dd, J=9.5, 4.0 Hz, 1H), 4.58 (dd, J=8.1, 6.9 Hz, 1H), 3.84 (s, 3H), 3.67 (dt, J=7.9, 4.7 Hz, 1H), 3.48 (dd, J=13.5, 6.6 Hz, 1H), 3.33-3.30 (m, 2H) 3.20 (dd, J=13.5, 7.0 Hz, 1H), 3.04-3.00 (m, 3H), 2.85 (dd, J=13.8, 8.1 Hz, 1H), 2.70 (h, J=6.9 Hz, 1H), 2.51-2.42 (m, 1H), 2.42-2.25 (m, 2H), 1.91 (s, 3H), 1.82-1.68 (m, 2H), 1.63 (ddd, J=13.1, 8.1, 4.0 Hz, 1H), 1.17 (d, J=6.8 Hz, 3H), 1.10 (d, J=7.1 Hz, 3H), 0.94 (d, J=6.5 Hz, 3H), 0.92 (d, J=6.5 Hz, 3H). $^{13}$C NMR(150 MHz, CD$_3$OD) δ 200.34, 175.08, 173.48, 173.42, 168.02, 155.43, 150.20, 147.73, 143.18, 139.50, 131.92, 131.53, 129.84, 129.42, 126.25, 123.24, 122.39, 113.42, 78.67, 75.03, 56.61, 56.23, 44.30, 42.75, 41.97, 40.60, 39.87, 38.90, 38.09, 28.61, 25.76, 23.46, 22.54, 21.99, 17.19, 14.86.; HRMS (ES) calculated for C$_{38}$H$_{51}$ClN$_4$O$_8$S [M+H] 759.3189, found 759.3187.

(S)-1-((2-acetamidoethyl)thio)-4-methyl-1-oxopentan-2-yl (R)-3-((R)-3-(3-chloro-4-methoxyphenyl)-2-((2E,5S,6R,7E)-5-hydroxy-6-methyl-8-(pyrazin-2-yl)octa-2,7-dienamido)propanamido)-2-methylpropanoate (23q).

Reaction was run as per general coupling procedure, and purified by the flash chromatography system (1-10% Methanol/DCM) R$_f$=0.65 (10% Methanol/DCM). This was then deprotected as per general deprotection procedure and purified by the flash chromatography system (2-15% Methanol/DCM) to afford the final product 23g (0.021 g, 25% yield over 3 steps, 9:1 dr) as a clear and colorless oil: R$_f$=0.25 (10% Methanol/DCM); $^1$F1 NMR (400 MHz, CD$_3$OD) δ 8.62 (s, 1H), 8.51 (s, 1H), 8.39 (d, J=2.6 Hz, 1H), 7.26 (d, J=2.0 Hz, 1H), 7.14 (dd, J=8.5, 2.1 Hz, 1H), 6.97 (d, J=8.4 Hz, 1H), 6.93 (dd, J=15.9, 8.5 Hz, 1H), 6.81 (dt, J=14.9, 7.3 Hz, 1H), 6.57 (d, J=16.0 Hz, 1H), 6.02 (d, J=15.4 Hz, 1H), 5.21 (dd, J=9.4, 3.9 Hz, 1H), 4.58 (t, J=7.5 Hz, 1H), 3.69 (dt, J=9.0, 4.7 Hz, 1H), 3.48 (dd, J=13.4, 6.6 Hz, 1H), 3.37-3.24 (m, 2H), 3.20 (dd, J=13.5, 7.1 Hz, 1H), 3.07-2.97 (m, 1H), 3.03 (t, J=6.8 Hz, 2H), 2.85 (dd, J=13.7, 8.2 Hz, 1H), 2.70 (h, J=6.9 Hz, 1H), 2.56-2.42 (m, 1H), 2.41-2.25 (m, 2H) 1.91 (s, 3H), 1.82-1.68 (m, 2H), 1.62 (ddd, J=13.1, 8.1, 3.9 Hz, 1H), 1.19 (d, J=6.8 Hz, 3H), 1.10 (d, J=7.0 Hz, 3H), 0.95 (d, J=6.3 Hz, 3H), 0.92 (d, J=6.3 Hz, 3H). $^{13}$C NMR (151 MHz, CD$_3$OD) δ 200.34, 175.08, 173.47, 173.42, 168.03, 155.42, 153.09, 145.39, 143.89, 143.46, 143.20, 141.38, 131.91, 131.54, 129.86, 128.22, 126.28, 123.24, 113.42, 78.67, 75.01, 56.62, 56.24, 44.21, 42.75, 41.97, 40.60, 39.86, 38.80, 38.09, 28.61, 25.76, 23.46, 22.54, 21.99, 16.99, 14.86. HRMS (ES) calculated for C$_{37}$H$_{50}$ClN$_5$O$_8$S [M+H] 760.3141, found 760.3143.

(S)-1-((2-acetamidoethyl)thio)-4-methyl-1-oxopentan-2-yl (R)-3-((R)-3-(3-chloro-4-methoxyphenyl)-2-((2E,5S,6R,7E)-5-hydroxy-6-methyl-8-(1-methyl-1H-pyrazol-5-yl)octa-2,7-dienamido)propanamido)-2-methylpropanoate (23h).

Reaction was run as per general coupling procedure, and purified by the flash chromatography system (1-10% Methanol/DCM) R$_f$=0.65 (10% Methanol/DCM). This was then deprotected as per general deprotection procedure and purified by the flash chromatography system (2-15% Methanol/DCM) to afford the final product 23h (0.022, 29% yield over 3 steps, 9:1 dr) as a clear and colorless oil: R$_f$=0.25 (10% Methanol/DCM); $^1$H NMR (600 MHz, CD$_3$OD) δ 7.34 (d, J=2.2 Hz, 1H), 7.25 (d, J=2.2 Hz, 1H), 7.14 (dd, J=8.4, 2.2 Hz, 1H), 6.97 (d, J=8.5 Hz, 1H), 6.81 (dt, J=15.0, 7.3 Hz, 1H), 6.42 (d, J=15.9 Hz, 1H), 6.38 (d, J=2.1 Hz, 1H), 6.25 (dd, J=15.9, 8.6 Hz, 1H), 6.01 (dd, J=15.4, 1.5 Hz, 1H), 5.21 (dd, J=9.5, 3.9 Hz, 1H), 4.58 (dd, J=8.1, 7.0 Hz, 1H), 3.84 (s, 3H), 3.82 (s, 3H), 3.65 (dt, J=8.0, 4.6 Hz, 1H), 3.48 (dd, J=13.5, 6.6 Hz, 1H), 3.33-3.30 (m, 2H) 3.20 (dd, J=13.5, 7.0 Hz, 1H), 3.03 (td, J=6.6, 1.8 Hz, 2H), 3.03-3.00 (m, 1H) 2.85 (dd, J=13.8, 8.1 Hz, 1H), 2.70 (h, J=6.9 Hz, 1H), 2.50-2.36 (m, 2H), 2.36-2.28 (m, 1H), 1.91 (s, 3H), 1.82 -1.68 (m, 2H), 1.63 (ddd, J=13.2, 8.1, 3.9 Hz, 1H), 1.15 (d, J=6.9 Hz, 3H), 1.10 (d, J=7.1 Hz, 3H), 0.95 (d, J=6.4 Hz, 3H), 0.92 (d, J=6.5 Hz, 3H). $^{13}$C NMR: (150 MHz, CD$_3$OD) δ 200.34, 175.07, 173.47, 173.41, 168.03, 155.41, 143.25, 142.84, 139.10, 137.95, 131.90, 131.51, 129.84, 126.20, 123.21, 118.41, 113.40, 103.56, 78.66, 75.00, 56.60, 56.24, 44.34, 42.74, 41.96, 40.59, 39.86, 38.86, 38.09, 28.60, 25.75, 23.47, 22.54, 21.99, 17.31, 14.87; HRMS (ES) calculated for C$_{37}$H$_{52}$ClN$_5$O$_8$S [M+H] 762.3298, found 762.3295.

(S)-1-((2-acetamidoethyl)thio)-4-methyl-1-oxopentan-2-yl (R)-3-((R)-3-(3-chloro-4-methoxyphenyl)-2-((2E,5S,6R,7E)-5-hydroxy-6-methyl-8-(1-methyl-1H-pyrazol-3-yl)octa-2,7-dienamido) propanamido)-2-methylpropanoate (23i).

Reaction was run as per general coupling procedure, and purified by the flash chromatography (1-10% Methanol/DCM) R$_f$=0.65 (10% Methanol/DCM). This was then deprotected as per general deprotection procedure and purified by the flash chromatography (2-15% Methanol/DCM) to afford the final product 23i (0.019 g, 34% yield over 3 steps, 11:1 dr) as a clear and colorless oil: R$_f$=0.25 (10% Methanol/DCM); $^1$H NMR (600 MHz, CD$_3$OD) δ 7.46 (d, J=2.3 Hz, 1H), 7.26 (d, J=2.1 Hz, 1H), 7.14 (dd, J=8.5, 2.2 Hz, 1H), 6.97 (d, J=8.4 Hz, 1H), 6.79 (dt, J=15.1, 7.3 Hz, 1H), 6.34 (d, J=2.4 Hz, 1H), 6.32 (d, J=16.6 Hz, 1H), 6.21 (dd, J=16.1, 8.4 Hz, 1H), 6.01 (d, J=15.4 Hz, 1H), 5.21 (dd, J=9.5, 4.0 Hz, 1H), 4.58 (dd, J=8.1, 7.0 Hz, 1H), 3.84 (s, 6H), 3.63 (dt, J=8.7, 4.6 Hz, 1H), 3.48 (dd, J=13.5, 6.6 Hz, 1H), 3.33-3.29 (m, 2H), 3.20 (dd, J=13.5, 7.0 Hz, 1H), 3.05-2.99 (m, 3H), 2.85 (dd, J=13.7, 8.1 Hz, 1H), 2.70 (h, J=7.0 Hz, 1H), 2.41-2.33 (m, 2H), 2.30 (dt, J=15.4, 7.8 Hz, 1H), 1.91 (s, 3H), 1.82-1.68 (m, 2H), 1.63 (ddd, J=13.2, 8.1, 3.9 Hz, 1H), 1.13 (d, J=6.9 Hz, 3H), 1.10 (d, J=7.2 Hz, 3H), 0.95 (d, J=6.5 Hz, 3H), 0.92 (d, J=6.4 Hz, 3H). $^{13}$C NMR: (150 MHz, CD$_3$OD) δ200.35, 175.08, 173.50, 173.43, 168.07, 155.42, 152.17, 143.44, 134.45, 133.02, 131.91, 131.54, 129.87, 126.17, 123.62, 123.23, 113.39, 103.27, 78.65, 75.19, 56.59, 56.27, 44.02, 42.75, 41.97, 40.59, 39.86, 38.72, 38.60, 38.09, 28.59, 25.76, 23.47, 22.54, 21.98, 17.24, 14.86. HRMS (ES) calculated for C$_{37}$H$_{52}$ClN$_5$O$_8$S [M+H] 762.3298, found 762.3295.

(S)-1-((2-acetamidoethyl)thio)-4-methyl-1-oxopentan-2-yl (R)-3-((R)-3-(3-chloro-4-methoxyphenyl)-2-((2E,5S,6R,7E)-5-hydroxy-6-methyl-8-(1-methyl-1H-pyrazol-4-yl)octa-2,7-dienamido)propanamido)-2-methylpropanoate (23j).

Reaction was run as per general coupling procedure, and purified by the flash chromatography system (1-10% Methanol/DCM) R$_f$=0.65 (10% Methanol/DCM). This was then deprotected as per general deprotection procedure and purified by the flash chromatography system (2-15% Methanol/DCM) to afford the final product 23j (0.065 g, 48% yield over 3 steps, 11:1 dr) as a clear and colorless oil: R$_f$=0.25 (10% Methanol/DCM); $^1$H NMR (600 MHz, CD$_3$OD) δ 7.54 (s, 1H), 7.50 (s, 1H), 7.25 (d, J=2.1 Hz, 1H), 7.13 (dd, J=8.2, 2.1 Hz, 1H), 6.97 (d, J=8.3 Hz, 1H), 6.80 (dt, J=15.0, 7.3 Hz, 1H), 6.22 (d, J=16.0 Hz, 1H), 6.00 (d, J=16.1, 1H), 5.94 (dd, J=16.0, 8.4 Hz, 1H), 5.21 (dd, J=9.5, 4.0 Hz, 1H), 4.58 (t, J=7.5 Hz, 1H), 3.84 (s, 3H), 3.84 (s, 3H), 3.60 (dt, J=8.5, 4.5 Hz, 1H), 3.48 (dd, J=13.5, 6.6 Hz, 1H), 3.33-3.30 (m, 2H), 3.20 (dd, J=13.5, 6.9 Hz, 1H), 3.03 (t, J=5.8 Hz, 2H), 3.03-3.00 (m, 1H), 2.85 (dd, J=13.7, 8.2 Hz, 1H), 2.70 (h, J=7.0 Hz, 1H), 2.40-2.23 (m, 3H), 1.91 (s, 3H), 1.81-1.68 (m, 2H), 1.63 (td, J=9.2, 8.6, 4.4 Hz, 1H), 1.10 (d, J=7.0 Hz, 6H), 0.95 (d, J=6.3 Hz, 3H), 0.92 (d, J=6.3 Hz, 3H). $^{13}$C NMR (150 MHz, CD$_3$OD) δ 200.35, 175.08, 173.49, 173.42, 168.10, 155.43, 143.57, 137.72, 131.92, 131.54, 130.89, 129.84, 129.39, 126.05, 123.24, 122.47, 121.60, 113.42, 78.67, 75.39, 56.61, 56.24, 44.14, 42.75, 41.97, 40.60, 39.86, 38.71, 38.65, 38.08, 28.60, 25.76, 23.46, 22.54, 21.99, 17.38, 14.86. HRMS (ES) calculated for C$_{37}$H$_{52}$ClN$_5$O$_8$S [M+H] 762.3298, found 762.3294.

(S)-1-((2-acetamidoethyl)thio)-4-methyl-1-oxopentan-2-yl (R)-3-((R)-3-(3-chloro-4-methoxyphenyl)-2-((2E,5S,6R,7E)-5-hydroxy-8-(1-isopropyl-1H-pyrazol-4-yl)-6-methylocta-2,7-dienamido) propanamido)-2-methylpropanoate (23l).

Reaction was run as per general coupling procedure, and purified by the flash chromatography (1-10% Methanol/

DCM) R$_f$=0.65 (10% Methanol/DCM). This was then deprotected as per general deprotection procedure and purified by the flash chromatography (2-15% Methanol/DCM) to afford the final product 23l (0.025, 38% yield over 3 steps, 9:1 dr) as a clear and colorless oil: R$_f$=0.25 (10% Methanol/DCM); $^1$H NMR (600 MHz, CD$_3$OD) δ 7.64 (s, 1H), 7.51 (s, 1H), 7.25 (d, J=2.2 Hz, 1H), 7.14 (dd, J=8.4, 2.2 Hz, 1H), 6.97 (d, J=8.4 Hz, 1H), 6.80 (dt, J=15.0, 7.3 Hz, 1H), 6.23 (d, J=16.0 Hz, 1H), 6.00 (d, J=15.4 Hz, 1H), 5.94 (dd, J=16.0, 8.5 Hz, 1H), 5.21 (dd, J=9.5, 4.0 Hz, 1H), 4.58 (t, J=7.5 Hz, 1H), 4.46 (hept, J=6.6 Hz, 1H), 3.84 (s, 3H), 3.61 (dt, J=8.6, 4.5 Hz, 1H), 3.48 (dd, J=13.5, 6.6 Hz, 1H), 3.33-3.30 (m, 2H), 3.20 (dd, J=13.5, 7.0 Hz, 1H), 3.03 (t, J=6.6 Hz, 2H), 3.03-3.00 (m, 1H), 2.85 (dd, J=13.8, 8.1 Hz, 1H), 2.70 (h, J=6.9 Hz, 1H), 2.43-2.23 (m, 3H), 1.91 (s, 3H), 1.82-1.69 (m, 2H), 1.63 (ddd, J=13.2, 8.1, 3.9 Hz, 1H), 1.47 (d, J=6.7 Hz, 6H), 1.11 (d, J=6.9 Hz, 3H), 1.10 (d, J=7.1 Hz, 3H), 0.95 (d, J=6.4 Hz, 3H), 0.92 (d, J=6.4 Hz, 3H). $^{13}$C NMR (150 MHz, CD$_3$OD) δ200.36, 175.08, 173.49, 173.44, 168.11, 155.42, 143.59, 137.30, 131.92, 131.52, 130.64, 129.85, 126.04 (2), 123.22, 121.90, 121.82, 113.39, 78.65, 75.41, 56.59, 56.24, 54.99, 44.15, 42.74, 41.97, 40.59, 39.86, 38.67, 38.07, 28.59, 25.76, 23.48, 23.08, 22.54, 21.97, 17.44, 14.86. HRMS (ESI) calculated for C$_{39}$H$_{56}$ClN$_5$O$_8$S [M+H] 790.3611, found 790.3608.

(S)-1-((2-acetamidoethyl)thio)-4-methyl-1-oxopentan-2-yl (R)-3-((R)-3-(3-chloro-4-methoxyphenyl)-2-((2E,5S,6R,7E)-8-(3,5-dimethylisoxazol-4-yl)-5-hydroxy-6-methylocta-2,7-dienamido)propanamido)-2-methylpropanoate (23m).

Reaction was run as per general coupling procedure, and purified by the flash chromatography (1-10% Methanol/DCM) R$_f$=0.65 (10% Methanol/DCM). This was then deprotected as per general deprotection procedure and purified by the flash chromatography (2-15% Methanol/DCM) to afford the final product 23m (0.015 g, 43% yield over 3 steps, 8:1 dr) as a clear and colorless oil: R$_f$=0.25 (10% Methanol/DCM); $^1$H NMR (600 MHz, CD$_3$OD) δ 7.25 (d, J=2.1 Hz, 1H), 7.14 (dd, J=8.4, 2.2 Hz, 1H), 6.97 (d, J=8.4 Hz, 1H), 6.81 (dt, J=15.0, 7.3 Hz, 1H), 6.14 (d, J=16.3 Hz, 1H), 6.01 (d, J=15.4 Hz, 1H), 5.93 (dd, J=16.3, 8.5 Hz, 1H), 5.21 (dd, J=9.5, 4.0 Hz, 1H), 4.57 (t, J=7.5 Hz, 1H), 3.84 (s, 3H), 3.63 (dt, J=8.5, 4.7 Hz, 1H), 3.48 (dd, J=13.5, 6.6 Hz, 1H), 3.33-3.30 (m, 2H) 3.20 (dd, J=13.5, 7.0 Hz, 1H), 3.03 (t, J=6.8 Hz, 2H), 3.02-2.99 (m, 1H) 2.85 (dd, J=13.7, 8.1 Hz, 1H), 2.70 (h, J=7.0 Hz, 1H), 2.39 (s, 3H), 2.38-2.30 (m, 3H), 2.28 (s, 3H), 1.91 (s, 3H), 1.82-1.67 (m, 2H), 1.63 (ddd, J=12.6, 8.2, 3.9 Hz, 1H), 1.14 (d, J=6.8 Hz, 3H), 1.10 (d, J=7.1 Hz, 3H), 0.95 (d, J=6.4 Hz, 3H), 0.92 (d, J=6.4 Hz, 3H). $^{13}$C NMR (150 MHz, CD$_3$OD) δ200.36, 175.08, 173.49, 173.44, 168.04, 166.54, 159.73, 155.42, 143.35, 135.53, 131.90, 131.50, 129.85, 126.13, 123.22, 119.18, 114.25, 113.38, 78.65, 75.09, 56.59, 56.26, 44.85, 42.74, 41.97, 40.59, 39.86, 38.94, 38.09, 28.59, 25.76, 23.48, 22.53, 21.97, 17.69, 14.86, 11.47, 11.29. HRMS (ES) calculated for C$_{38}$H$_{53}$ClN$_4$O$_9$S [M+H] 777.3295, found 777.3293.

7. Gem Dimethyl Seco Cryptophycins (S)-1((2-acetamidoethyl)thio)-4-methyl-1-oxopentan-2-yl 3-((R)-3-(3-chloro-4-methoxyphenyl)-2-((2E,5S,6R,7E)-5-hydroxy-6-methyl-8-(pyridin-3-yl)octa-2,7-dienamido)propanamido)-2,2-dimethylpropanoate (23d).

Reaction was run as per general coupling procedure, and purified by the flash chromatography system (1-10% Methanol/DCM) R$_f$=0.65 (10% Methanol/DCM). This was then deprotected as per general deprotection procedure and purified by the flash chromatography system (2-15% Methanol/DCM) to afford the final product 23d (0.019 g, 51% yield over 3 steps, 10:1 dr) as a clear and colorless oil: R$_f$=0.25 (10% Methanol/DCM); $^1$H NMR (600MHz, CD$_3$OD) δ 8.52 (d, J=2.3 Hz, 1H), 8.35 (dd, J=4.8, 1.6 Hz, 1H), 7.89 (dt, J=8.0, 2.0 Hz, 1H), 7.37 (dd, J=8.0, 4.9 Hz, 1H), 7.28 (d, J=2.2 Hz, 1H), 7.15 (dd, J=8.4, 2.3 Hz, 1H), 6.96 (d, J=8.5 Hz, 1H), 6.80 (dt, J=15.0, 7.3 Hz, 1H), 6.46 (d, J=16.1 Hz, 1H), 6.40 (dd, J=16.0, 7.9 Hz, 1H), 6.01 (d, J=15.4 Hz, 1H), 5.20 (dd, J=9.5, 3.8 Hz, 1H), 4.65 (dd, J=8.5, 6.5 Hz, 1H), 3.92 (p, J=6.2 Hz, 2H), 3.83 (s, 3H), 3.66 (dt, J=8.7, 4.6 Hz, 1H), 3.44-3.36 (m, 2H), 3.33-3.29 (m, 2H), 3.11-3.00 (m, 3H), 2.85 (dd, J=13.9, 8.5 Hz, 1H), 2.44 (td, J=7.2, 4.3 Hz, 1H), 2.39 (dt, J=13.0, 6.4 Hz, 1H), 2.32 (dt, J=14.9, 7.6 Hz, 1H), 1.91 (s, 3H), 1.83-1.69 (m, 2H), 1.64 (ddd, J=13.4, 8.4, 3.9 Hz, 1H), 1.14 (s, 3H) 1.14 (d, 3H), 1.13 (d, 3H), 0.95 (d, J=6.5 Hz, 3H), 0.92 (d, J=6.4 Hz, 3H). $^{13}$C NMR (150 MHz, CD$_3$OD) δ200.53, 176.86, 173.76, 173.42, 168.17, 155.38, 148.26, 148.21, 143.36, 136.35, 135.52, 134.80, 131.89, 131.69, 129.82, 127.96, 126.16, 125.25, 123.23, 113.41, 78.81, 75.15, 64.74, 56.61, 56.39, 47.89, 44.69, 44.31, 41.94, 39.86, 38.88, 37.86, 28.73, 25.87, 25.26, 23.49, 23.26, 23.18, 22.59, 21.95, 17.35. HRMS (ES) calculated for C$_{39}$H$_{53}$ClN$_4$O$_8$S [M+H] 773.3345, found 773.3353.

(S)-1((2-acetamidoethyl)thio)-4-methyl-1-oxopentan-2-yl 3-((R)-3-(3-chloro-4-methoxyphenyl)-2-((2E,5S,6R,7E)-5-hydroxy-6-methyl-8-(pyridin-4-yl)octa-2,7-dienamido)propanamido)-2,2-dimethylpropanoate (23f).

Reaction was run as per general coupling procedure, and purified by the flash chromatography system (1-10% Methanol/DCM) R$_f$=0.65 (10% Methanol/DCM). This was then deprotected as per general deprotection procedure and purified by the flash chromatography system (2-15% Methanol/DCM) to afford the final product 23f (0.039 g, 45% yield over 3 steps, 12:1 dr) as a clear and colorless oil: R$_f$=0.25 (10% Methanol/DCM); $^1$H NMR (600MHz, CD$_3$OD) δ8.41 (d, J=6.1 Hz, 1H), 7.40 (d, J=6.1 Hz, 1H), 7.27 (d, J=1.9 Hz, 1H), 7.15 (dd, J=8.5, 2.2 Hz, 1H), 6.96 (dd, J=8.5, 1.0 Hz, 1H), 6.79 (dt, J=14.5, 7.1 Hz, 1H), 6.61 (dd, J=16.0, 8.5 Hz, 1H), 6.43 (d, J=16.0 Hz, 1H), 6.00 (d, J=15.4 Hz, 1H), 5.20 (dd, J=9.5, 3.8 Hz, 1H), 4.65 (dd, J=8.4, 6.6 Hz, 1H), 3.83 (s, 3H), 3.66 (dt, J=8.5, 4.4 Hz, 1H), 3.40 (d, J=13.6 Hz, 1H), 3.36 (d, J=12.9 Hz, 1H), 3.32-3.29 (m, 2H), 3.12-2.99 (m, 3H), 2.85 (dd, J=14.0, 8.5 Hz, 1H), 2.51-2.42 (m, 1H), 2.41-2.34 (m, 1H), 2.35-2.27 (m, 1H), 1.90 (s, 3H), 1.81-1.68 (m, 2H), 1.68-1.60 (m, 1H), 1.16 (s, 6H), 1.15 (d, J=5.1 Hz, 3H), 0.95 (d, J=6.5 Hz, 3H), 0.92 (d, J=6.5 Hz, 3H). $^{13}$C NMR (150 MHz, CD$_3$OD) δ200.53, 176.86, 173.67, 173.42, 168.14, 155.38, 150.15, 147.78, 143.23, 139.54, 131.90, 131.68, 129.81, 129.42, 126.21, 123.24, 122.41, 113.43, 78.81, 75.01, 56.61, 56.33, 47.78, 44.69, 44.28, 41.94, 39.86, 38.92, 37.86, 28.73, 25.87, 23.49, 23.26, 23.18, 22.59, 21.95, 17.20.; HRMS (ES) calculated for C$_{39}$H$_{53}$ClN$_4$O$_8$S [M+H] 773.3345, found 773.3353.

(S)-1((2-acetamidoethyl)thio)-4-methyl-1-oxopentan-2-yl 3-((R)-3-(3-chloro-4-methoxyphenyl)-2-((2E,5S,6R,7E)-5-hydroxy-6-methyl-8-(1-methyl-1H-pyrazol-4-yl)octa-2,7-dienamido)propanamido)-2,2-dimethylpropanoate (23k).

Reaction was run as per general coupling procedure, and purified by the flash chromatography system (1-10% Methanol/DCM) R_f=0.65 (10% Methanol/DCM). This was then deprotected as per general deprotection procedure and purified by the flash chromatography system (2-15% Methanol/DCM) to afford the final product 23k (0.060, 41% yield over 3 steps, 10:1) as a clear and colorless oil: R_f=0.25 (10% Methanol/DCM); $^1$H NMR (600MHz, CD$_3$OD) δ 7.55 (s, 1H), 7.50 (s, 1H), 7.28 (d, J=2.1 Hz, 1H), 7.15 (dd, J=8.5, 2.2 Hz, 1H), 6.96 (d, J=8.5 Hz, 1H), 6.79 (dt, J=14.9, 7.3 Hz, 1H), 6.21 (d, J=16.1 Hz, 1H), 5.99 (d, J=15.4 Hz, 1H), 5.93 (dd, J=16.0, 8.4 Hz, 1H), 5.20 (dd, J=9.6, 3.9 Hz, 1H), 4.65 (dd, J=8.6, 6.5 Hz, 1H), 3.84 (s, 3H), 3.83 (s, 3H), 3.60 (dt, J=8.8, 4.6 Hz, 1H), 3.40 (d, J=13.5 Hz, 1H), 3.35 (d, J=13.9 Hz, 1H), 3.33-3.29 (m, 2H), 3.12-2.98 (m, 3H), 2.85 (dd, J=13.9, 8.6 Hz, 1H), 2.32 (m, 3H), 1.91 (s, 3H), 1.83-1.68 (m, 2H), 1.64 (ddd, J=12.8, 8.4, 3.8 Hz, 1H), 1.16 (s, 6H), 1.10 (d, J=6.9 Hz, 3H), 0.96 (d, J=6.5 Hz, 3H), 0.92 (d, J=6.5 Hz, 3H). $^{13}$C NMR (150 MHz, CD$_3$OD) δ200.54, 176.85, 173.68, 173.44, 168.22, 155.38, 143.62, 137.71, 131.90, 131.68, 130.86, 129.81, 129.39, 126.00, 123.23, 122.47, 121.60, 113.40, 78.80, 75.37, 56.60, 56.35, 47.77, 44.68, 44.12, 41.94, 39.86, 38.72, 38.67, 37.85, 28.73, 25.87, 23.49, 23.25, 23.17, 22.59, 21.94, 17.40. HRMS (ES) calculated for C$_{38}$H$_{54}$ClN$_5$O$_8$S [M+H] 776.3454, found 776.3457.

8. Biocatalytic Cryptophycin Synthesis and Analogue Characterization

General Procedure Analytical Scale Reactions.

To a 1.5 mL Eppendorf tube was added phosphate buffer (pH=7.2, 100 mM, 300 μL), DMSO (5%) and seco substrate (50 μM) suspended in DMSO. This was then treated with CrpTE enzyme (in phosphate buffer pH=7.2 100 mM, 0.5 μM) and shaken at 30° C. for 12 hours. Upon completion of the reaction, the aqueous layer was extracted with 0.300 mL of Ethyl Acetate, 150 μL was removed, dried directly into an HPLC vial, and resuspended in 70 μL of Methanol. This was used for analysis on the TOF-MS.

General Procedure semi Preparative Scale Reactions.

To a 250 mL Erlenmeyer flask was added DMSO (5%), and substrate (75 μM) suspended in DMSO. This was diluted with phosphate buffer (pH=7.2, 100 mM) and warmed to 30° C. for 20 minutes prior to treatment with CrpTE enzyme (0.5 μM). The reaction was allowed to shake at 100 RPM at 30° C. for 12 hours, prior to 1:1v/v dilution with acetone, and chilling to −20° C. in the freezer. The precipitated protein was filtered through celite, washed with acetone, organics removed under reduced pressure, and the remaining aqueous layer was extracted with DCM 3×20 mL. The organics were combined, dried over sodium sulfate, filtered, and concentrated. The reactions were purified using a HydroRP C18 (250×10.0 mm, 4 micron) using a 20-80% water/acetonitrile gradient with a flow rate of 3 mL/minute.

(3S,6R,10R,16S,E)-10-(3-chloro-4-methoxybenzyl)-3-isobutyl-6-methyl-16-((R,E)-4-(pyridin-2-yl)but-3-en-2-yl)-1,4-dioxa-8,11-diazacyclohexadec-13-ene-2,5,9,12-tetraone (25b).

Reaction was run and purified as per general procedure for semi-preparative scale reaction. $^1$H NMR (600 MHz, CD$_3$OD) δ8.46 (dd, J=5.0, 0.9 Hz, 1H), 7.78 (td, J=7.7, 1.8 Hz, 1H), 7.48 (d, J=7.9 Hz, 1H), 7.28 (d, J=2.2 Hz, 1H), 7.26 (ddd, J=7.5, 5.0, 1.1 Hz, 1H), 7.17 (dd, J=8.5, 2.2 Hz, 1H), 6.98 (d, J=8.5 Hz, 1H), 6.71 (ddd, J=15.1, 11.1, 3.9 Hz, 1H), 6.61-6.57 (m, 2H), 5.93 (dd, J=15.1, 1.9 Hz, 1H), 5.09 (ddd, J=11.3, 6.9, 1.9 Hz, 1H), 4.93 (dd, J=9.9, 3.6 Hz, 1H), 4.52 (dd, J=11.3, 3.9 Hz, 1H), 3.84 (s, 3H), 3.58 (dd, J=13.8, 3.3 Hz, 1H), 3.27 (dd, J=13.8, 3.0 Hz, 1H), 3.18 (dd, J=14.5, 3.9 Hz, 1H), 2.80-2.73 (m, 2H), 2.73-2.65 (m, 2H), 2.39 (dt, J=14.5, 11.2 Hz, 1H), 1.69-1.52 (m, 2H), 1.34 (ddd, J=14.1, 8.8, 3.6 Hz, 1H), 1.18 (d, J=7.1 Hz, 6H), 0.74 (d, J=6.5 Hz, 3H), 0.71 (d, J=6.6 Hz, 3H). $^{13}$C NMR (151 MHz, CD$_3$OD) δ177.53, 174.04, 172.22, 168.33, 156.60, 155.36, 149.99, 143.41, 138.74, 137.58, 132.23, 132.10, 131.49, 129.28, 125.62, 123.71, 123.27, 122.82, 113.50, 78.48, 72.86, 57.35, 56.60, 43.46, 41.19, 40.88, 38.98, 37.99, 36.36, 5.62, 23.20, 21.66, 17.53, 15.06. HRMS (ES) calculated for C$_{34}$H$_{42}$ClN$_3$O$_7$ [M+H] 640.2784, found 640.2788.

(3S,6R,10R,16S,E)-10-(3-chloro-4-methoxybenzyl)-3-isobutyl-6-methyl-16-((R,E)-4-(pyridin-3-yl)but-3-en-2-yl)-1,4-dioxa-8,11-diazacyclohexadec-13-ene-2,5,9,12-tetraone (25c).

Reaction was run and purified as per general procedure for semi-preparative scale reaction. $^1$H NMR (600 MHz, CD$_3$OD) δ 8.53 (d, J=2.2 Hz, 1H), 8.38 (dd, J=4.8, 1.6 Hz, 1H), 7.92 (d, J=8.0 Hz, 1H), 7.40 (dd, J=8.0, 4.9 Hz, 1H), 7.28 (d, J=2.2 Hz, 1H), 7.17 (dd, J=8.4, 2.2 Hz, 1H), 6.98 (d, J=8.4 Hz, 1H), 6.71 (ddd, J=15.1, 11.2, 3.9 Hz, 1H), 6.53 (d, J=15.9 Hz, 1H), 6.30 (dd, J=15.9, 8.9 Hz, 1H), 5.93 (dd, J=15.2, 1.9 Hz, 1H), 5.08 (ddd, J=11.2, 7.2, 1.9 Hz, 1H), 4.93 (dd, J=9.9, 3.7 Hz, 1H), 4.52 (dd, J=11.2, 3.9 Hz, 1H), 3.84 (s, 3H), 3.58 (dd, J=13.8, 3.3 Hz, 1H), 3.27 (dd, J=13.8, 3.0 Hz, 1H), 3.18 (dd, J=14.5, 3.9 Hz, 1H), 2.80-2.63 (m, 4H), 2.37 (dt, J=14.4, 11.1 Hz, 1H), 1.69-1.55 (m, 2H), 1.31 (ddd, J=14.1, 8.9, 3.7 Hz, 1H), 1.19 (d, J=3.5 Hz, 3H), 1.18 (d, J=2.9 Hz, 3H), 0.74 (d, J=6.5 Hz, 3H), 0.70 (d, J=6.5 Hz, 3H). $^{13}$C NMR (150 MHz, CD$_3$OD) δ180.30, 177.53, 174.03, 172.21, 168.33, 155.36, 148.71, 148.40, 143.42, 135.55, 134.96, 134.86, 132.21, 131.49, 129.28, 128.77, 125.62, 125.40, 113.49, 78.47, 72.80, 57.36, 56.60, 43.75, 41.18, 40.94, 38.97, 37.88, 36.35, 25.60, 23.18, 21.69, 17.50, 15.06. HRMS (ES) calculated for C$_{34}$H$_{42}$ClN$_3$O$_7$ [M+H] 640.2784, found 640.2789

(3S,10R,16S,E)-10-(3-chloro-4-methoxybenzyl)-3-isobutyl-6,6-dimethyl-16-((R,E)-4-(pyridin-3-yl)but-3-en-2-yl)-1,4-dioxa-8,11-diazacyclohexadec-13-ene-2,5,9,12-tetraone (25d).

Reaction was run and purified as per general procedure for semi-preparative scale reaction. $^1$H NMR (600MHz, CD$_3$OD) δ 8.53 (s, 1H), 8.38 (d, J=4.7 Hz, 1H), 7.92 (dt, J=8.0, 1.9 Hz, 1H), 7.40 (dd, J=8.0, 4.8 Hz, 1H), 7.28 (d, J=2.2 Hz, 1H), 7.17 (dd, J=8.4, 2.2 Hz, 1H), 6.98 (d, J=8.4 Hz, 1H), 6.72 (ddd, J=15.2, 11.2, 3.9 Hz, 1H), 6.53 (d, J=15.9 Hz, 1H), 6.30 (dd, J=16.0, 8.9 Hz, 1H), 5.92 (dd, J=15.1, 1.9 Hz, 1H), 5.07 (ddd, J=11.1, 7.2, 1.8 Hz, 2H), 4.96 (dd, J=9.9, 3.4 Hz, 1H), 4.51 (dd, J=11.3, 3.8 Hz, 1H), 3.84 (s, 3H), 3.46 (d, J=13.6 Hz, 1H), 3.18 (dd, J=14.5, 3.8 Hz, 1H), 3.08 (d, J=13.7 Hz, 1H), 2.74 (dd, J=14.5, 11.4 Hz, 1H), 2.74-2.62 (m, 2H), 2.36 (dt, J=14.4, 11.2 Hz, 1H), 1.66-1.55 (m, 2H), 1.37-1.26 (m, 3H), 1.20 (s, 3H), 1.18 (d, J=6.9 Hz, 3H), 1.16 (s, 3H), 0.74 (d, J=6.4 Hz, 3H), 0.70 (d, J=6.4 Hz, 3H). $^{13}$C NMR (150 MHz, CD$_3$OD) δ180.03, 178.94, 173.68, 172.01, 168.22, 155.37, 148.71, 148.40, 143.63, 135.55, 134.85, 132.17, 131.46, 129.26, 128.78, 125.43, 123.28, 113.50, 78.43, 72.58, 57.48, 56.60, 47.39, 44.02, 43.75, 40.92, 37.92, 36.48, 31.64, 25.85, 23.32, 23.29, 23.22, 21.65, 17.49. HRMS (ES) calculated for C$_{35}$H$_{44}$ClN$_3$O$_7$ [M+H] 654.2941, found 654.2940.

(3S,6R,10R,16S,E)-10-(3-chloro-4-methoxybenzyl)-3-isobutyl-6-methyl-16-((R,E)-4-(pyridin-4-yl)but-3-en-2-yl)-1,4-dioxa-8,11-diazacyclohexadec-13-ene-2,5,9,12-tetraone (25e).

Reaction was run and purified as per general procedure for semi-preparative scale reaction. $^1$H NMR (600MHz, CD₃OD) δ8.43 (d, J=6.2 Hz, 2H), 7.42 (d, J=6.3 Hz, 2H), 7.27 (d, J=2.1 Hz, 1H), 7.15 (dd, J=8.5, 2.1 Hz, 1H), 6.96 (d, J=8.4 Hz, 1H), 6.69 (ddd, J=15.1, 11.1, 3.9 Hz, 1H), 6.50-6.47 (m, 2H), 5.91 (dd, J=15.2, 1.8 Hz, 1H), 5.08 (dd, J=10.7, 8.3 Hz, 1H), 4.90 (dd, J=9.9, 3.6 Hz, 1H), 4.51 (dd, J=11.2, 3.9 Hz, 1H), 3.82 (s, 3H), 3.56 (dd, J=13.8, 3.3 Hz, 1H), 3.25 (dd, J=13.8, 2.9 Hz, 1H), 3.16 (dd, J=14.5, 3.9 Hz, 1H), 2.77-2.62 (m, 4H), 2.34 (dt, J=14.7, 11.2 Hz, 1H), 1.67-1.51 (m, 2H), 1.28 (ddd, J=12.9, 8.7, 3.5 Hz, 1H), 1.17 (d, J=2.6 Hz, 3H), 1.16 (d, J=2.0 Hz, 3H), 0.72 (d, J=6.4 Hz, 3H), 0.68 (d, J=6.5 Hz, 3H). ¹³C NMR (150 MHz, CD₃OD) δ 177.55, 174.02, 172.17, 168.31, 155.36, 150.42, 147.12, 143.33, 138.63, 132.21, 131.49, 130.23, 129.28, 125.66, 123.27, 122.49, 113.49, 78.35, 72.78, 57.36, 56.60, 43.67, 41.17, 40.91, 38.96, 37.88, 36.35, 25.60, 23.15, 21.66, 17.35, 15.06. HRMS (ES) calculated for C₃₄H₄₂ClN₃O₇ [M+H] 640.2784, found 640.2787.

(3S,10R,16S,E)-10-(3-chloro-4-methoxybenzyl)-3-isobutyl-6,6-dimethyl-16-((R,E)-4-(pyridin-4-yl)but-3-en-2-yl)-1,4-dioxa-8,11-diazacyclohexadec-13-ene-2,5,9,12-tetraone (25f).

Reaction was run and purified as per general procedure for semi-preparative scale reaction. ¹H NMR (600MHz, CD₃OD) δ 8.45 (d, J=5.7 Hz, 2H), 7.44 (d, J=6.3 Hz, 2H), 7.28 (d, J=2.2 Hz, 1H), 7.17 (dd, J=8.4, 2.2 Hz, 1H), 6.98 (d, J=8.5 Hz, 1H), 6.72 (ddd, J=15.1, 11.2, 3.9 Hz, 1H), 6.51 (s, 1H), 6.50 (d, J=4.6 Hz, 1H), 5.92 (dd, J=15.1, 1.9 Hz, 1H), 5.09 (ddd, J=11.3, 7.2, 1.9 Hz, 1H), 4.95 (dd, J=9.9, 3.3 Hz, 1H), 4.51 (dd, J=11.3, 3.7 Hz, 1H), 3.84 (s, 3H), 3.46 (d, J=13.6 Hz, 1H), 3.18 (dd, J=14.6, 3.8 Hz, 1H), 3.08 (d, J=13.6 Hz, 1H), 2.74 (dd, J=14.5, 11.3 Hz, 1H), 2.74-2.66 (m, 2H), 2.35 (dt, J=14.5, 11.2 Hz, 1H), 1.67-1.54 (m, 2H), 1.37-1.24 (m, 1H), 1.19 (s, 3H), 1.18 (d, J=6.9 Hz, 3H), 1.16 (s, 3H), 0.74 (d, J=6.3 Hz, 3H), 0.71 (d, J=6.4 Hz, 3H). ¹³C NMR (150 MHz, CD₃OD) δ177.59, 174.05, 172.32, 168.36, 155.34, 143.63, 137.86, 132.21, 131.48, 130.26, 129.63, 129.28, 125.50, 123.24, 122.46, 121.98, 113.46, 78.68, 72.91, 57.37, 56.58, 43.68, 41.18, 40.87, 38.95, 38.75, 37.84, 36.36, 25.64, 23.18, 21.67, 17.75, 15.07. HRMS (ES) calculated for C₃₅H₄₄ClN₃O₇ [M+H] 654.2941, found 654.2947.

(3S,6R,10R,16S,E)-10-(3-chloro-4-methoxybenzyl)-3-isobutyl-6-methyl-16-((R,E)-4-(pyrazin-2-yl)but-3-en-2-yl)-1,4-dioxa-8,11-diazacyclohexadec-13-ene-2,5,9,12-tetraone (25q).

Reaction was run and purified as per general procedure for semi-preparative scale reaction. ¹H NMR (600MHz, CD₃OD) δ 8.61 (d, J=1.5 Hz, 1H), 8.54 (dd, J=2.6, 1.5 Hz, 1H), 8.42 (d, J=2.6 Hz 1H), 7.28 (d, J=2.2 Hz, 1H), 7.17 (dd, J=8.4, 2.2 Hz, 1H), 6.98 (d, J=8.5 Hz, 1H), 6.84 (dd, J=15.7, 8.9 Hz, 1H), 6.71 (ddd, J=15.2, 11.2, 3.9 Hz, 1H), 6.64 (d, J=15.7 Hz, 1H), 5.93 (dd, J=15.1, 1.9 Hz, 1H), 5.11 (ddd, J=11.3, 6.8, 2.0 Hz, 1H), 4.94 (dd, J=9.7, 3.7 Hz, 1H), 4.53 (dd, J=11.2, 3.9 Hz, 1H), 3.84 (s, 3H), 3.58 (dd, J=13.8, 3.4 Hz, 1H), 3.27 (dd, J=13.7, 3.0 Hz, 1H), 3.18 (dd, J=14.5, 3.9 Hz, 1H), 2.81-2.72 (m, 3H), 2.69 (ddt, J=14.2, 3.7, 1.9 Hz, 1H), 2.38 (dt, J=14.6, 11.2 Hz, 1H), 1.70-1.57 (m, 2H), 1.36 (ddd, J=14.1, 8.7, 3.7 Hz, 1H), 1.19 (d, J=6.9 Hz, 3H), 1.19 (d, J=7.5 Hz, 3H), 0.76 (d, J=6.5 Hz, 3H), 0.73 (d, J=6.5 Hz, 3H). ¹³C NMR (150 MHz, CD₃OD) δ 177.53, 174.03, 172.15, 168.32, 155.36, 152.52, 145.69, 144.15, 143.92, 143.33, 140.15, 132.22, 131.48, 129.28, 128.83, 125.65, 123.27, 113.50, 78.45, 72.83, 57.35, 56.60, 43.37, 41.19, 40.91, 38.98, 38.03, 36.35, 25.65, 23.23, 21.74, 17.37, 15.07. HRMS (ES) calculated for [M+H] 641.2737, found 641.2742.

(3S,6R,10R,16S,E)-10-(3-chloro-4-methoxybenzyl)-3-isobutyl-6-methyl-16-((R,E)-4-(1-methyl-1H-pyrazol-5-yl)but-3-en-2-yl)-1,4-dioxa-8, 11-diazacyclohexadec-13-ene-2,5,9, 12-tetraone (25h).

Reaction was run and purified as per general procedure for semi-preparative scale reaction. ¹H NMR (600 MHz, CD₃OD) δ 7.36 (d, J=2.1 Hz, 1H), 7.28 (d, J=2.2 Hz, 1H), 7.17 (dd, J=8.5, 2.2 Hz, 1H), 6.98 (d, J=8.4 Hz, 1H), 6.71 (ddd, J=15.1, 11.2, 3.9 Hz, 1H), 6.52 (d, J=15.8 Hz, 1H), 6.42 (d, J=2.1 Hz, 1H), 6.14 (dd, J=15.8, 9.0 Hz, 1H), 5.93 (dd, J=15.1, 1.9 Hz, 1H), 5.07 (ddd, J=11.3, 6.9, 1.9 Hz, 1H), 4.93 (dd, J=9.8, 3.6 Hz, 1H), 4.52 (dd, J=11.3, 3.9 Hz, 1H), 3.84 (s, 6H), 3.59 (dd, J=13.8, 3.3 Hz, 1H), 3.27 (dd, J=13.8, 3.0 Hz, 1H), 3.18 (dd, J=14.5, 3.9 Hz, 1H), 2.79-2.73 (m, 2H), 2.73-2.62 (m, 2H), 2.35 (dt, J=14.6, 11.2 Hz, 1H), 1.71-1.57 (m, 2H), 1.35 (ddd, J=14.0, 8.6, 3.5 Hz, 1H), 1.19 (d, J=7.4 Hz, 3H), 1.17 (d, J=6.9 Hz, 3H), 0.77 (d, J=6.4 Hz, 6H). ¹³C NMR: (150 MHz, CD₃OD) δ 177.58, 174.04, 172.22, 168.32, 155.35, 143.40, 142.29, 139.27, 136.81, 132.20, 131.48, 129.28, 125.61, 123.24, 119.18, 113.46, 103.68, 78.39, 72.84, 57.39, 56.58, 43.68, 41.16, 40.96, 38.96, 37.96, 36.51, 36.36, 25.69, 23.25, 21.76, 17.53, 15.08. HRMS (ES) calculated for C₃₃H₄₃ClN₄O₇ [M+H] 643.2893, found 643.2890.

(3S,6R,10R,16S,E)-10-(3-chloro-4-methoxybenzyl)-3-isobutyl-6-methyl-16-((R,E)-4-(1-methyl-1H-pyrazol-3-yl)but-3-en-2-yl)-1,4-dioxa-8,11-diazacyclohexadec-13-ene-2,5,9,12-tetraone (25i).

Reaction was run and purified as per general procedure for semi-preparative scale reaction. ¹H NMR (600 MHz, CD₃OD) δ 7.47 (d, J=2.3 Hz, 1H), 7.26 (d, J=2.2 Hz, 1H), 7.15 (dd, J=8.4, 2.2 Hz, 1H), 6.96 (d, J=8.5 Hz, 1H), 6.68 (ddd, J=15.1, 11.1, 3.9 Hz, 1H), 6.36 (d, J=16.0 Hz, 1H), 6.33 (d, J=2.3 Hz, 1H), 6.05 (dd, J=16.0, 9.0 Hz, 1H), 5.90 (dd, J=15.2, 1.9 Hz, 1H), 5.00 (ddd, J=11.3, 7.1, 2.0 Hz, 1H), 4.90 (dd, J=10.0, 3.6 Hz, 1H), 4.50 (dd, J=11.2, 3.9 Hz, 1H), 3.56 (dd, J=13.8, 3.3 Hz, 1H), 3.25 (dd, J=13.8, 3.0 Hz, 1H), 3.16 (dd, J=14.5, 3.9 Hz, 1H), 2.77-2.71 (m, 2H), 2.65 (ddt, J=14.5, 4.1, 2.1 Hz, 1H), 2.61-2.51 (m, 1H), 2.34 (dt, J=14.6, 11.2 Hz, 1H), 1.68-1.61 (m, 1H), 1.57 (ddd, J=14.8, 10.0, 5.0 Hz, 1H), 1.35 (ddd, J=14.2, 9.0, 3.6 Hz, 1H), 1.17 (d, J=7.4 Hz, 3H), 1.12 (d, J=6.8 Hz, 3H), 0.76 (d, J=6.5 Hz, 3H), 0.74 (d, J=6.6 Hz, 3H). ¹³C NMR (150 MHz, CD₃OD) δ 177.56, 174.05, 172.28, 168.35, 155.35, 151.52, 143.52, 133.58, 133.15, 132.23, 131.49, 129.28, 125.57, 124.52, 123.26, 113.49, 103.64, 78.52, 72.93, 57.36, 56.60, 43.57, 41.19, 40.83, 38.97, 38.65, 37.89, 36.36, 25.68, 23.16, 21.62, 17.61, 15.06. HRMS (ES) calculated for C₃₅H₄₇ClN₄O₇ [M+H] 671.3206, found 671.3025.

(3S,6R,10R,16S,E)-10-(3-chloro-4-methoxybenzyl)-3-isobutyl-6-methyl-16-((R,E)-4-(1-methyl-1H-pyrazol-4-yl)but-3-en-2-yl)-1,4-dioxa-8,11-diazacyclohexadec-13-ene-2,5,9,12-tetraone (25j).

Reaction was run and purified as per general procedure for semi-preparative scale reaction. ¹H NMR (600 MHz, CD₃OD) δ7.61 (s, 1H), 7.51 (s, 1H), 7.28 (d, J=2.2 Hz, 1H), 7.17 (dd, J=8.4, 2.2 Hz, 1H), 6.98 (d, J=8.4 Hz, 1H), 6.70 (ddd, J=15.2, 11.2, 3.9 Hz, 1H), 6.27 (d, J=15.9 Hz, 1H), 5.92 (dd, J=15.2, 1.9 Hz, 1H), 5.80 (dd, J=15.9, 8.9 Hz, 1H), 4.99 (ddd, J=11.3, 7.1, 1.9 Hz, 1H), 4.92 (dd, J=10.0, 3.6 Hz, 1H), 4.52 (dd, J=11.3, 3.8 Hz, 1H), 3.84 (d, J=1.8 Hz, 6H), 3.58 (dd, J=13.8, 3.3 Hz, 1H), 3.27 (dd, J=13.8, 2.9 Hz, 1H), 3.18 (dd, J=14.5, 3.8 Hz, 1H), 2.81-2.70 (m, 2H), 2.69-2.60 (m, 1H), 2.50 (p, J=7.1 Hz, 1H), 2.33 (dt, J=14.5, 11.2 Hz, 1H), 1.71-1.56 (m, 2H), 1.38 (ddd, J=13.2, 9.0, 3.6 Hz, 1H), 1.18 (d, J=7.5 Hz, 3H), 1.11 (d, J=6.8 Hz, 3H), 0.78 (d, J=6.5 Hz, 3H), 0.76 (d, J=6.6 Hz, 3H). $^{13}$C NMR (150 MHz, CD$_3$OD) δ 177.59, 174.05, 172.32, 168.36, 155.34, 143.63, 137.86, 132.21, 131.48, 130.26, 129.63, 129.28, 125.50, 123.24, 122.46, 121.98, 113.46, 78.68, 72.91, 57.37, 56.58, 43.68, 41.18, 40.87, 38.95, 38.75, 37.84, 36.36, 25.64, 23.18, 21.67, 17.75, 15.07. HRMS (ES) calculated for C$_{33}$H$_{43}$ClN$_4$O$_7$ [M+H] 643.2893, found 643.2890.

(3S,10R,16S,E)-10-(3-chloro-4-methoxybenzyl)-3-isobutyl-6,6-dimethyl-16-((R,E)-4-(1-methyl-1H-pyrazol-4-yl)but-3-en-2-yl)-1,4-dioxa-8,11-diazacyclohexadec-13-ene-2,5,9,12-tetraone.

Reaction was run and purified as per general procedure for semi-preparative scale reaction. $^1$H NMR (600MHz, CD$_3$OD) 7.60 (s, 1H), 7.51 (s, 1H), 7.27 (d, J=2.1 Hz, 1H), 7.16 (dd, J=8.5, 2.2 Hz, 1H), 6.97 (d, J=8.5 Hz, 1H), 6.70 (ddd, J=15.2, 11.2, 3.9 Hz, 1H), 6.27 (d, J=15.9 Hz, 1H), 5.90 (dd, J=15.1, 1.9 Hz, 1H), 5.79 (dd, J=15.9, 8.9 Hz, 1H), 4.97 (ddd, J=11.3, 7.1, 1.6 Hz, 1H), 4.94 (dd, J=9.9, 3.4 Hz, 1H), 4.50 (dd, J=11.4, 3.7 Hz, 1H), 3.83 (s, 3H), 3.83 (s, 3H), 3.45 (d, J=13.6 Hz, 1H), 3.17 (dd, J=14.5, 3.7 Hz, 1H), 3.07 (d, J=13.6 Hz, 1H), 2.73 (dd, J=14.5, 11.4 Hz, 1H), 2.65 (dt, J=14.7, 2.4 Hz, 1H), 2.50 (h, J=7.2 Hz, 1H), 2.32 (dt, J=14.4, 11.2 Hz, 1H), 1.68-1.57 (m, 2H), 1.43-1.36 (m, 1H), 1.19 (s, 3H), 1.15 (s, 3H), 1.11 (d, J=6.9 Hz, 3H), 0.77 (t, J=6.7 Hz, 6H). $^{13}$C NMR (150 MHz, CD$_3$OD) δ 178.97, 173.70, 172.12, 168.25, 155.37, 143.83, 137.86, 132.17, 131.46, 130.26, 129.63, 129.26, 125.33, 123.27, 122.48, 121.98, 113.49, 78.65, 72.69, 57.47, 56.59, 47.40, 44.01, 43.68, 40.85, 38.75, 37.88, 36.49, 25.90, 23.32, 23.28, 23.20, 21.64, 17.74. HRMS (ES) calculated for C$_{34}$H$_{45}$ClN$_4$O$_7$ [M+H] 656.2977, found 656.2973.

(3S,6R,10R,16S,E)-10-(3-chloro-4-methoxybenzyl)-3-isobutyl-16-((R,E)-4-(1-isopropyl-1 H-pyrazol-4-yl)but-3-en-2-yl)-6-methyl-1,4-dioxa-8,11-diazacyclohexadec-13-ene-2,5,9,12-tetraone (25l).

Reaction was run and purified as per general procedure for semi-preparative scale reaction. $^1$H NMR (600 MHz, CD$_3$OD) δ 7.70 (s, 1H), 7.53 (s, 1H), 7.28 (d, J=2.2 Hz, 1H), 7.17 (dd, J=8.4, 2.2 Hz, 1H), 6.98 (d, J=8.5 Hz, 1H), 6.70 (ddd, J=15.1, 11.2, 3.9 Hz, 1H), 6.28 (d, J=15.8 Hz, 1H), 5.92 (dd, J=15.2, 1.9 Hz, 1H), 5.79 (dd, J=15.9, 8.9 Hz, 1H), 4.98 (ddd, J=11.2, 7.5, 2.0 Hz, 1H), 4.91 (dd, J=10.0, 3.5 Hz, 1H), 4.52 (dd, J=11.2, 3.8 Hz, 1H), 4.47 (p, J=6.7 Hz, 1H), 3.84 (s, 3H), 3.58 (dd, J=13.8, 3.3 Hz, 1H), 3.27 (dd, J=13.7, 3.0 Hz, 1H), 3.18 (dd, J=14.5, 3.8 Hz, 1H), 2.79-2.71 (m, 2H), 2.71-2.63 (m, 1H), 2.50 (h, J=7.2 Hz, 1H), 2.33 (dt, J=14.5, 11.2 Hz, 1H), 1.72-1.54 (m, 2H), 1.46 (d, J=6.7 Hz, 6H), 1.37 (ddd, J=14.2, 9.0, 3.6 Hz, 1H), 1.18 (d, J=7.4 Hz, 3H), 1.12 (d, J=6.9 Hz, 3H), 0.77 (d, J=6.5 Hz, 3H), 0.74 (d, J=6.6 Hz, 3H). $^{13}$C NMR (150 MHz, CD$_3$OD) δ177.60, 174.05, 172.33, 168.37, 155.35, 143.64, 137.40, 132.21, 131.48, 130.12, 129.28, 126.34, 125.51, 123.25, 122.67, 121.38, 113.46, 78.67, 72.93, 57.38, 56.59, 55.07, 43.80, 41.18, 40.87, 38.96, 37.85, 36.37, 25.64, 23.31, 23.09, 21.70, 17.79, 15.07. HRMS (ES) calculated for C$_{35}$H$_{47}$ClN$_4$O$_7$ [M+H] 671.3206, found 671.3025.

(3S,6R,10R,16S,E)-10-(3-chloro-4-methoxybenzyl)-16-((R,E)-4-(3,5-dimethylisoxazol-4-yl)but-3-en-2-yl)-3-isobutyl-6-methyl-1,4-dioxa-8,11-diazacyclohexadec-13-ene-2,5,9,12-tetraone (25m).

Reaction was run and purified as per general procedure for semi-preparative scale reaction. $^1$H NMR (600 MHz, CD$_3$OD) δ 7.28 (d, J=2.2 Hz, 1H), 7.17 (dd, J=8.4, 2.2 Hz, 1H), 6.98 (d, J=8.4 Hz, 1H), 6.69 (ddd, J=15.1, 11.1, 3.9 Hz, 1H), 6.23 (d, J=16.2 Hz, 1H), 5.93 (dd, J=15.1, 1.9 Hz, 1H), 5.80 (dd, J=16.2, 8.9 Hz, 1H), 5.06 (ddd, J=11.3, 6.7, 1.9 Hz, 1H), 4.93 (dd, J=9.7, 3.8 Hz, 1H), 4.51 (dd, J=11.2, 3.9 Hz, 1H), 3.84 (s, 3H), 3.57 (dd, J=13.7, 3.3 Hz, 1H), 3.27 (dd, J=13.8, 3.0 Hz, 1H), 3.17 (dd, J=14.5, 3.9 Hz, 1H), 2.80-2.71 (m, 2H), 2.67 (ddt, J=14.6, 4.0, 2.0 Hz, 1H), 2.58 (dt, J=8.8, 6.6 Hz, 1H), 2.40 (s, 3H), 2.35 (dt, J=14.5, 11.4 Hz, 1H), 2.28 (s, 3H), 1.70-1.53 (m, 2H), 1.33 (ddd, J=14.1, 8.7, 3.8 Hz, 1H), 1.18 (d, J=7.4 Hz, 3H), 1.15 (d, J=6.9 Hz, 3H), 0.79 (d, J=3.7 Hz, 3H), 0.78 (d, J=3.8 Hz, 3H). $^{13}$C NMR (150 MHz, CD$_3$OD) δ 177.53, 174.04, 172.23, 168.34, 166.95, 159.53, 155.35, 143.40, 134.36, 132.19, 131.48, 129.29, 125.65, 123.24, 120.19, 113.78, 113.46, 78.53, 72.77, 57.40, 56.58, 44.22, 41.16, 41.02, 38.95, 37.87, 36.35, 25.62, 23.20, 21.77, 17.83, 15.07, 11.55, 11.45. HRMS (ES) calculated for C$_{34}$H$_{44}$ClN$_3$O$_8$ [M+H] 658.2890, found 658.2893.

General Protein Expression and Purification Procedure

Proteins were grown and purified using a modified protocol.[12] The pET-28 b (+)-CrpTE construct was transformed into BL21 (DE3) and grown on LB agar plates supplemented with 50 μg/mL kanamycin at 37° C. overnight. Colonies were picked and grown in 25 mL LB broth overnight at 37° C. supplemented with 50 μg/mL kanamycin. Six liters of TB expression media containing 50 μg/mL of kanamycin were each inoculated with 4 mL of overnight culture and incubated (37° C., 200 rpm) for about 5 hours until the OD$_{600}$ reached 1.2. The flasks were removed from the shaker and cooled in an ice bath for 15 minutes (temperature about 20° C.). The flasks were returned to shaking, and protein expression was initiated with the addition of 100 μM IPTG and proceeded at 20° C. for 18 hours. Cells were harvested via centrifugation at 6,000×g for 30 minutes.

The cell pellet was then re-suspended in lysis buffer (10 mL/g cell pellet, 100 mM sodium phosphate, 20 mM imidazole, 300 mM NaCl, pH 8) and treated with 1 mg Dnase (Sigma). The solution was placed on ice and subjected to sonication (12×10 seconds with 50-second pauses). The suspension was then centrifuged at 50,000×g for 30 minutes at 4° C. The supernatant was collected and passed through a 0.45 μm filter prior to being loaded onto a 10 mL NiNTA resin column. The column was washed with 10 column volumes of wash buffer (100 mM sodium phosphate buffer, 50 mM imidazole, 300 mM NaCl, pH 8) and the proteins were eluted using 15 mL elution buffer (100 mM sodium phosphate, 300 mM imidazole, 300 mM NaCl, pH 8). Eluates were then concentrated to 2.5 mL, subjected to PD-10 buffer exchange/desalting columns (pre equilibrated with storage buffer, 100 mM sodium phosphate, 150 mM NaCl, pH 7.2), flash-frozen with liquid nitrogen, and placed at −80° C. for storage. Samples were run on a NuPAGE 4-12% Bis-Tris protein gel to check for purity.

REFERENCES FOR EXAMPLE 2

1. Shankaraiah, G.; Kumar, T. V.; Reddy, G. V.; Rao, J. M.; Babu, K. S. Stereoselective Synthesis of (−)-Pinidinone. *Helvetica Chimica Acta* 2013, 96, 990-996.

2. Gao, X.; Han, H.; Krische, M. J. Direct Generation of Acyclic Polypropionate Stereopolyads via Double Diastereo- and Enantioselective Iridium-Catalyzed Crotylation of 1,3-Diols: Beyond Stepwise Carbonyl Addition in Polyketide Construction. *Journal of the American Chemical Society* 2011, 133, 12795-12800.
3. Phukan, P.; Bauer, M.; Maier, M. E. Facile generation of alkenes and dienes from tosylates. *Synthesis-Stuttgart* 2003, 1324-1328.
4. Kotoku, N.; Kato, T.; Narumi, F.; Ohtani, E.; Kamada, S.; Aoki, S.; Okada, N.; Nakagawa, S.; Kobayashi, M. Synthesis of 15,20-triamide analogue with polar substituent on the phenyl ring of arenastatin A, an extremely potent cytotoxic spongean depsipeptide. *Bioorganic & Medicinal Chemistry* 2006, 14, 7446-7457.
5. Krishnamurthy, S. Rapid Reduction of Alkyl Tosylates with Lithium Triethylborohydride—Convenient and Advantageous Procedure for Deoxygenation of Simple and Hindered Alcohols—Comparison of Various Hydride Reagents. *Journal of Organometallic Chemistry* 1978, 156, 171-181.
6. Morrill, C.; Grubbs, R. H. Synthesis of functionalized vinyl boronates via ruthenium-catalyzed olefin cross-metathesis and subsequent conversion to vinyl halides. *Journal of Organic Chemistry* 2003, 68, 6031-6034.
7. McCubbin, J. A.; Maddess, M. L.; Lautens, M. Total synthesis of cryptophycin analogues via a scaffold approach. *Org. Lett.* 2006, 8, 2993-6.
8. Ghosh, A. K.; Bischoff, A. Asymmetric syntheses of potent antitumor macrolides cryptophycin B and arenastatin A. *European Journal of Organic Chemistry* 2004, 2131-2141.
9. Ghosh, A. K.; Swanson, L. Enantioselective synthesis of (+)-cryptophycin 52 (LY355703), a potent antimitotic antitumor agent. *J. Org. Chem.* 2003, 68, 9823-6.
10. Buck, S. B.; Huff, J. K.; Himes, R. H.; Georg, G. I. Total synthesis and anti-tubulin activity of epi-c3 analogues of cryptophycin-24. *J. Med. Chem.* 2004, 47, 3697-9.
11. Mast, C. A.; Eissler, S.; Stoncius, A.; Stammler, H. G.; Neumann, B.; Sewald, N. Efficient and versatile stereoselective synthesis of cryptophycins. *Chemistry* 2005, 11, 4667-77.
12. Beck, Z. Q.; Aldrich, C. C.; Magarvey, N. A.; Georg, G. I.; Sherman, D. H. Chemoenzymatic synthesis of cryptophycin/arenastatin natural products. *Biochemistry* 2005, 44, 13457-13466.

Example 3

Synthesis of Seco Cryptophycin Chain Elongation Intermediates.

In order to test the substrate scope of the CrpTE as well as produce novel cryptophycin macrolactones, a scalable synthesis of the NAc-activated seco chain elongation intermediate was developed that was amenable to late stage diversification of the unit A aryl group. Analogs were synthesized convergently using two key intermediates, including unit AB and unit CD-NAc. Formulation of units AB took advantage of chiral auxiliary chemistry as well as a Suzuki coupling strategy reported previously.[38] A final Horner Wadsworth Emmons olefination (HWE) was employed to form the key junction between units A and B. Unit CD, with the NAc recognition element, was generated via peptide coupling of commercially and readily manipulated amino acid derivatives.

Towards that end, unit A was synthesized (FIG. 3) using an Evans asymmetric aldol with N-crotonyl oxazolidinone 1 and aldehyde 2, which produced excellent yields with a high dr (>20:1) to afford the desired (2R, 3S) adduct. Subsequent silation with TBS trifluoromethanesulfonate to produce 3, and reductive cleavage of the chiral auxiliary produced alcohol 4.[39] Tosylation to produce 5 and consecutive reductive deoxygenation with lithium triethyl borohydride furnished the desired intermediate 6.[40] At this stage, a vinyl pinacol boronic ester was introduced via Hoveyda-Grubbs cross metathesis to give 7 with the desired Suzuki handle for future diversification.[38] Removal of the p-methoxy benzyl (PMB) protecting group of with 2,3-Dichloro-5,6-dicyano-1,4-benzoquinone (DDQ) and subsequent Dess Martin Periodinane (DMP) oxidation to 8 furnished the unit A aldehyde fragment necessary for the HWE olefination.[41]

Figure 5:
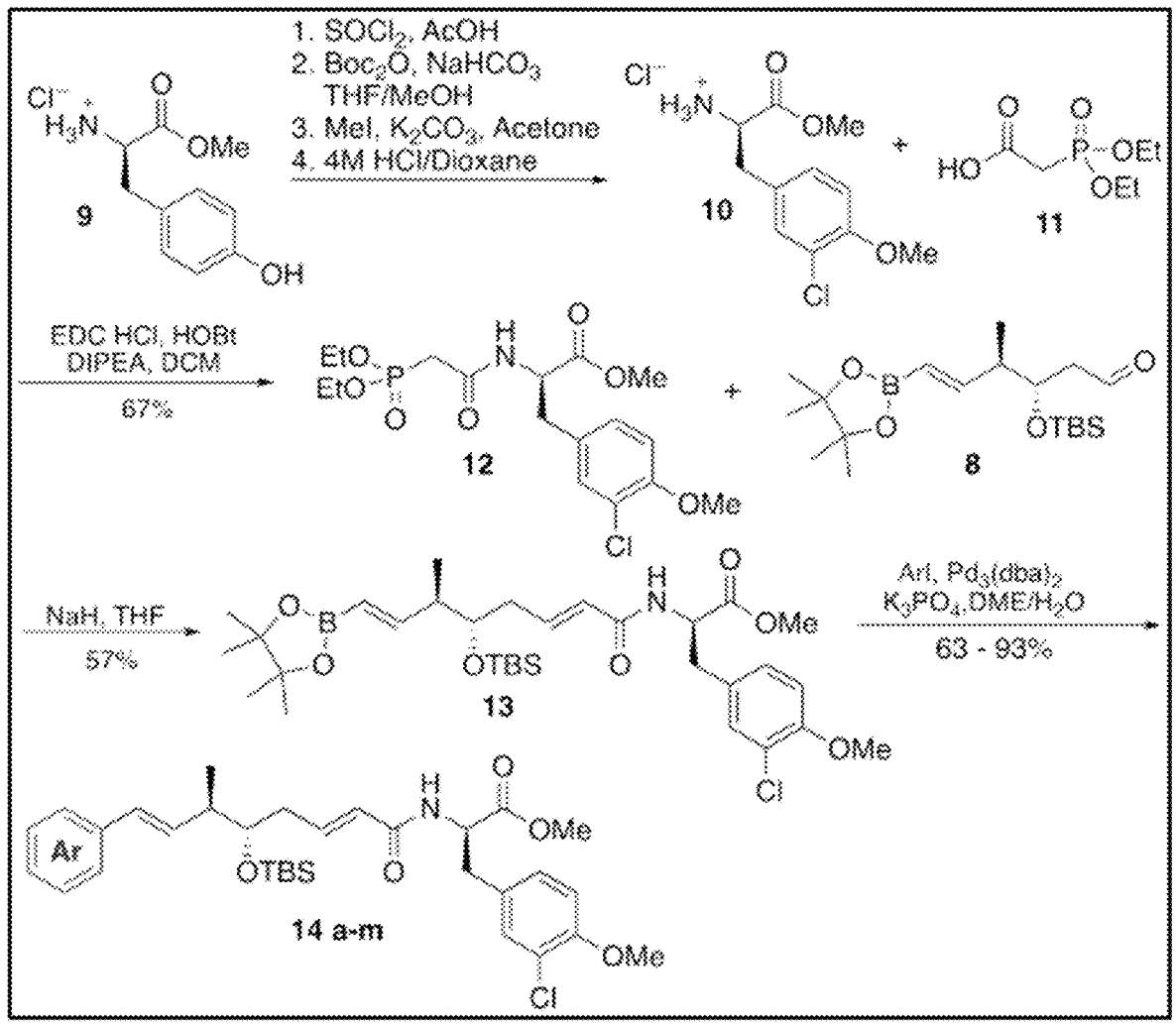
FIG. 5. A schematic illustration of the synthesis of a unit AB fragment.

The phosphonate partner 12 (FIG. 5) was synthesized beginning with commercially available D-Tyrosine methyl ester hydrochloride 9, which was converted to 10 as previously described in four steps.[42] Subsequent peptide coupling with diethylphosphonoacetic acid (11) furnished the desired phosphonate 12. From here, HWE olefination conditions were explored, resulting in optimal conditions using sodium hydride in THF, which furnished the diversifiable unit AB fragment 10 in a 57% yield of the correct isomer (70% overall yield, with about 5:1 E:Z product ratio).

Figure 6:
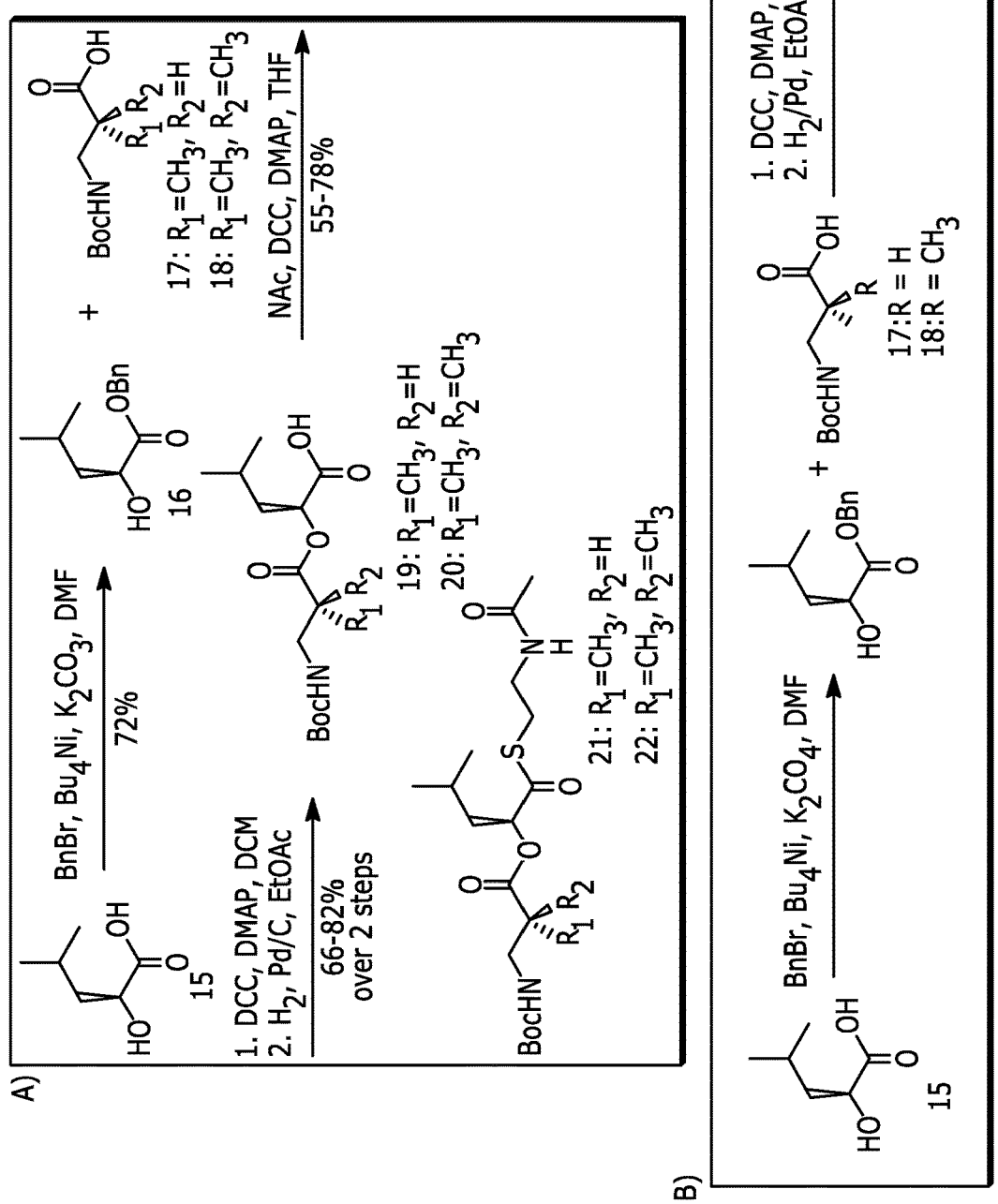
FIG. 6. A) A schematic illustration of the synthesis of a unit CD fragment. B) Unit CD synthesis reaction is schematically shown.

Unit CD-NAc was readily synthesized from commercially available leucic acid 15 (FIG. 6). Initial benzyl protection of the acid functionality produced 16, which was subsequently coupled with β-amino acids 17 or 18 to produce the desired esters. These esters were readily deprotected via $H_2$/Pd hydrogenolysis to furnish acids 19 or 20.[43] These acids were coupled with N-acetyl cysteamine, to yield the desired unit CD fragments 21 or 22.

With diversifiable substrate 13 in hand, coupling with 21 or 22 and successive Suzuki diversification were investigated. Labile functional groups and racemization precluded Suzuki diversification prior to the final peptide coupling. Screening Suzuki conditions for substrate 13, yielded a procedure that utilized $Pd_2(dba)_3$ and $K_3PO_4$ to produce a suite of novel unit AB cryptophycin analogs 14a-m (FIG. 5), in good to excellent yields with no detectable racemization.

Figure 7:
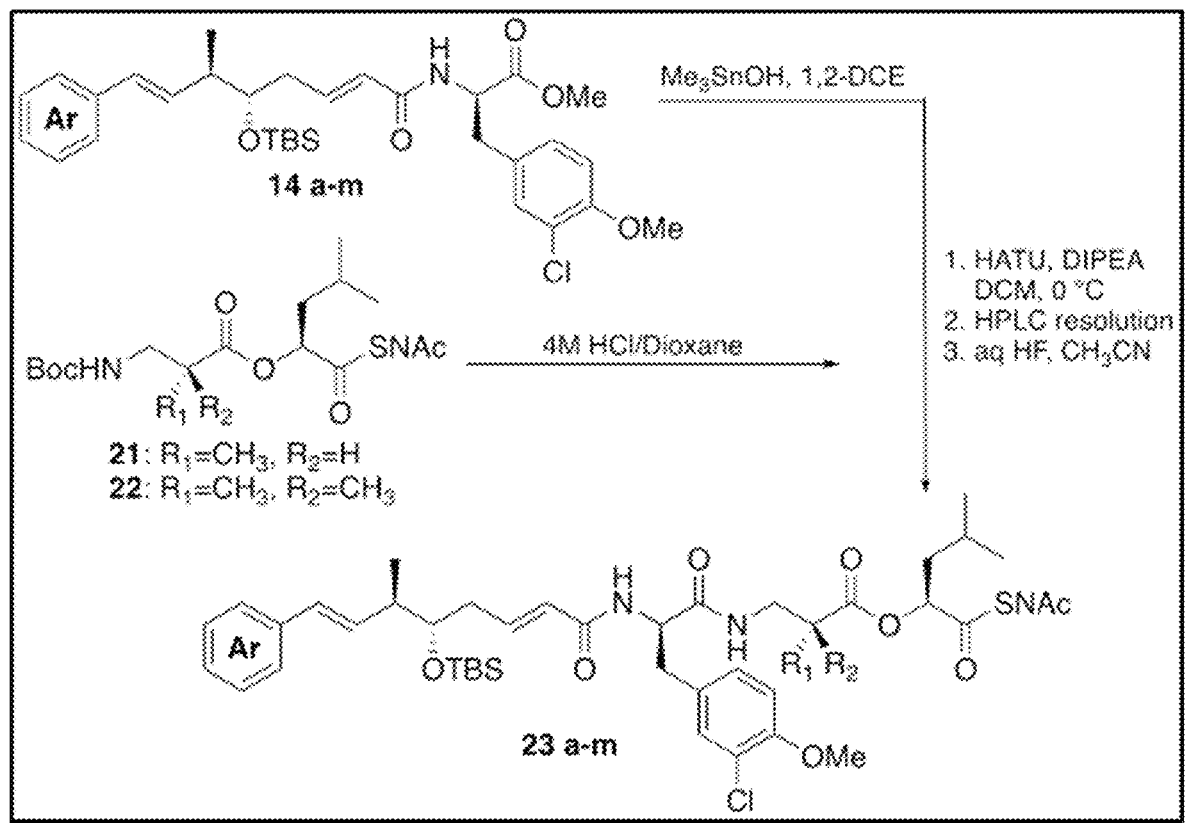
FIG. 7. A schematic illustration of the elaboration of seco cryptophycin intermediates.

Elaboration of the final seco cryptophycin chain elongation intermediates was accomplished via the coupling of units AB with units CD (FIG. 7). Saponification of the methyl esters 14a-m proved to be susceptible to racemization and a screen of different hydrolysis procedures yielded trimethyltin hydroxide, which provided the corresponding acids in good yield with no detectable racemization (FIG. 7).[44] Simultaneous Boc deprotection of 21 or 22 with 4 M HCl/Dioxane and subsequent peptide coupling at 0° C. with 1-[Bis(dimethylamino)methylene]-1H-1,2,3-triazolo[4,5-b]pyridinium 3-oxid hexafluorophosphate, Hexafluorophosphate Azabenzotriazole Tetramethyl Uronium (HATU) produced the TBS-protected intermediates in good yields with minimal racemization (7:1 to 12:1 dr, FIG. 7). Diastereomers were resolved using reverse-phase HPLC prior to removal of the TBS group. Finally, deprotection of the silyl group using aqueous HF in acetonitrile furnished the desired seco cryptophycin NAc analogs (FIG. 7, 23a-m).

Example 4

Analytical Substrate Conversion Assay of CrpTE with Unit A Heterocycles.

Figure 2:
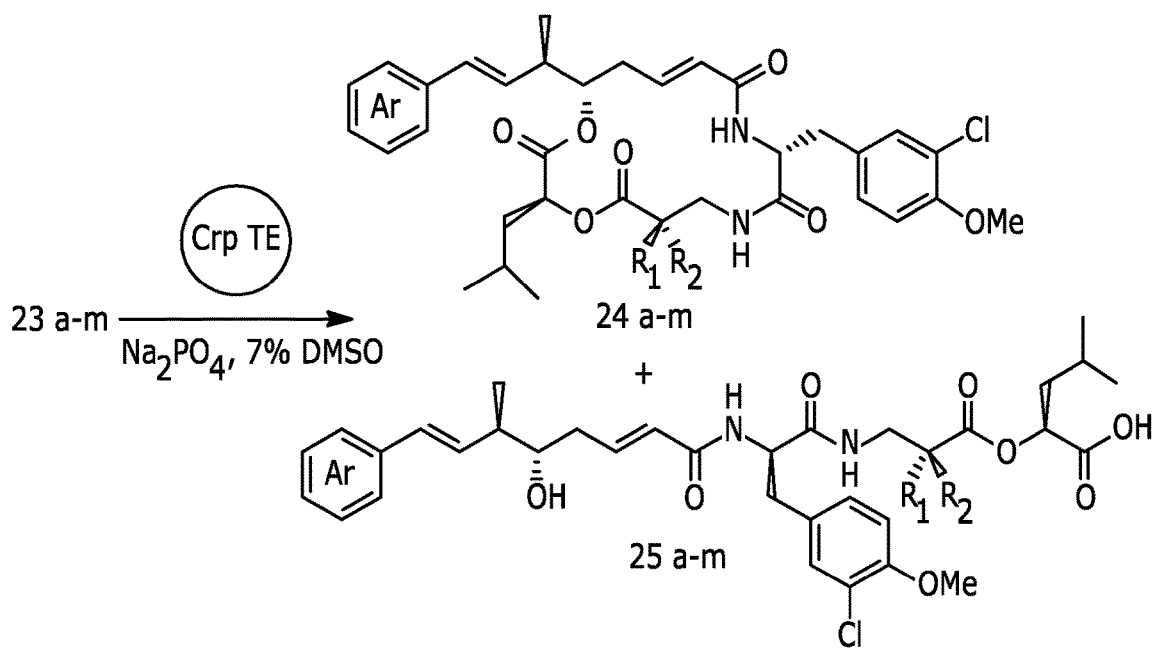
FIG. 2. TOF-LCMS analyses of analytical scale CrpTE cyclization reactions for analogs 23 a-m with starting material peaks in black, product peaks in blue, and hydrolytic byproducts in green.
Figure 2:
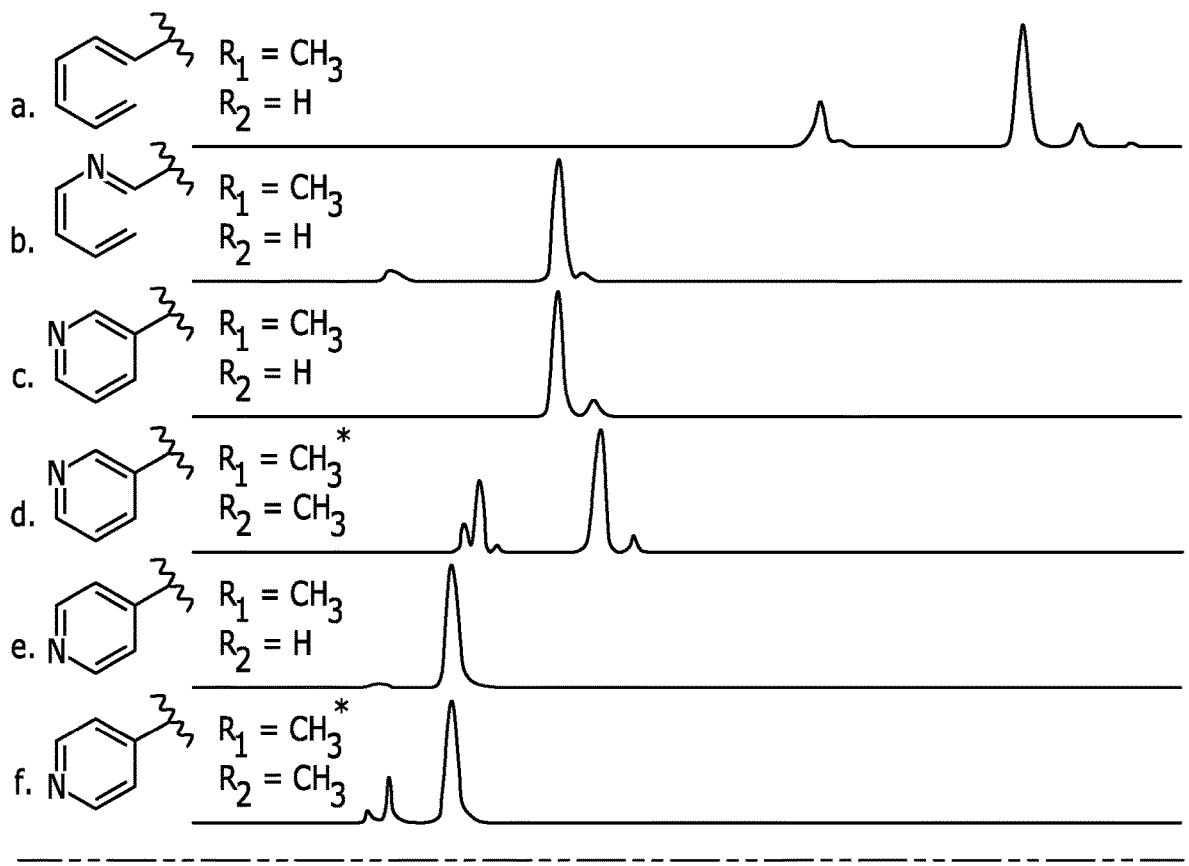
Figure 2:
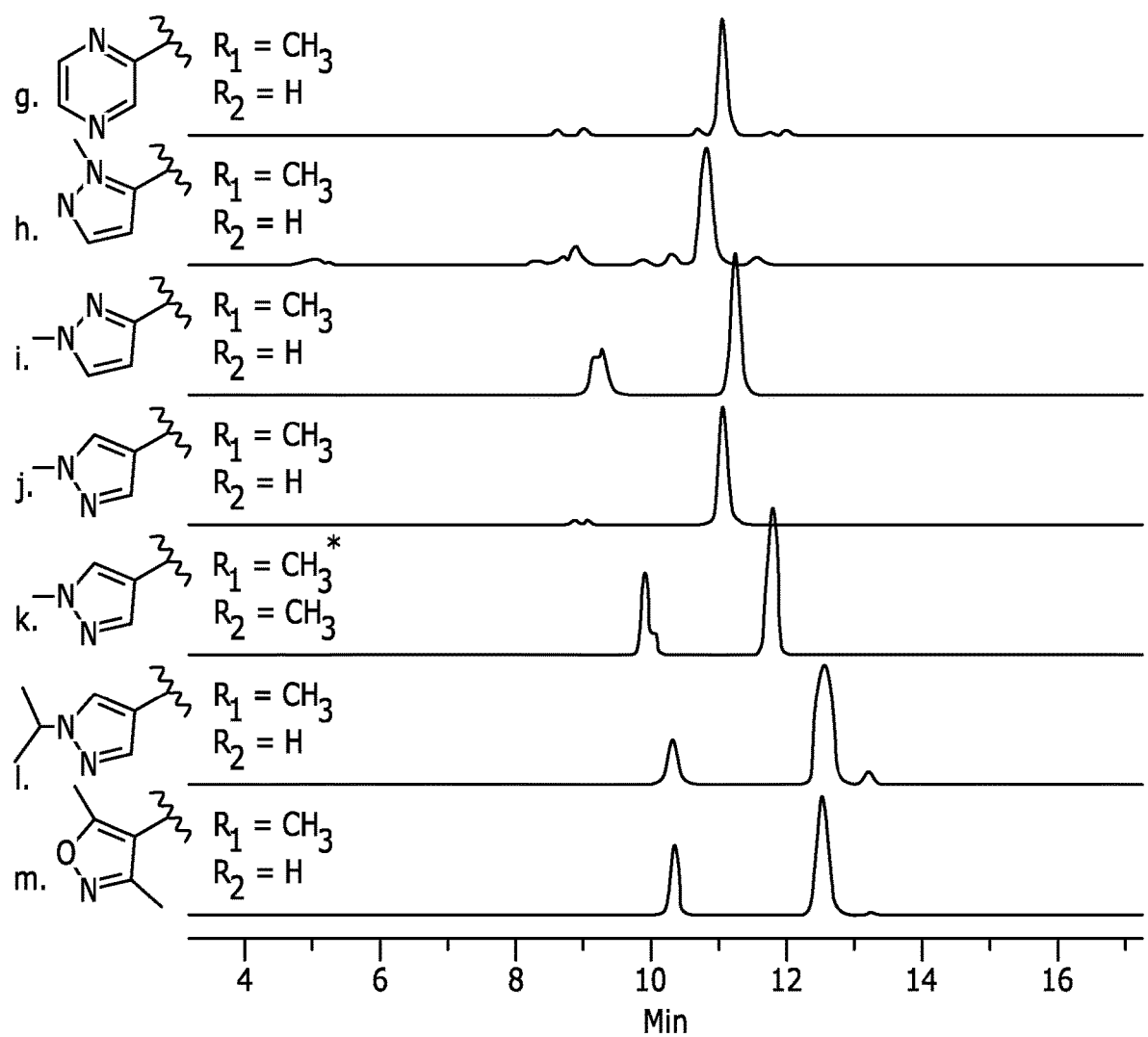

With a diversifiable synthesis in hand, we began exploring the flexibility of CrpTE against the newly generated unit A chain elongation intermediates (FIG. 2, 23a-m). The initial set of CrpTE analogs contained six-membered-ring heterocycles in place of the native benzene ring (FIG. 2, 23b-g). Initial analytical scale reactions revealed remarkable turnover to product compared to the native benzyl substrate. In our hands the native benzyl substrate (23a) showed an overall conversion of 68% with a cyclization:hydrolysis ratio of 9:1. In contrast, the 2-, 3-, 4- and pyrazine substrates showed complete turnover of starting material and nearly undetectable levels of hydrolytic bi-products (FIG. 2, 23b, 23c, 23e, 23g). This is reflected in the % conversions as well as cyclization to hydrolysis ratios seen in FIGS. 8 (24b, 24c, 24e, and 24g), all of which were significantly greater (91-96% conversion, >10:1 cyclization:hydrolysis ratio) when compared to the native substrate 24a.

Figure 8:
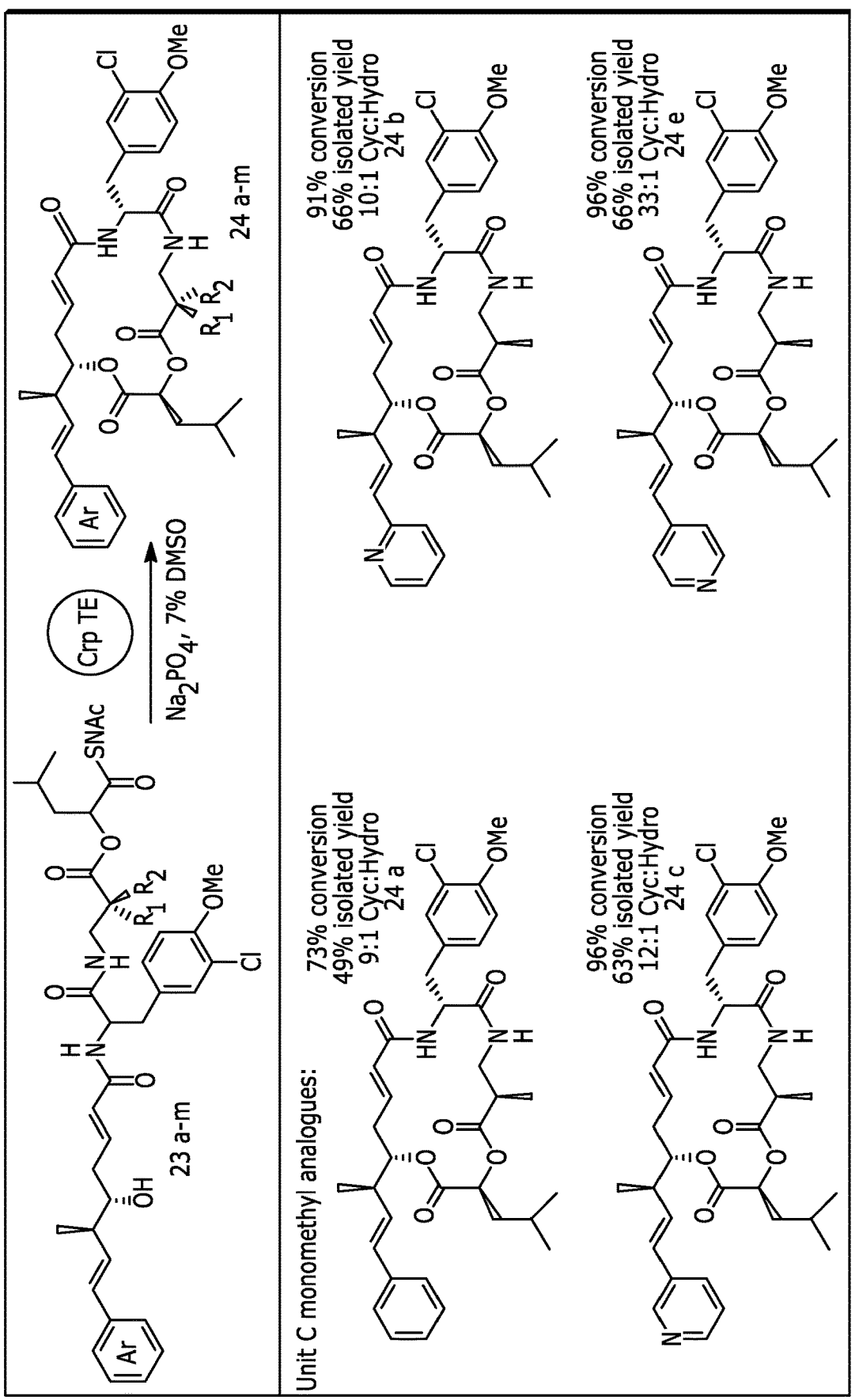
FIG. 8. Percent conversion, isolation yield, and cyclization to hydrolysis analysis of CrpTE reactions.
Figure 8:
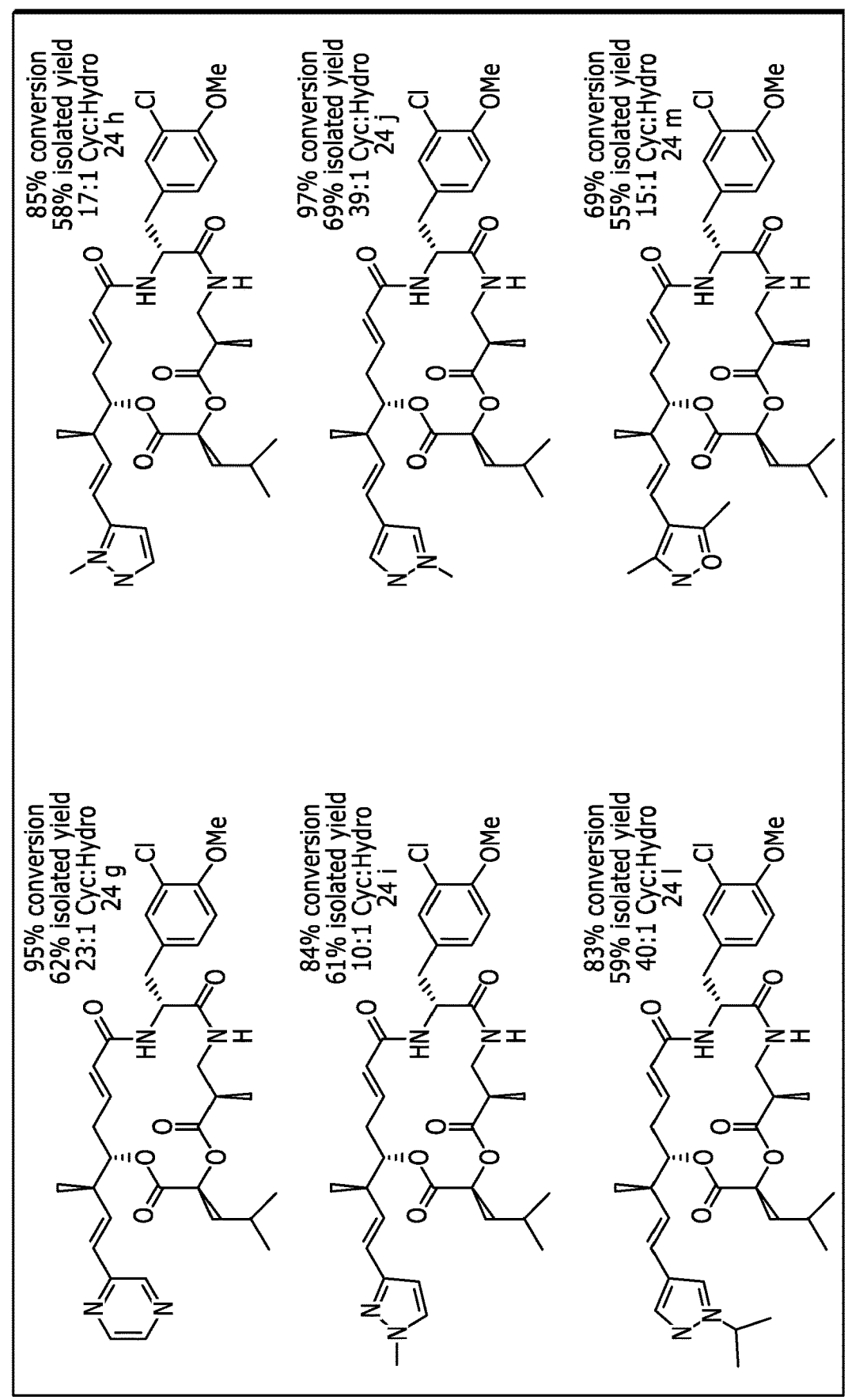
Figure 8:
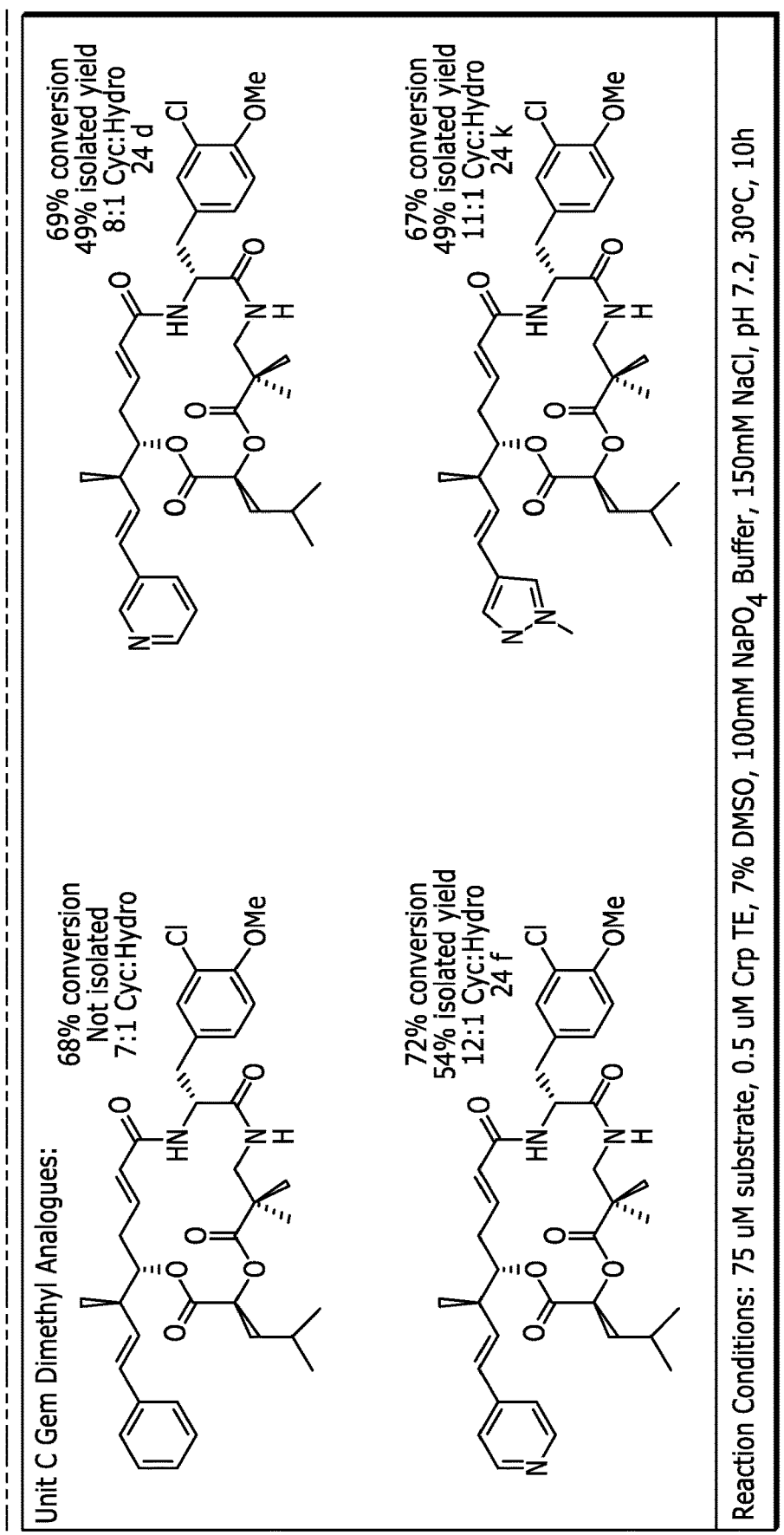

The set of unnatural unit A analogs was expanded to include five-membered-ring aromatic heterocycles with varying alkyl chains. The 2-, 3-, and 4-methyl pyrazole derivatives (23h-j) were synthesized and tested in the same analytical assay, utilizing the benzyl substrate 23a as a control. The 2-methyl pyrazole and 3-methyl pyrazole groups showed slightly lower % conversion than the previous six-membered-ring heterocycles at 85% and 84% (FIGS. 8, 24h and 24i). Despite these substrates being processed less efficiently than the six-membered-ring analogs, they retain higher % conversions to the corresponding depsipeptide cryptophycin analog than the native substrate, catalyzed by wild-type CrpTE. Interestingly, incorporation of a 4-methyl pyrazole ring (23j), showed nearly complete conversion to product with no measurable starting material or hydrolytic by-products.

Incorporating a larger alkyl chain, the 4-isopropyl pyrazole group (FIG. 2, 23i) provided important insight into potential size restrictions of the CrpTE binding pocket. Although hydrolytic products were not observed, incomplete consumption of starting material after conclusion of the reaction produced a lower % conversion (83%) in comparison to its methyl counterpart, which showed almost quantitative conversion to product. This larger alkyl substituent may indicate a steric constraint within the enzyme leading to the lower overall conversion seen with this analog. Finally, a dimethyl isoxazole substrate 23m was investigated. This compound showed similar % conversion in comparison with the native substrate (FIG. 8, 24m), with a significant amount of starting material remaining.

Example 5

Isolation and Characterization of Unit A Cryptophycin Analogues

All reactions were conducted on a semi-preparative scale of 10 mg using the same conditions as the analytical reactions in order to obtain isolated yields, full structural characterization, and biological evaluation of the reaction products. These results corresponded closely with percent conversions observed in the analytical reactions. The six-membered heterocycles 24b, c, e, and f were isolated in good yields from 62-66% (FIG. 8). The five-membered rings 24h-24j, 24i and 24m were also run on the 10 mg scale and isolated in yields varying from 55%-69% (FIG. 8). All novel cryptophycin analogs generated from these chemoenzymatic reactions were confirmed by HRMS, $^1$HNMR, and $^{13}$CNMR and subsequently tested for biological activity.

Example 6

Biological Evaluation of Novel Styrene Cryptophycin Analogs.

Figure 9:
FIG. 9. $IC_{50}$ values for cryptophycin analogs in HCT-116 human colorectal carcinoma.

Each of the cryptophycin analogs was assessed using a zone assay as a relative comparison of potency over a variety of cell lines (see Table 1), and the $IC_{50}$ for each analog was determined in the HCT-116 human colorectal cancer cell line. The potency of the initial monomethyl unit C analogs displayed significant variability in activities, depending on the heterocyclic ring present (FIG. 9). For the six-membered-ring heterocycles, the $IC_{50}$ values spanned a wide range even within the pyridyl set of analogs, with the 2-pyridyl analog showing an $IC_{50}$ of 102 nM, three orders of magnitude less than the 3-pyridyl-(24c) and 4-pyridyl-(24e) containing analogs (0.860 nM and 0.51 nM, FIG. 9). The five-membered rings showed even larger differences in $IC_{50}$ values, spanning almost six orders of magnitude. The inclusion of an isoxazole ring (24m) greatly diminished activity, with an $IC_{50}$ value of 1.4 μM. The introduction of a 4-methyl pyrazole ring (24 j), however, provided a low pico-molar analog, making it one of the most potent cryptophycin analogs observed to date.

TABLE 1

|  |  | LI210 | Col38 | CFU-GM | H116 | H125 | OVC-5 | U251N | MCF-7 | LNCaP | PANC-1 | CEM |
|---|---|---|---|---|---|---|---|---|---|---|---|---|
| DMSO |  | 0 | 0 | 0 | 0 | 0 | 0 | 0 | 0 | 0 | 0 | 0 |
| 2 pyridyl | 0.9 mg/ml | 500 | 700 | 500 | 500 | 600 | 650 | 700 | 800 | 850 | 600 | 500 |
| — | ¼ | 450 | 500 | 500 | 500 | 500 | 600 | 650 | 800 | 800 | 650 | 500 |
| — | ¹⁄₁₆ | 400 | 250 | 450 | 400 | 500 | 500 | 500 | 600 | 650 | 550 | 450 |
| 3 pyridyl | 2.4 mg/ml |  |  |  |  |  | 800 |  |  |  |  |  |
| — | ¼ |  |  |  |  |  | 750 |  |  |  |  |  |
| — | ¹⁄₁₆ | 800 | 700 | 700 | 800 | 850 | 700 | 800 | 500 | 800 | 800 | 600 |
| — | ¹⁄₆₄ | 650 | 650 | 600 | 650 | 800 | 650 | 600 | 450 | 800 | 750 | 600 |
| — | ¹⁄₂₅₆ | 550 | 500 | 500 | 500 | 600 |  | 600 | 400 | 700 | 600 | 350 |
| 4 pyridyl | 2 mg/ml |  |  |  |  |  | 800 |  |  |  |  |  |
| — | ¼ |  |  |  |  |  | 750 |  |  |  |  |  |
| — | ¹⁄₁₆ | 700 | 800 | 700 | 700 | 1000 | 750 | 750 | 550 | 850 | 800 | 750 |
| — | ¹⁄₆₄ | 600 | 700 | 550 | 600 | 800 | 750 | 600 | 450 | 800 | 750 | 650 |
| — | ¹⁄₂₅₆ | 550 | 500 | 450 | 500 | 650 | 600 | 600 | 400 | 700 | 600 | 600 |
| pyrazine | 2.2 mg/ml |  |  |  |  |  | 750 |  |  |  |  |  |
| — | ¼ |  |  |  |  |  | 700 |  |  |  |  |  |
| — | ¹⁄₁₆ | 700 | 700 | 550 | 600 | 750 | 650 | 750 | 500 | 800 | 750 | 750 |
| — | ¹⁄₆₄ | 550 | 450 | 500 | 400 | 600 |  | 600 | 400 | 750 | 700 | 600 |
| — | ¹⁄₂₅₆ | 300 | 200 | 350 | 300 | 450 |  | 550 | 300 | 500 | 600 | 450 |
| 2 methyl pyrazole | 2.6 mg/ml |  |  |  |  |  |  |  | >1000 |  |  |  |

TABLE 1-continued

| | | LI210 | Col38 | CFU-GM | H116 | H125 | OVC-5 | U251N | MCF-7 | LNCaP | PANC-1 | CEM |
|---|---|---|---|---|---|---|---|---|---|---|---|---|
| — | 1/4 | | | | | | | | >1000 | | | |
| — | 1/16 | | | | | | | | >1000 | | | 850 |
| — | 1/64 | 550 | 750 | 600 | 550 | 500 | >1000 | 900 | 800 | 900 | 700 | 600 |
| — | 1/256 | 400 | 500 | 500 | 350 | 450 | 850 | 800 | 600 | 700 | 600 | 500 |
| — | 1/1024+12 | 300 | 300 | 400 | 300 | 250 | 650 | 550 | 400 | 500 | 500 | 350 |
| 3 methyl pyrazole | | | | | | | | | | | | |
| — | 1/4 | | | | | | | | | | >1000 | |
| — | 1/16 | | | 500 | 600 | 650 | 750 | 850 | 800 | 900 | 900 | 800 |
| — | 1/64 | | | 300 | 400 | 500 | 550 | 750 | 650 | 700 | 700 | 550 |
| — | 1/256 | | | 100 | 250 | 250 | 300 | 400 | 400 | 500 | 500 | 400 |
| — | 1/1024 | | | 0 | 100 | 150 | 100 | 200 | 200 | 200 | 200 | 200 |
| 4 methyl pyrazole | 2.8 mg/ml | | | | | | 800 | | | | | |
| — | 1/4 | | | | | | 800 | | | | | |
| — | 1/16 | 350 | 800 | 400 | 450 | 850 | 900 | 800 | 550 | 1000 | 850 | 700 |
| — | 1/64 | 250 | 650 | 200 | 350 | 750 | 600 | 750 | 500 | 800 | 750 | 700 |
| — | 1/256 | 100 | 500 | 150 | 200 | 750 | 600 | 700 | 450 | 750 | 700 | 550 |
| — | 1/1024 | | | | | | | | | 700 | | 300 |
| Isopropyl pyrazole | 2.6 mg/ml | 600 | 850 | 550 | 600 | 550 | 800 | 750 | 800 | 900 | 700 | 450 |
| — | 1/4 | 550 | 800 | 600 | 550 | 550 | 600 | 550 | 600 | 800 | 600 | 450 |
| — | 1/16 | 500 | 600 | 500 | 500 | 450 | 600 | 550 | 550 | 700 | 550 | 450 |
| Isoxazole | 2.5 mg/ml | 200 | 400 | 250 | 300 | 350 | 400 | 400 | 500 | 500 | 400 | 350 |
| — | 1/4 | 200 | 250 | 250 | 250 | 300 | 500 | 500 | | | 500 | 300 |
| — | 1/16 | | 200 | | | 150 | 250 | 200 | 300 | 400 | 600 | 350 |
| 3 pyr dimethyl | | | | | | | | | | | | |
| — | 1/4 | | | 800 | 750 | 800 | 800 | 900 | 750 | 800 | 800 | 700 |
| — | 1/16 | | | 650 | 650 | 800 | 700 | 800 | 800 | 700 | 600 | 700 |
| — | 1/64 | | | 500 | 550 | 600 | 600 | 700 | 600 | 600 | 600 | 600 |
| — | 1/256 | | | 350 | 500 | 600 | 500 | 600 | 500 | 550 | 450 | 500 |
| — | 1/1024 | | | 200 | 300 | 400 | 400 | 450 | 400 | 400 | 400 | 400 |
| 4 pyr dimethyl | | | | | | | | | | | 900 | |
| — | 1/4 | | | | | | | | | | 800 | 750 |
| — | 1/16 | | | 650 | 750 | 800 | 650 | 850 | 850 | 800 | 750 | 600 |
| — | 1/64 | | | 500 | 550 | 650 | 600 | 700 | 800 | 600 | 600 | 600 |
| — | 1/256 | | | 400 | 500 | 600 | 500 | 600 | 600 | 600 | 600 | 500 |
| — | 1/1024 | | | 300 | 350 | 400 | 400 | 500 | 450 | 500 | 500 | 400 |
| 4MP-dimethyl | | | | | | | | | | | | |
| — | 1/4 | | | 500 | 800 | 850 | 800 | 900 | 800 | 800 | 800 | 800 |
| — | 1/16 | | | 200 | 800 | 800 | 450 | 600 | 700 | 600 | 400 | 650 |
| — | 1/64 | | | 100 | 750 | 750 | 300 | 450 | 250 | 500 | 50 | 600 |
| — | 1/256 | | | 0 | 600 | 600 | 100 | 300 | 450 | 400 | 200 | 550 |
| — | 1/1024 | | | | | | | 0 | 300 | 150 | 200 | 500 |

Data from zone assay run as described herein.

Example 7

Formulation and Biological Evaluation of Gem-dimethyl Analogs.

Utilizing the data disclosed herein to guide our design of analogs to test with the CrpTE biocatalyst, the geminal dimethyl unit C analogs were synthesized utilizing the chemistry described herein for our top three analogs: unit A bearing a terminal 3-pyridyl-, 4-pyridyl- or 4-methyl-pyrazole. The ester linkage between units C and D is known to be metabolically unstable and addition of a second methyl group adjacent to this labile position is known to improve the drug half-life.[45-46] We had shown there was an increase in hydrolytic byproducts (6:1 cyclization to hydrolysis versus 10:1) when including gem-dimethyl (unit C) in the benzyl-containing unit A.[37] New analogs 20d, f, and k were first tested on an analytical scale for a direct comparison of hydrolysis to cyclization ratios as well as % conversion to their monomethyl counterparts. All three showed an increase in hydrolytic activity when incubated with CrpTE (FIGS. 2 and 8) as well as a higher percentage of unreacted starting material, consistent with our previous findings. Despite the lower overall conversion to macrocycle, the corresponding chain elongation intermediates were processed with almost the same efficiency as the native substrate, further demonstrating the remarkable flexibility of CrpTE against substrates containing non-native functional groups in both the PKS- and NRPS-derived portions of the molecule.

These analogs were also tested in both the zone assay and for $IC_{50}$s in HCT-116. Incorporation of the gem dimethyl moiety resulted in a decrease in potency for all three analogs in this cell line, leading to the expectation that alternative methods for blocking metabolism at this site would result in analogs of greater potency.

REFERENCES

1. Weissman, K. J., Genetic engineering of modular PKSs: from combinatorial biosynthesis to synthetic biology. *Nat. Prod. Rep.* 2016, 33 (2), 203-30.
2. Walsh, C. T., Insights into the chemical logic and enzymatic machinery of NRPS assembly lines. *Nat. Prod. Rep.* 2016, 33 (2), 127-35.
3. Driggers, E. M.; Hale, S. P.; Lee, J.; Terrett, N. K., The exploration of macrocycles for drug discovery—an underexploited structural class. *Nature Reviews Drug Discovery* 2008, 7 (7), 608-624.
4. Horsman, M. E.; Hari, T. P.; Boddy, C. N., Polyketide synthase and non-ribosomal peptide synthetase thioesterase selectivity: logic gate or a victim of fate? *Nat. Prod. Rep.* 2016, 33 (2), 183-202.
5. Kohli, R. M.; Walsh, C. T., Enzymology of acyl chain macrocyclization in natural product biosynthesis. *Chem. Commun. (Camb)* 2003, (3), 297-307.
6. Clouthier, C. M.; Pelletier, J. N., Expanding the organic toolbox: a guide to integrating biocatalysis in synthesis. *Chem. Soc. Rev.* 2012, 41 (4), 1585-1605.
7. Weissman, K. J.; Leadlay, P. F., Combinatorial biosynthesis of reduced polyketides. *Nat. Rev. Microbiol.* 2005, 3 (12), 925-36.
8. Mortison, J. D.; Sherman, D. H., Frontiers and opportunities in chemoenzymatic synthesis. *J. Org. Chem.* 2010, 75 (21), 7041-51.
9. Kopp, F.; Grunewald, J.; Mahlert, C.; Marahiel, M. A., Chemoenzymatic design of acidic lipopeptide hybrids: New insights into the structure-activity relationship of daptomycin and A54145. *Biochemistry-Us* 2006, 45 (35), 10474-10481.
10. Yeh, E.; Lin, H. N.; Clugston, S. L.; Kohli, R. M.; Walsh, C. T., Enhanced macrocyclizing activity of the thioesterase from tyrocidine synthetase in presence of non-ionic detergent. *Chem. Biol.* 2004, 11 (11), 1573-1582.
11. Trauger, J. W.; Kohli, R. M.; Mootz, H. D.; Marahiel, M. A.; Walsh, C. T., Peptide cyclization catalysed by the thioesterase domain of tyrocidine synthetase. *Nature* 2000, 407 (6801), 215-218.
12. Trauger, J. W.; Kohli, R. M.; Walsh, C. T., Cyclization of backbone-substituted peptides catalyzed by the thioesterase domain from the tyrocidine nonribosomal peptide synthetase. *Biochemistry-Us* 2001, 40 (24), 7092-7098.
13. Bruner, S. D.; Weber, T.; Kohli, R. M.; Schwarzer, D.; Marahiel, M. A.; Walsh, C. T.; Stubbs, M. T., Structural basis for the cyclization of the lipopeptide antibiotic surfactin by the thioesterase domain SrfTE. *Structure* 2002, 10 (3), 301-310.
14. Samel, S. A.; Wagner, B.; Marahiel, M. A.; Essen, L. O., The thioesterase domain of the fengycin biosynthesis cluster: A structural base for the macrocyclization of a non-ribosomal lipopeptide. *J. Mol. Biol.* 2006, 359 (4), 876-889.
15. Akey, D. L.; Kittendorf, J. D.; Giraldes, J. W.; Fecik, R. A.; Sherman, D. H.; Smith, J. L., Structural basis for macrolactonization by the pikromycin thioesterase. *Nature Chemical Biology* 2006, 2 (10), 537-542.
16. Tsai, S. C.; Miercke, L. J. W.; Krucinski, J.; Gokhale, R.; Chen, J. C. H.; Foster, P. G.; Cane, D. E.; Khosla, C.; Stroud, R. M., Crystal structure of the macrocycle-forming thioesterase domain of the erythromycin polyketide synthase: Versatility from a unique substrate channel. *P Natl. Acad. Sci. USA* 2001, 98 (26), 14808-14813.
17. Giraldes, J. W.; Akey, D. L.; Kittendorf, J. D.; Sherman, D. H.; Smith, J. L.; Fecik, R. A., Structural and mechanistic insights into polyketide macrolactonization from polyketide-based affinity labels. *Nature Chemical Biology* 2006, 2 (10), 531-536.
18. Pinto, A.; Wang, M.; Horsman, M.; Boddy, C. N., 6-Deoxyerythronolide B Synthase Thioesterase-Catalyzed Macrocyclization Is Highly Stereoselective. *Org. Lett.* 2012, 14 (9), 2278-2281.
19. Hansen, D. A.; Koch, A. A.; Sherman, D. H., Identification of a Thioesterase Bottleneck in the Pikromycin Pathway through Full-Module Processing of Unnatural Pentaketides. *J. Am. Chem. Soc.* 2017, 139 (38), 13450-13455.
20. Koch, A. A.; Hansen, D. A.; Shende, V. V.; Furan, L. R.; Houk, K. N.; Jimenez-Oses, G.; Sherman, D. H., A Single Active Site Mutation in the Pikromycin Thioesterase Generates a More Effective Macrocyclization Catalyst. *J. Am. Chem. Soc.* 2017, 139 (38), 13456-13465.
21. Magarvey, N. A.; Beck, Z. Q.; Golakoti, T.; Ding, Y.; Huber, U.; Hemscheidt, T. K.; Abelson, D.; Moore, R. E.; Sherman, D. H., Biosynthetic characterization and chemoenzymatic assembly of the cryptophycins. Potent anticancer agents from cyanobionts. *ACS chemical biology* 2006, 1 (12), 766-79.
22. Ding, Y.; Rath, C. M.; Bolduc, K. L.; Hakansson, K.; Sherman, D. H., Chemoenzymatic synthesis of cryptophycin anticancer agents by an ester bond-forming non-ribosomal peptide synthetase module. *J. Am. Chem. Soc.* 2011, 133 (37), 14492-5.
23. Schwartz, R. E.; Hirsch, C. F.; Sesin, D. F.; Flor, J. E.; Chartrain, M.; Fromtling, R. E.; Harris, G. H.; Salvatore, M. J.; Liesch, J. M.; Yudin, K., Pharmaceuticals from Cultured Algae. *J. Ind. Microbiol.* 1990, 5 (2-3), 113-123.
24. Smith, C. D.; Zhang, X. Q.; Mooberry, S. L.; Patterson, G. M. L.; Moore, R. E., Cryptophycin—a New Antimicrotubule Agent Active against Drug-Resistant Cells. *Cancer Res.* 1994, 54 (14), 3779-3784.
25. D'Agostino, G.; del Campo, J.; Mellado, B.; Izquierdo, M. A.; Minarik, T.; Cirri, L.; Marini, L.; Perez-Gracia, J. L.; Scambia, G., A multicenter phase II study of the cryptophycin analog LY355703 in patients with platinum-resistant ovarian cancer. *International journal of gynecological cancer: official journal of the International Gynecological Cancer Society* 2006, 16 (1), 71-6.
26. Stevenson, J. P.; Sun, W.; Gallagher, M.; Johnson, R.; Vaughn, D.; Schuchter, L.; Algazy, K.; Hahn, S.; Enas, N.; Ellis, D.; Thornton, D.; O'Dwyer, P. J., Phase I trial of the cryptophycin analogue LY355703 administered as an intravenous infusion on a day 1 and 8 schedule every 21 days. *Clinical cancer research: an official journal of the American Association for Cancer Research* 2002, 8 (8), 2524-9.
27. Sessa, C.; Weigang-Kohler, K.; Pagani, 0.; Greim, G.; Mora, 0.; De Pas, T.; Burgess, M.; Weimer, I.; Johnson, R., Phase I and pharmacological studies of the cryptophycin analogue LY355703 administered on a single intermittent or weekly schedule. *European journal of cancer* 2002, 38 (18), 2388-2396.
28. Edelman, M. J.; Gandara, D. R.; Hausner, P.; Israel, V.; Thornton, D.; DeSanto, J.; Doyle, L. A., Phase 2 study of cryptophycin 52 (LY355703) in patients previously treated with platinum based chemotherapy for advanced non-small cell lung cancer. *Lung cancer* 2003, 39 (2), 197-9.
29. Eggen, M.; Georg, G. I., The cryptophycins: their synthesis and anticancer activity. *Medicinal research reviews* 2002, 22 (2), 85-101.
30. Nahrwold, M.; Weiss, C.; Bogner, T.; Mertink, F.; Conradi, J.; Sammet, B.; Palmisano, R.; Royo Gracia, S.; Preusse, T.; Sewald, N., Conjugates of modified cryptophycins and RGD-peptides enter target cells by endocytosis. *Journal of medicinal chemistry* 2013, 56 (5), 1853-64.
31. Leamon, C. P.; Wang, Y.; Vlahov, I. R.; You, F.; Kleindl, P. J.; Santhapuram, H. K. R. Conjugates containing hydrophilic spacer linkers. WO2009002993A1, 2008/12/31/, 2008.
32. Su, D.; Kozak, K. R.; Sadowsky, J.; Yu, S. F.; Fourie-O'Donohue, A.; Nelson, C.; Vandlen, R.; Ohri, R.; Liu, L. N.; Ng, C.; He, J. T.; Davis, H.; Lau, J.; Del Rosario, G.;

Cosino, E.; dela Cruz-Chuh, J.; Ma, Y.; Zhang, D. L.; Darwish, M.; Cai, W. W.; Chen, C. J.; Zhou, H. X.; Lu, J. W.; Liu, Y. C.; Kaur, S.; Xu, K. Y.; Pillow, T. H., Modulating Antibody-Drug Conjugate Payload Metabolism by Conjugation Site and Linker Modification. *Bioconjugate Chem* 2018, 29 (4), 1155-1167.

33. Verma, V. A.; Pillow, T. H.; DePalatis, L.; Li, G.; Phillips, G. L.; Polson, A. G.; Raab, H. E.; Spencer, S.; Zheng, B., The cryptophycins as potent payloads for antibody drug conjugates. *Bioorg. Med. Chem. Lett.* 2015, 25 (4), 864-868.

34. Bigot, A.; Bouchard, H.; Brun, M.-P.; Clerc, F.; Zhang, J. Novel Cryptophycin Compounds and Conjugates, Their Preparation and Their Therapeutic Use. WO2017076998 (A1), 2017/05/11/, 2017.

35. Steinkuhler, M. C.; Gallinari, M. P.; Osswald, B.; Sewald, N.; Ritzefeld, M.; Frese, M. Cryptophycin-Based Antibody-Drug Conjugates with Novel Self-Immolative Linkers. WO2016146638 (A1), 2016/09/22/, 2016.

36. Bouchard, H.; Brun, M.-P.; Commercon, A.; Zhang, J. Novel Conjugates, Preparation Thereof, and Therapeutic Use Thereof. WO2011001052 (A1), 2011/01/06/, 2011.

37. Beck, Z. Q.; Aldrich, C. C.; Magarvey, N. A.; Georg, G. I.; Sherman, D. H., Chemoenzymatic synthesis of cryptophycin/arenastatin natural products. *Biochemistry-Us* 2005, 44 (41), 13457-13466.

38. Bolduc, K. L.; Larsen, S. D.; Sherman, D. H., Efficient, divergent synthesis of cryptophycin unit A analogues. *Chem. Commun. (Camb)* 2012.

39. Kotoku, N.; Kato, T.; Narumi, F.; Ohtani, E.; Kamada, S.; Aoki, S.; Okada, N.; Nakagawa, S.; Kobayashi, M., Synthesis of 15,20-triamide analogue with polar substituent on the phenyl ring of arenastatin A, an extremely potent cytotoxic spongean depsipeptide. *Bioorgan. Med. Chem.* 2006, 14 (22), 7446-7457.

40. Krishnamurthy, S., Rapid Reduction of Alkyl Tosylates with Lithium Triethylborohydride—Convenient and Advantageous Procedure for Deoxygenation of Simple and Hindered Alcohols—Comparison of Various Hydride Reagents. *J. Organomet. Chem.* 1978, 156 (1), 171-181.

41. Ghosh, A. K.; Swanson, L., Enantioselective synthesis of (+)-cryptophycin 52 (LY355703), a potent antimitotic antitumor agent. *J. Org. Chem.* 2003, 68 (25), 9823-6.

42. McCubbin, J. A.; Maddess, M. L.; Lautens, M., Total synthesis of cryptophycin analogues via a scaffold approach. *Org. Lett.* 2006, 8 (14), 2993-6.

43. Mast, C. A.; Eissler, S.; Stoncius, A.; Stammler, H. G.; Neumann, B.; Sewald, N., Efficient and versatile stereoselective synthesis of cryptophycins. *Chemistry* 2005, 11 (16), 4667-77.

44. Nicolaou, K. C.; Estrada, A. A.; Zak, M.; Lee, S. H.; Safina, B. S., A mild and selective method for the hydrolysis of esters with trimethyltin hydroxide. *Angew Chem. Int. Edit.* 2005, 44 (9), 1378-1382.

45. Wagner, M. M.; Paul, D. C.; Shih, C.; Jordan, M. A.; Wilson, L.; Williams, D. C., In vitro pharmacology of cryptophycin 52 (LY355703) in human tumor cell lines. *Cancer chemotherapy and pharmacology* 1999, 43 (2), 115-125.

46. Golakoti, T.; Ogino, J.; Heltzel, C. E.; LeHusebo, T.; Jensen, C. M.; Larsen, L. K.; Patterson, G. M. L.; Moore, R. E.; Mooberry, S. L.; Corbett, T. H.; Valeriote, F. A., Structure determination, conformational analysis, chemical stability studies, and antitumor evaluation of the cryptophycins. Isolation of 18 new analogs from Nostoc sp strain GSV 224 (vol 117, pg 12030, 1995). *J. Am. Chem. Soc.* 1996, 118 (13), 3323-3323.

From the disclosure herein it will be appreciated that, although specific embodiments of the disclosure have been described herein for purposes of illustration, various modifications may be made without deviating from the spirit and scope of the disclosure.

What is claimed is:

1. A compound, or pharmaceutically acceptable salt thereof, having a structure of formula I:

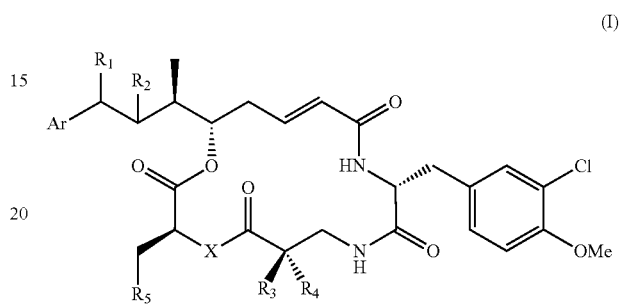

wherein

Ar is a 5- or 6-membered heterocyclic aryl group having 1 to 3 ring N heteroatoms, and is optionally substituted with 1-3 substituents independently selected from $C_{1-5}$ alkyl and L-$R_6$;

$R_1$ is chlorine, bromine, or iodine;

$R_2$ is OH or OC(O)CH$_2$NHR; or $R_1$ and $R_2$ together (1) indicate a double bond between the carbons to which they are attached or (2) form a β-epoxide ring with the carbons to which they are attached;

each of $R_3$ and $R_4$ is independently H, $C_{1-6}$alkyl, $C_{0-6}$alkylene-OH or $C_{0-6}$alkylene-NH(R); or $R_3$ and $R_4$ together with the carbon atom to which they are attached form a spiro $C_{3-5}$ cycloalkyl or a spiro 3- to 5-membered heterocycloalkyl having one nitrogen ring atom;

$R_5$ is $C_{1-6}$alkyl, $C_{0-6}$alkylene-OH or $C_{0-6}$alkylene-NH(R); and

R is H, $C_{1-6}$alkyl, or L-$R_6$;

L is a linker;

$R_6$ is a maleimido group, a maleimidocaproyl group, a maleimido PEG group, a bromoacetamide group, a N-hydroxysuccinimide ester, an O-alkyl hydroxylamine, or a combination thereof; and X is O, NH or NMe, with the proviso that the compound or salt has 0 or 1 L-$R_6$.

2. The compound or salt according to claim 1, wherein (1) Ar is

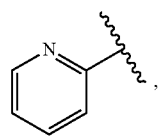 [SMILES: *c1ccccn1]

$R_3$ is CH$_3$, and $R_4$ is H;

(2) Ar is

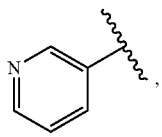 [SMILES: *c1cccnc1]

R$_3$ is CH$_3$, and R$_4$ is H or CH$_3$;
(3) Ar is

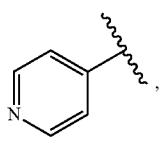

R$_3$ is CH$_3$, and R$_4$ is H or CH$_3$;
(4) Ar is

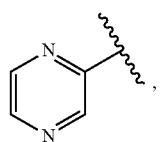 [SMILES: *c1cnccn1]

R$_3$ is CH$_3$, and R$_4$ is H;
(5) Ar is

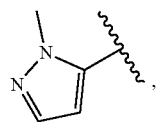

R$_3$ is CH$_3$, and R$_4$ is H;
(6) Ar is

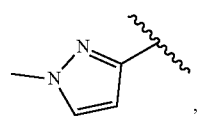

R$_3$ is CH$_3$, and R$_4$ is H;
(7) Ar is

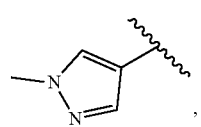 [SMILES: *c1cnn(C)c1]

R$_3$ is CH$_3$, and R$_4$ is H or CH$_3$;

(8) Ar is

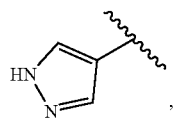

R$_3$ is CH$_3$, and R$_4$ is H or CH$_3$; or
(9) Ar is

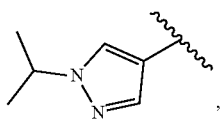 [SMILES: *c1cnn(C(C)C)c1]

R$_3$ is CH$_3$, and R$_4$ is H.

3. The compound or salt according to claim 1 wherein:
  (i) R$_1$ and R$_2$ together indicate a double bond between the carbons to which they are attached,
  (ii) R$_1$ and R$_2$ together form a β-epoxide ring with the carbons to which they are attached,
  (iii) R$_1$ is Cl and R$_2$ is OH,
  (iv) R$_1$ is Cl and R$_2$ is OC(O)CH$_2$NH$_2$, or
  (v) R$_2$ is OC(O)CH$_2$NHL(R$_6$) and R$_1$ is Cl.

4. The compound or salt according to claim 3, wherein
(1) Ar is

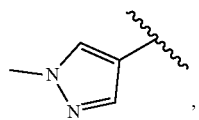

R$_3$ is CH$_3$, R$_4$ is H or CH$_3$, and R$_5$ is CH(CH$_3$)$_2$;
(2) Ar is

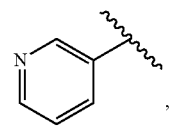

R$_3$ is CH$_3$, R$_4$ is H or CH$_3$, and R$_5$ is CH(CH$_3$)$_2$; or
(3) Ar is

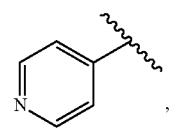

R$_3$ is CH$_3$, R$_4$ is H or CH$_3$, and R$_5$ is CH(CH$_3$)$_2$.

5. The compound or salt according to claim 1, wherein:
  (i) R$_3$ is NH$_2$, NHMe, CH$_2$—NH$_2$, or CH$_2$-NHMe or
  (ii) R$_3$ is OH or CH$_2$—OH.

6. The compound or salt according to claim 1, wherein R$_5$ is NH$_2$, NHMe, (CH)CH$_3$NH$_2$, or (CH)CH$_3$NHMe.

7. The compound or salt according to claim 1, wherein:
(i) X is O, or
(ii) NH or NMe.
8. The compound or salt according to claim 1, wherein the structure is selected from the group consisting of
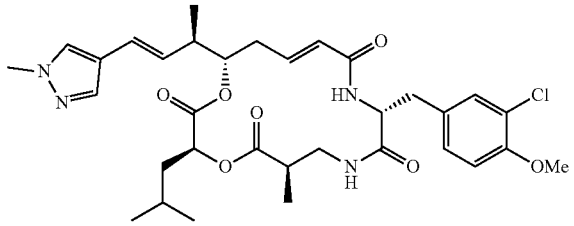
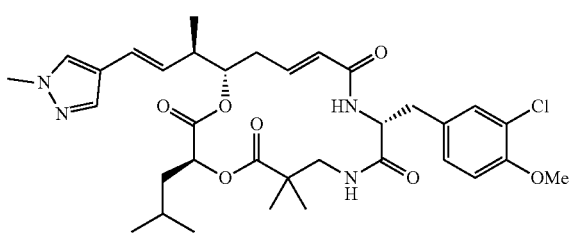
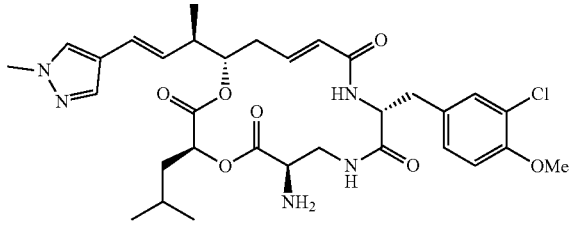
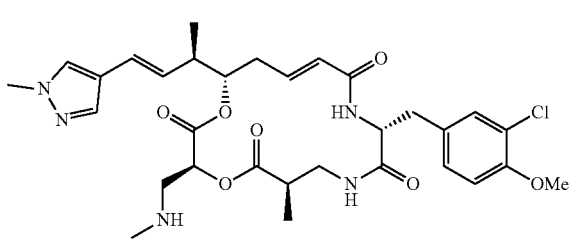
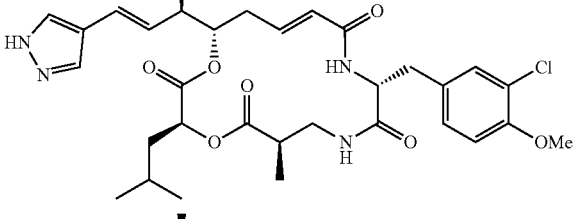
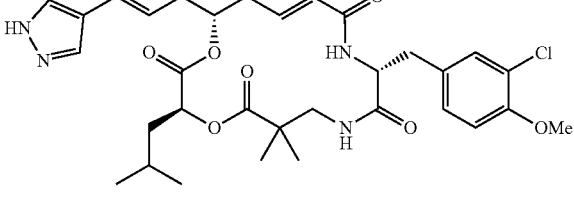
-continued
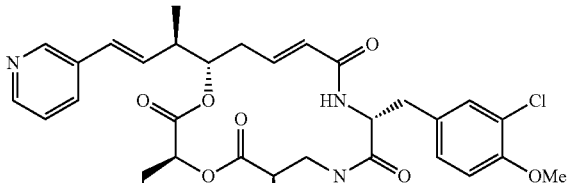
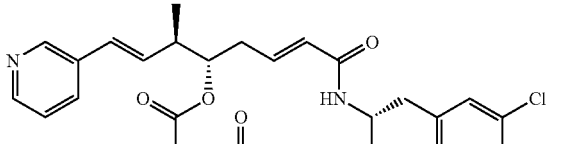
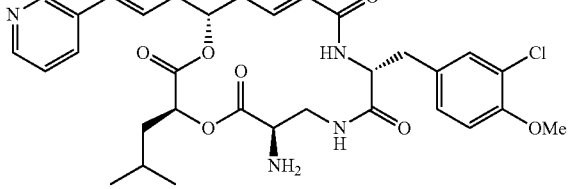
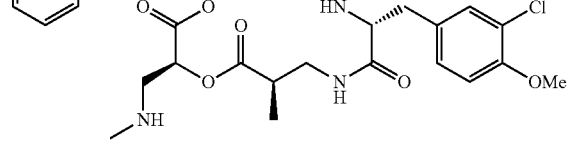
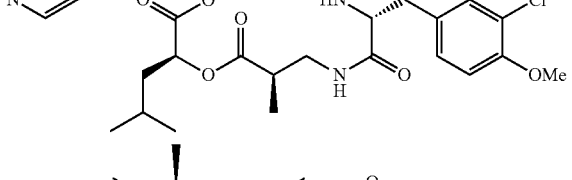
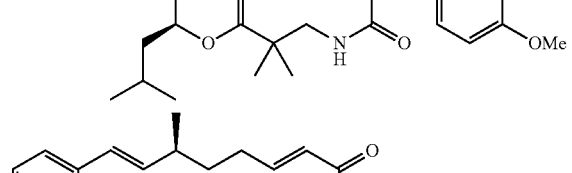
and -continued

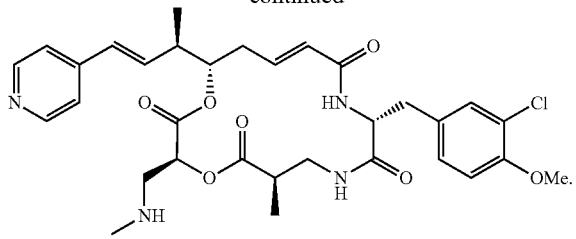

9. The compound or salt according to claim 1, wherein Ar is

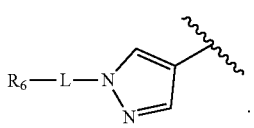

10. The compound or salt according to claim 1, wherein $R_3$ is NH-L$R_6$, and $R_4$ is H.

11. The compound or salt according to claim 10 wherein
(1) Ar is

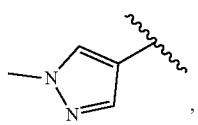 [SMILES: *c1cnn(C)c1]

$R_1$ and $R_2$ together indicate a double bond or a β-epoxide, and $R_5$ is CH(CH$_3$)$_2$;
(2) Ar is

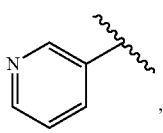

$R_1$ and $R_2$ together indicate a double bond or a β-epoxide, and $R_5$ is CH(CH$_3$)$_2$; or
(3) Ar is

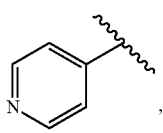 [SMILES: *c1ccncc1]

$R_1$ and $R_2$ together indicate a double bond or a β-epoxide, and $R_5$ is CH(CH$_3$)$_2$, CH(CH$_3$)$_2$.

12. The compound or salt according to claim 1, wherein $R_5$ is NH-L$R_6$.

13. The compound or salt according to claim 12, wherein
(1) Ar is

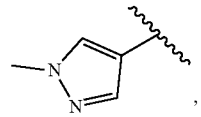 [SMILES: *c1cnn(C)c1]

$R_1$ and $R_2$ together indicate a double bond or a β-epoxide, $R_3$ is CH$_3$, and $R_4$ is H or CH$_3$;
(2) Ar is

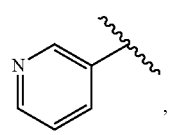

$R_1$ and $R_2$ together indicate a double bond or a β-epoxide, $R_3$ is CH$_3$, and $R_4$ is H or CH$_3$; or
(3) Ar is

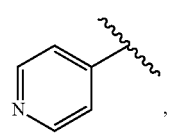

$R_1$ and $R_2$ together indicate a double bond or a β-epoxide, $R_3$ is CH$_3$, and $R_4$ is H or CH$_3$.

14. The compound or salt according to claim 9, wherein L comprises (a) a peptide having 1 to 10 amino acids, (b) a polyethylene glycol having 1 to 15 ethylene glycol monomers, or (c) a β-glucuronic acid, or any combination of the above.

15. The compound or salt according to claim 9, wherein L is attached via a single bond, an ester bond, an amide bond, a sulfide bond, a disulfide bond, a para-amino benzyl (PAB) group or via a para-amino benzyloxycarbonyl (PABC) group.

16. The compound or salt according to claim 1, wherein Ar comprises pyrazolyl optionally substituted with 1-3 substituents selected from methyl and isopropyl.

17. A method of producing the compound or salt according to claim 1 comprising contacting a seco cryptophycin intermediate with a cryptophycin thioesterase under conditions suitable for macrocyclization to form the compound or salt.

18. A conjugate comprising the compound or salt of claim 9 and a peptide, a protein, or an antibody.

19. A method of treating colorectal cancer comprising administering a compound or salt according to claim 1 to a patient in need thereof.

* * * * *